United States Patent
Galligan et al.

(10) Patent No.: US 9,265,488 B2
(45) Date of Patent: *Feb. 23, 2016

(54) SUTURING DEVICE AND METHOD FOR SEALING AN OPENING IN A BLOOD VESSEL OR OTHER BIOLOGICAL STRUCTURE

(71) Applicant: Medtronic Vascular, Inc., Santa Rosa, CA (US)

(72) Inventors: Darren Galligan, San Francisco, CA (US); Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 192 days.

This patent is subject to a terminal disclaimer.

(21) Appl. No.: 14/036,677

(22) Filed: Sep. 25, 2013

(65) Prior Publication Data

US 2014/0276982 A1  Sep. 18, 2014

Related U.S. Application Data

(63) Continuation-in-part of application No. 13/802,551, filed on Mar. 13, 2013, now Pat. No. 9,095,319.

(51) Int. Cl.
| | |
|---|---|
| *A61B 17/04* | (2006.01) |
| *A61B 17/00* | (2006.01) |
| *A61B 17/06* | (2006.01) |

(52) U.S. Cl.
CPC .......... *A61B 17/0057* (2013.01); *A61B 17/0469* (2013.01); *A61B 17/0482* (2013.01);
(Continued)

(58) Field of Classification Search
CPC ........... A61B 17/0057; A61B 17/0469; A61B 17/0482; A61B 17/0485; A61B 2017/00663; A61B 2017/0472; A61B 2017/06052
See application file for complete search history.

(56) References Cited

U.S. PATENT DOCUMENTS

| | | | |
|---|---|---|---|
| 5,304,184 | A | 4/1994 | Hathaway et al. |
| 5,476,469 | A | 12/1995 | Hathaway et al. |

(Continued)

FOREIGN PATENT DOCUMENTS

| | | |
|---|---|---|
| AU | 2003212025 | 3/2006 |
| AU | 2006251579 | 5/2006 |

(Continued)

OTHER PUBLICATIONS

U.S. Appl. No. 61/299,297, filed Jan 28, 2010, Nobles.
(Continued)

*Primary Examiner* — Ryan J Severson

(57) ABSTRACT

A suturing device includes a handle, an elongated body, at least one suture snag, at least one pair of needles, and at least one suture pair. The suture snag is moveable between a deployed position in which two distal arm portions thereof radially extend away from the elongated body and a retracted position in which the two distal arm portions are disposed within the elongated body. The suture pair is slidingly disposed through the needle pair. The suturing device deploys the suture snag within a vessel adjacent to an arteriotomy, extends the needle pair through a vessel wall around the arteriotomy and through the deployed suture snag, extends the suture pair beyond the distal ends of the needle pair, and then utilizes the suture snag to capture the extended suture pair by retracting the suture snag to pull first or distal ends of the sutures back into the suturing device. An inflatable balloon or an expandable suture capture component may be alternatives to the suture snag for capturing the suture ends.

20 Claims, 46 Drawing Sheets

(52) U.S. Cl.
CPC ........... *A61B2017/00477* (2013.01); *A61B 2017/00557* (2013.01); *A61B 2017/00663* (2013.01); *A61B 2017/00862* (2013.01); *A61B 2017/0472* (2013.01); *A61B 2017/06052* (2013.01)

(56) References Cited

U.S. PATENT DOCUMENTS

| | | | |
|---|---|---|---|
| 5,720,757 A | 2/1998 | Hathaway et al. |
| 5,810,850 A | 9/1998 | Hathaway et al. |
| 5,820,631 A | 10/1998 | Nobles |
| 5,860,990 A | 1/1999 | Nobles et al. |
| 6,117,144 A | 9/2000 | Nobles et al. |
| 6,132,440 A | 10/2000 | Hathaway et al. |
| 6,245,079 B1 | 6/2001 | Nobles et al. |
| 6,348,059 B1 | 2/2002 | Hathaway et al. |
| 6,551,331 B2 | 4/2003 | Nobles et al. |
| 6,562,052 B2 | 5/2003 | Nobles et al. |
| 6,733,509 B2 | 5/2004 | Nobles et al. |
| 6,911,034 B2 | 6/2005 | Nobles et al. |
| 6,939,356 B2 | 9/2005 | Debbas et al. |
| 7,004,952 B2 | 2/2006 | Nobles et al. |
| 7,060,078 B2 | 6/2006 | Hathaway et al. |
| 7,090,686 B2 | 8/2006 | Nobles et al. |
| 7,235,087 B2 | 6/2007 | Modesitt et al. |
| 7,670,349 B2 | 3/2010 | Hathaway et al. |
| 7,686,821 B2 | 3/2010 | Hathaway et al. |
| 7,731,726 B2 | 6/2010 | Belhe et al. |
| 7,803,167 B2 | 9/2010 | Nobles et al. |
| 7,842,050 B2 | 11/2010 | Diduch et al. |
| 7,846,170 B2 | 12/2010 | Modesitt et al. |
| 7,905,892 B2 | 3/2011 | Nobles et al. |
| 8,048,092 B2 | 11/2011 | Modesitt et al. |
| 8,197,497 B2 | 6/2012 | Nobles et al. |
| 8,197,510 B2 | 6/2012 | Nobles |
| 8,246,636 B2 | 8/2012 | Nobles et al. |
| 8,277,463 B2 | 10/2012 | Suzuki et al. |
| 8,348,962 B2 | 1/2013 | Nobles et al. |
| 8,623,032 B2 | 1/2014 | Diduch et al. |
| 8,672,955 B2 | 3/2014 | Nagata et al. |
| 8,834,494 B2 | 9/2014 | Schorr et al. |
| 8,876,840 B2 | 11/2014 | Harada et al. |
| 2002/0049453 A1 | 4/2002 | Nobles et al. |
| 2002/0147456 A1 | 10/2002 | Diduch et al. |
| 2003/0171764 A1 | 9/2003 | Debas |
| 2004/0010273 A1 | 1/2004 | Diduch et al. |
| 2004/0068273 A1 | 4/2004 | Fariss et al. |
| 2004/0097978 A1 | 5/2004 | Modesitt et al. |
| 2005/0070923 A1 | 3/2005 | McIntosh |
| 2005/0121042 A1 | 6/2005 | Behle et al. |
| 2005/0228407 A1 | 10/2005 | Nobles |
| 2006/0030868 A1 | 2/2006 | Bennett |
| 2007/0167959 A1 | 7/2007 | Modesitt et al. |
| 2007/0179509 A1 | 8/2007 | Nagata et al. |
| 2007/0225744 A1 | 9/2007 | Nobles |
| 2007/0276414 A1 | 11/2007 | Nobles |
| 2007/0282351 A1 | 12/2007 | Harada et al. |
| 2008/0097481 A1 | 4/2008 | Schorr et al. |
| 2008/0255591 A1 | 10/2008 | Harada et al. |
| 2009/0062817 A1 | 3/2009 | Suzuki et al. |
| 2009/0062852 A1 | 3/2009 | Marino |
| 2010/0030242 A1 | 2/2010 | Nobles et al. |
| 2010/0042118 A1 | 2/2010 | Garrison et al. |
| 2010/0249808 A1 | 9/2010 | Harada et al. |
| 2010/0305586 A1 | 12/2010 | Nagata et al. |
| 2011/0071550 A1 | 3/2011 | Diduch et al. |
| 2011/0077670 A1 | 3/2011 | Modesitt et al. |
| 2011/0082475 A1 | 4/2011 | Smith |
| 2011/0270282 A1 | 11/2011 | Lemke |
| 2011/0288563 A1 | 11/2011 | Gianotti et al. |
| 2014/0276975 A1 | 9/2014 | Argentine |
| 2014/0276976 A1 | 9/2014 | Argentine |

FOREIGN PATENT DOCUMENTS

| | | |
|---|---|---|
| AU | 2006262498 | 6/2006 |
| CA | 2323084 | 12/2006 |
| EP | 0830843 | 3/1998 |
| EP | 941698 | 5/2005 |
| EP | 1570790 | 11/2008 |
| EP | 2011441 | 1/2009 |
| JP | 2009144590 | 2/1999 |
| JP | 2007533759 | 9/2005 |
| JP | 2008513600 | 5/2006 |
| JP | 2008517194 | 6/2006 |
| JP | 2010501228 | 3/2008 |
| WO | WO9925254 | 5/1999 |
| WO | WO0167963 | 9/2001 |
| WO | WO2006/037039 | 4/2006 |
| WO | WO2006/127636 | 11/2006 |
| WO | WO2007/001936 | 1/2007 |
| WO | WO2007025302 | 3/2007 |
| WO | WO2008/121738 | 10/2008 |
| WO | WO2009/137766 | 11/2009 |
| WO | WO2010048945 | 5/2010 |

OTHER PUBLICATIONS

PCT/US2014/053283—PCT International Search Report and Written Opinion, mailed on Nov. 6, 2014.

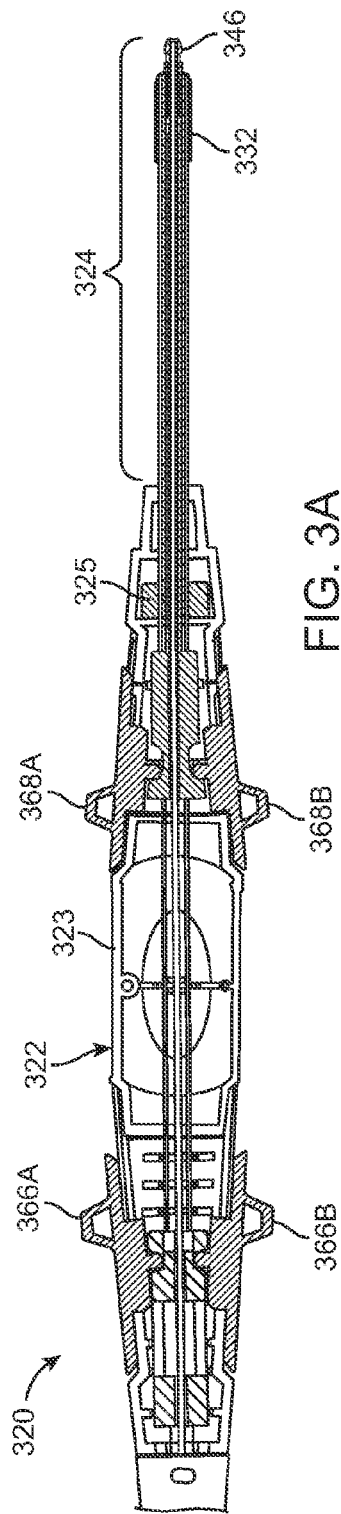
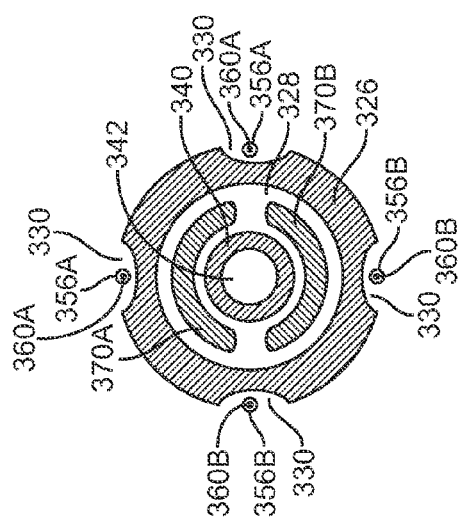

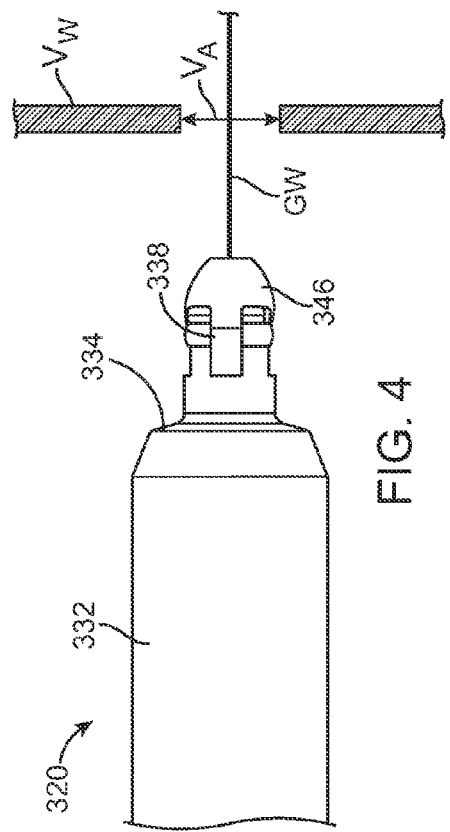
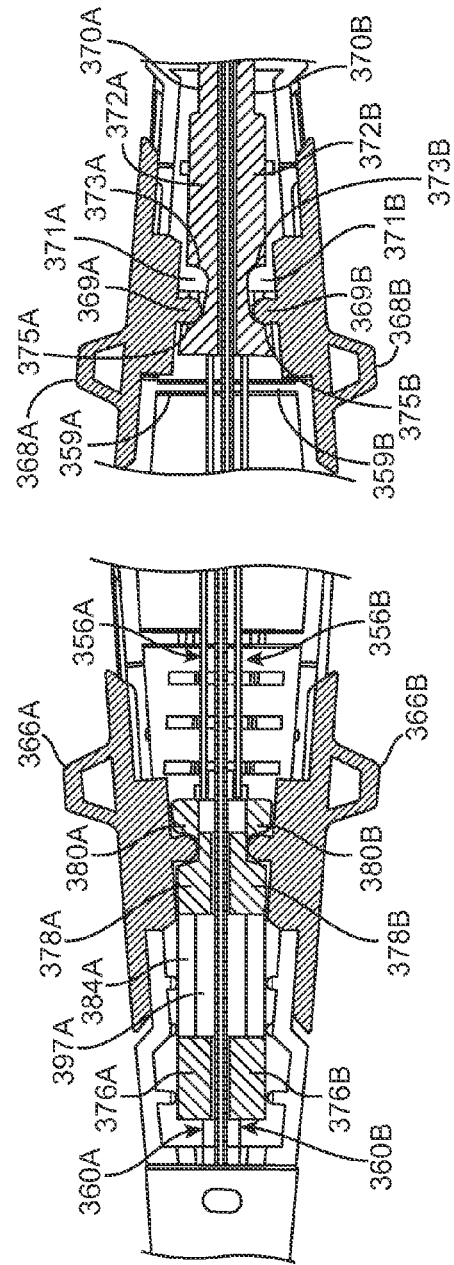
FIG. 4
FIG. 4A
FIG. 4B

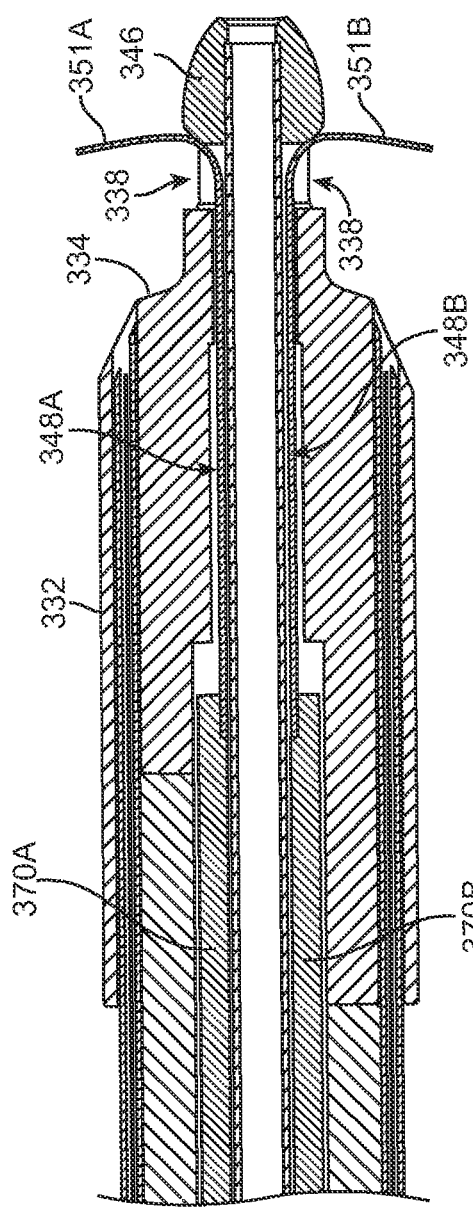
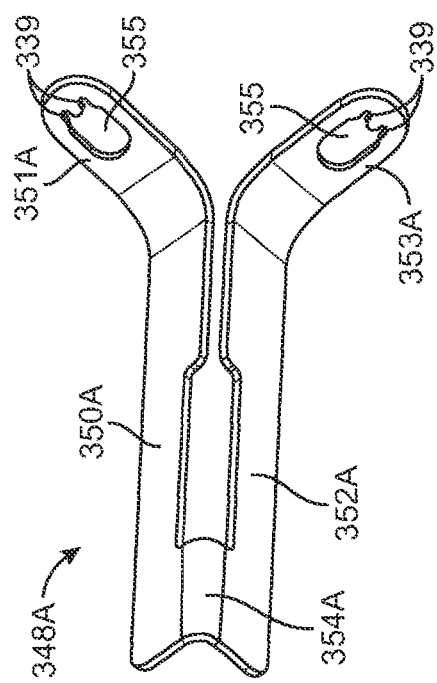
FIG. 6B
FIG. 6C

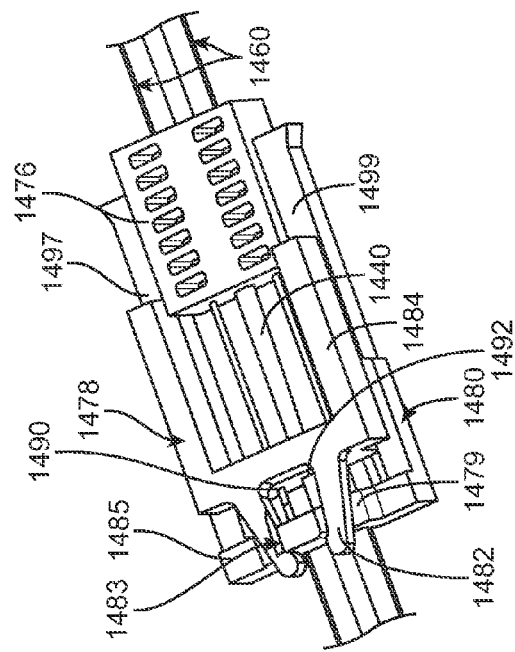
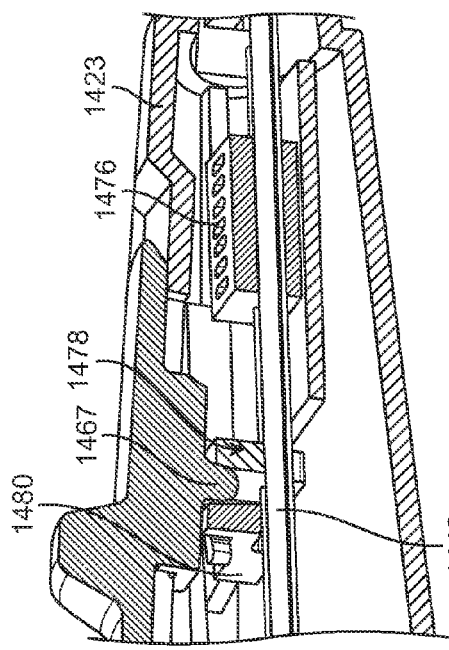
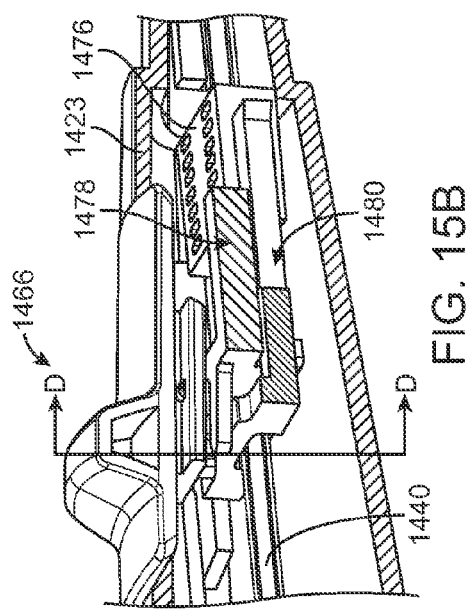

SUTURING DEVICE AND METHOD FOR SEALING AN OPENING IN A BLOOD VESSEL OR OTHER BIOLOGICAL STRUCTURE

CROSS-REFERENCE TO RELATED APPLICATION

This application is a continuation-in-part of U.S. application Ser. No. 13/802,551, filed Mar. 13, 2013, now U.S. Pat. No. 9,095,319, which is hereby incorporated by reference herein in its entirety

FIELD OF THE INVENTION

The present invention relates to medical suturing devices, and more particularly, to suturing devices for closing an opening in an arterial or other biological tissue wall that is not directly accessible to a user.

BACKGROUND OF THE INVENTION

Various cardiovascular procedures, such as angioplasty, stent placement and atherectomy, require gaining access to the vasculature. With reference to FIGS. 1 and 2, access to the vasculature of a patient 100 typically is through the femoral artery and is percutaneous, involving insertion of a needle (not shown), and in some cases a dilator (not shown), in the region of the groin to form a track 104 through subcutaneous tissue 106 and to puncture and create an arteriotomy $V_A$ in a vessel wall $V_W$ of the femoral artery. A guidewire GW is then advanced through the needle and into the femoral artery. The needle and dilator, if present, are then removed. A catheter or other interventional device 102 is then advanced over the guidewire GW, along the track 104 and into the femoral artery in order to perform the selected procedure.

The size of the puncture opening in the artery corresponds to the size of the catheter or interventional device used, and such devices may typically range in diameter from 5 French for a diagnostic procedure to 6-20 French for a therapeutic procedure. In some cases, medical suturing systems are utilized to "pre-close" the arteriotomy $V_A$ by positioning one or more stitches adjacent to interventional device 102 that result in hemostasis of the arteriotomy $V_A$ around the interventional device 102 during the procedure. After the procedure is completed and the interventional device(s) are removed, the stitches positioned by the medical suturing system are utilized to fully close the arteriotomy $V_A$.

In other cases, i.e., when the size of the arteriotomy is relatively small, such pre-closure is not required and a medical suturing system or other technique is utilized to close the arteriotomy after the interventional device(s) are removed. A number of other techniques are known to facilitate closure and healing of the arteriotomy. One technique includes application of pressure at the puncture site for a relatively extended length of time. More particularly, compression has traditionally been applied to the puncture site for at least 30-45 minutes for the wound to close naturally after removal of the catheter. Patients are required to remain lying down, essentially motionless and often with a heavy sandbag placed on their upper leg, for several hours to ensure that the bleeding has stopped. The recovery time from the medical procedure may be as little as half of an hour, but the recovery time from the wound can exceed twenty-four hours. Longer recovery times may result in increased expenses, increased patient discomfort, and greater the risk of complications. Other approaches to arteriotomy closure include a compression clamp device, a thrombotic or collagen plug, biological adhesives adapted to seal the arteriotomy, and/or stapling devices.

Medical suturing systems that have been proposed facilitate closure and healing of the arteriotomy and resolve some of the concerns associated with arteriotomy closure during and after vascular catheterization procedures. However, a need in the art still exists for a medical suturing system that consistently and reliably facilitates closure and healing of the arteriotomy.

BRIEF SUMMARY OF THE INVENTION

Embodiments hereof relate to a suturing device including a handle, an elongated body coupled to a distal end of the handle, and a shaft slidingly disposed within the handle and the elongated body. An expandable suture capture component is mounted on a distal portion of the shaft, the expandable suture capture component being operable to alternate between a deployed configuration in which the expandable suture capture component radially expands and extends away from the elongated body and a compressed configuration in which the expandable suture capture component is disposed within the elongated body. The suturing device also includes at least one pair of needles moveable to a deployed position in which the at least one pair of needles distally extend from the distal end of the elongated body and into the expandable suture capture component with the expandable suture capture component in its deployed configuration and a retracted position in which the at least one pair of needles is disposed within the elongated body. Each needle includes a distal end configured to penetrate through a vessel wall.

Embodiments hereof also relate to a suturing device for positioning a suture in situ, the suturing device including a handle, an elongated body coupled to a distal end of the handle, and a shaft slidingly disposed within the handle and the elongated body. The handle has a first actuation mechanism and a second actuation mechanism, wherein the second actuation mechanism includes a suture holder and a needle holder disposed within the handle. The shaft is moveable via the first actuation mechanism. An expandable suture capture component is mounted on a distal portion of the shaft and the expandable suture capture component is moveable between a deployed configuration in which the expandable suture capture component radially expands and extends away from the elongated body and a compressed configuration in which the expandable suture capture component is disposed within the elongated body. The suturing device also includes a pair of needles extending through the handle and through the elongated body, each needle including a distal end configured to penetrate through a vessel wall. The pair of needles is coupled to the needle holder and the second actuation mechanism moves the pair of needles to a deployed position in which the pair of needles distally extend away from the distal end of the elongated body and into the expandable suture capture component with the expandable suture capture component in its deployed configuration and a retracted position in which the pair of needles is disposed within the elongated body. A pair of sutures is slidingly disposed through the pair of needles. The sutures are coupled to the suture holder when the needles are in their deployed position and are disengaged from the suture holder when the needles are in their retracted position and wherein the second actuation mechanism moves the pair of sutures relative to the pair of needles from a loaded position in which each first end of each suture is disposed within its respective needle to a deployed position in which each first end of each suture extends distally beyond the distal end of its respective needle.

Embodiments hereof also relate to a method of positioning a suture at an arteriotomy of a vessel wall of a vessel. A distal end of a suturing device is positioned through the arteriotomy, wherein the suturing device includes a handle, an elongated body coupled to a distal end of the handle, and a shaft slidingly disposed within the handle and the elongated body. An expandable suture capture component is mounted on a distal portion of the shaft and is in a compressed configuration in which the expandable suture capture component is disposed within the elongated body. The expandable suture capture component is expanded to a deployed configuration in which the expandable suture capture component radially expands and extends away from the elongated body, wherein the expanded expandable suture capture component is positioned within the vessel. At least one pair of needles of the suturing device is distally extended from a loaded position in which the at least one pair of needles is disposed within the elongated body to a deployed position in which the at least one pair of needles distally extend from a distal end of the elongated body and penetrate through the vessel wall and through the expanded expandable suture capture component. A suture is slidingly disposed through the lumen of each needle and each suture is concurrently carried with its respective needle during the step of distally extending the at least one pair of needles to the deployed position.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3A is a sectional view of FIG. 3 taken along line A-A.

FIG. 3B is a cross-sectional view of FIG. 3 taken along line B-B.

FIG. 4 is a side view illustration of a first step of a method of using the suturing device of FIG. 3 according to an embodiment hereof, wherein the suturing device is advanced towards an arteriotomy.

FIG. 4A is a sectional view of a proximal portion of handle of the suturing device of FIG. 3, wherein the handle portion includes actuation mechanisms for deploying the needles and sutures with the actuation mechanisms being shown in a first or loaded position.

FIG. 4B is a sectional view of a distal portion of handle of the suturing device of FIG. 3, wherein the handle portion includes actuation mechanisms for deploying the suture snags and the actuation mechanisms are shown in a retracted position.

FIG. 6B is a sectional view of a distal portion of the suturing device of FIG. 3, wherein the suture snags of the suturing device are deployed.

FIG. 6C is a perspective view of a suture snag of FIG. 3 removed from the suturing device for illustrative purposes only, wherein the suture snag is in a deployed position.

FIG. 15B is an enlarged sectional view of a proximal portion of the handle of FIG. 15 illustrating an actuation mechanism for deploying the needles and the sutures associated therewith.

FIG. 15C is a perspective top view of the actuation mechanism of FIG. 15B, wherein the housing of the handle is shown in phantom.

FIG. 15D is a sectional view taken along line D-D of FIG. 15B.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of an arteriotomy, which is used herein to refer to an opening, cut, or incision of an artery, the invention may also be used in any other blood vessels or body passageways where it is deemed useful. For example, the device could be used to suture openings or incisions of other tissue such as a patent ductus arteriosus, a patent foramen ovale, a heart defect, a puncture wound, and the like. Furthermore, there is no intention to be bound by any expressed or implied theory presented in the preceding technical field, background, brief summary or the following detailed description.

Figure 12:
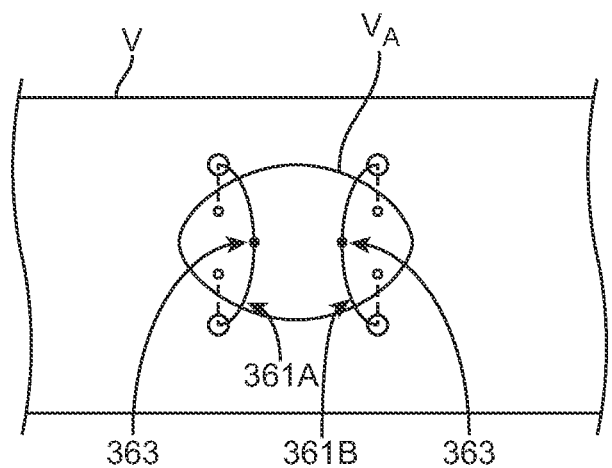
FIG. 12 is a top view illustration of another step of a method of use according to an embodiment hereof, wherein sutures having ends fastened together extend through the vessel wall around the arteriotomy.
Figure 13:
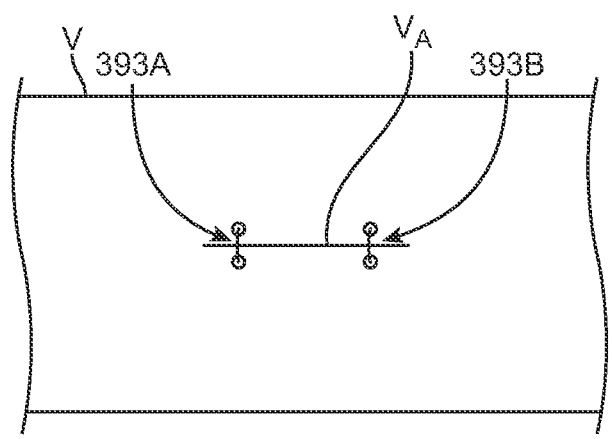
FIG. 13 is a top view illustration of another step of a method of use according to an embodiment hereof, wherein tension applied to the coupled sutures closes the arteriotomy.
Figure 14:
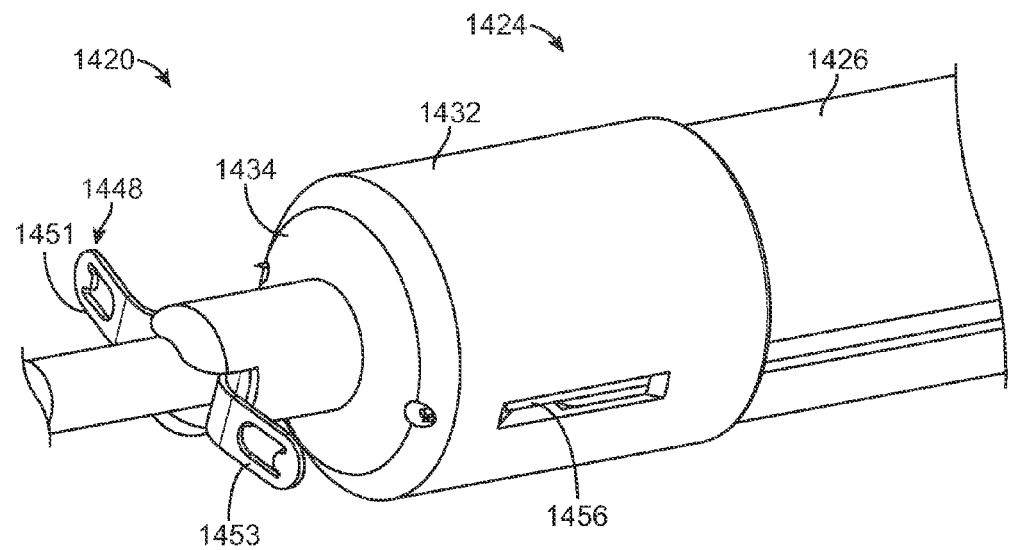
FIG. 14 is a perspective view of a distal end of a suturing device according to another embodiment hereof, wherein the suturing device includes only a single suture snag and a pair of needles for positioning a pair of sutures.
Figure 15:
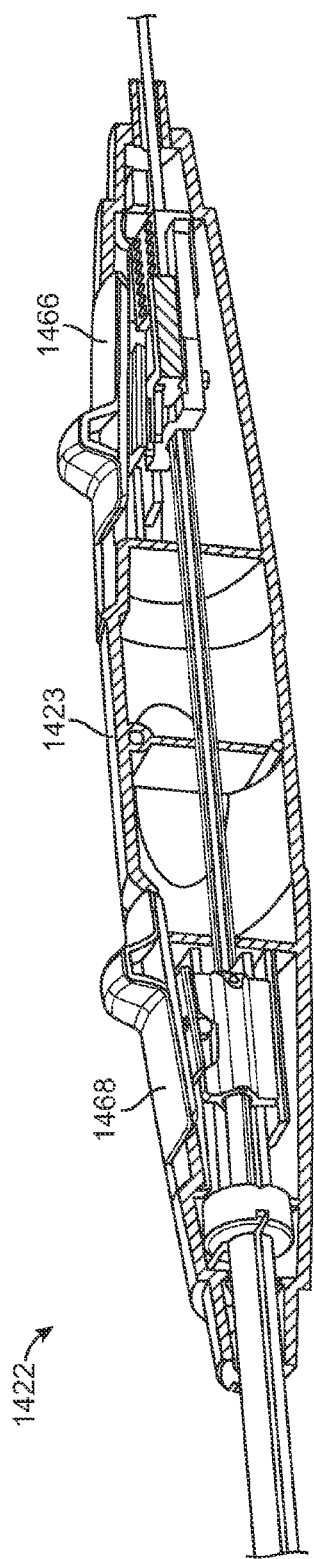
FIG. 15 is a sectional view of a handle of the suturing device of FIG. 14.

Suturing devices according to embodiments hereof use a pair of needle to position a pair of sutures beyond the boundaries or perimeter of an arteriotomy and then utilize a suture snag to capture the ends of the sutures and pull the suture ends back into the suturing device. The captured sutures are then tied together to form a single stitch. The suturing devices may be used to seal a blood vessel during and/or following an interventional catheterization procedure. As will be understood by one of ordinary skill in the art, the number of suture snags and needles may vary depending upon the number of sutures being positioned by the suturing device. For instance, one suture snag and one pair of needles are utilized for positioning one pair of sutures at an arteriotomy, whereby the suture pair is then tied together to form a single stitch, while two suture snags and two pairs of needles are utilized for positioning two pairs of sutures at an arteriotomy, whereby each suture pair is then tied together to form a total of two stitches. During delivery thereof, a first suture of a suture pair is housed within a first needle of a needle pair and a second suture of the suture pair is housed within a second needle of the needle pair. The first and second needles of the needle pair actuate or move together. Thus, a plurality of needles with a complementing number of suture snags may be incorporated into the device to accomplish the specific needs of the application. The embodiment of FIGS. 3-13 illustrate a suturing device for positioning two suture pairs for forming a total of two stitches at an arteriotomy while the embodiment of FIGS. 14-15 illustrate a suturing device for positioning one suture pair for forming a single stitch at an arteriotomy.

More particularly, a suturing device 320 for suturing arterial vessel walls and other biological tissue is shown in FIGS. 3-13. With initial reference to FIGS. 3, 3A, and 3B, suturing device 320 according to one embodiment includes first and second needle pairs 356A, 356B and first and second suture snags 348A, 348B for positioning and capturing respective ends of first and second suture pairs 360A, 360B beyond the boundaries of the arteriotomy. Suturing device 320 includes an inner or guidewire shaft 340 as well as suture pairs 360A, 360B extending proximally from a handle 322 and an elongated body 324 extending distally from handle 322. Handle 322 includes first and second sliders or actuators 366A, 366B which are utilized to extend needle pairs 356A, 356B, respectively, and suture pairs 360A, 360B, respectively, as will be described in more detail herein, and third and fourth sliders or actuators 368A, 368B which are utilized to deploy suture snags 348A, 348B, respectively, as will be described in more detail herein. More particularly, first suture pair 360A and first needle pair 356A are independently deployed or controlled by first actuator 366A of a first needle and suture pair actuation mechanism of handle 322, and second suture pair 360B and second needle pair 356B are independently deployed or controlled by opposing second actuator 366B of a second needle and suture pair actuation mechanism of handle 322. As such, a user may choose to deploy only one needle pair within a vessel at a time, for example when the vessel is of a relatively smaller size, or may choose to deploy both needle pairs simultaneously. In addition, each actuator 366A, 366B and corresponding actuation mechanism is provided for the deployment of two components, i.e., a pair of needles and the respective suture pair held thereby, which is beneficial for ease of use.

Elongated body 324 includes an outer shaft 326 and a distal guiding component 332 which is disposed over and coupled to a distal portion of outer shaft 326. Distal guiding component 332 may be coupled to outer shaft 326 by adhesive or a threaded connection, or may be unitary or integral with the outer shaft. A distal end of distal guiding component 332 defines the distal end of elongated body 324. Each of the outer shaft and the distal guiding component are hollow tubular components and collectively define at least one continuous lumen 328 through elongated body 324 for housing two elongated transmission members 370A, 370B and inner shaft 340, as shown in the sectional view of FIG. 3B. As will be explained in more detail herein, transmission members 370A, 370B extend between third and fourth actuators 368A, 368B, respectively, and suture snags 348A, 348B, respectively, and function as actuation mechanisms for the suture snags because they interact with third and fourth actuators 368A, 368B, respectively, in the deployment and retraction of the suture snags. Inner shaft 340 extends through handle 332 to a tapered distal tip or nosecone 346, which is coupled to a distal end portion 345 (shown in FIG. 4D) of inner shaft 340. Inner shaft 340 and distal tip 346 may define a continuous lumen 342 for tracking suturing device 320 over a guidewire (not shown). As shown in the sectional view of FIG. 3A, a hemostasis seal 325 is disposed with handle 322 around inner shaft 340 adjacent to a proximal end of outer shaft 326.

Since suturing device 320 is utilized to place the sutures around the border or edge of an arteriotomy of a vessel, the components of the suturing device will be described while simultaneously describing a method of using the suturing device to position suture pairs 360A, 360B in situ with reference to FIGS. 4-13. Referring to FIG. 4, a side view of a distal end portion of suturing device 320 having suture pairs 360A, 360B loaded therein is shown being distally advanced over a guidewire GW towards an arteriotomy $V_A$ in the vessel wall $V_W$ of a vessel. In an embodiment, each suture of suture pairs 360A, 360B is a continuous strand or filament of material having a first end 362A, 362B, respectively (see FIG. 4E) and a second end 364A, 364B, respectively (see FIG. 3). Exemplary suture materials include but are not limited to a monofilament or plastic suture material, such as polypropylene. Suturing device 320 is in a delivery configuration, in which suture snags 348A, 348B are in a retracted position while needles pairs 356A, 356B and suture pairs 360A, 360B are in a loaded position.

Figure 1:
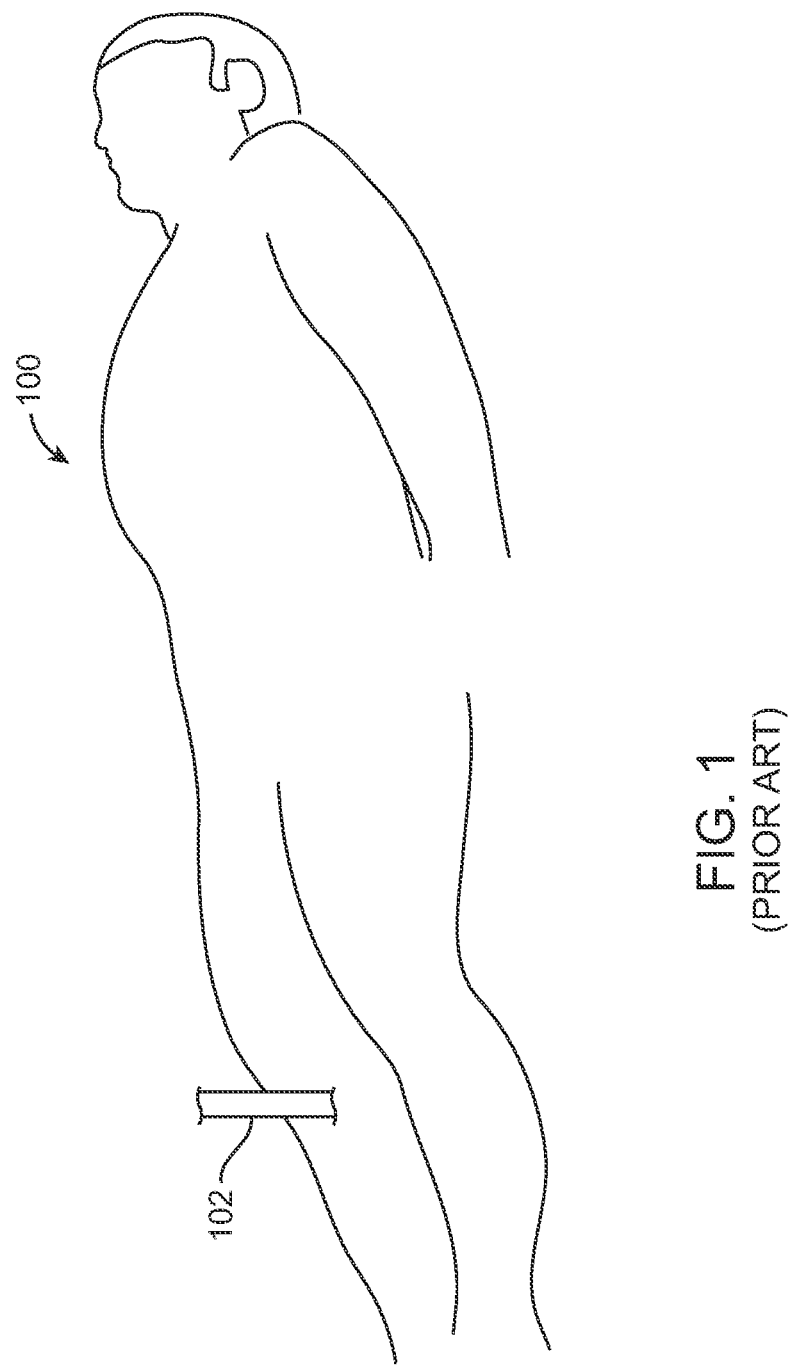
FIGS. 1 and 2 illustrate the introduction of an introducer sheath into the vasculature via the femoral artery, thereby forming an arteriotomy in a vessel wall of the femoral artery.
Figure 2:
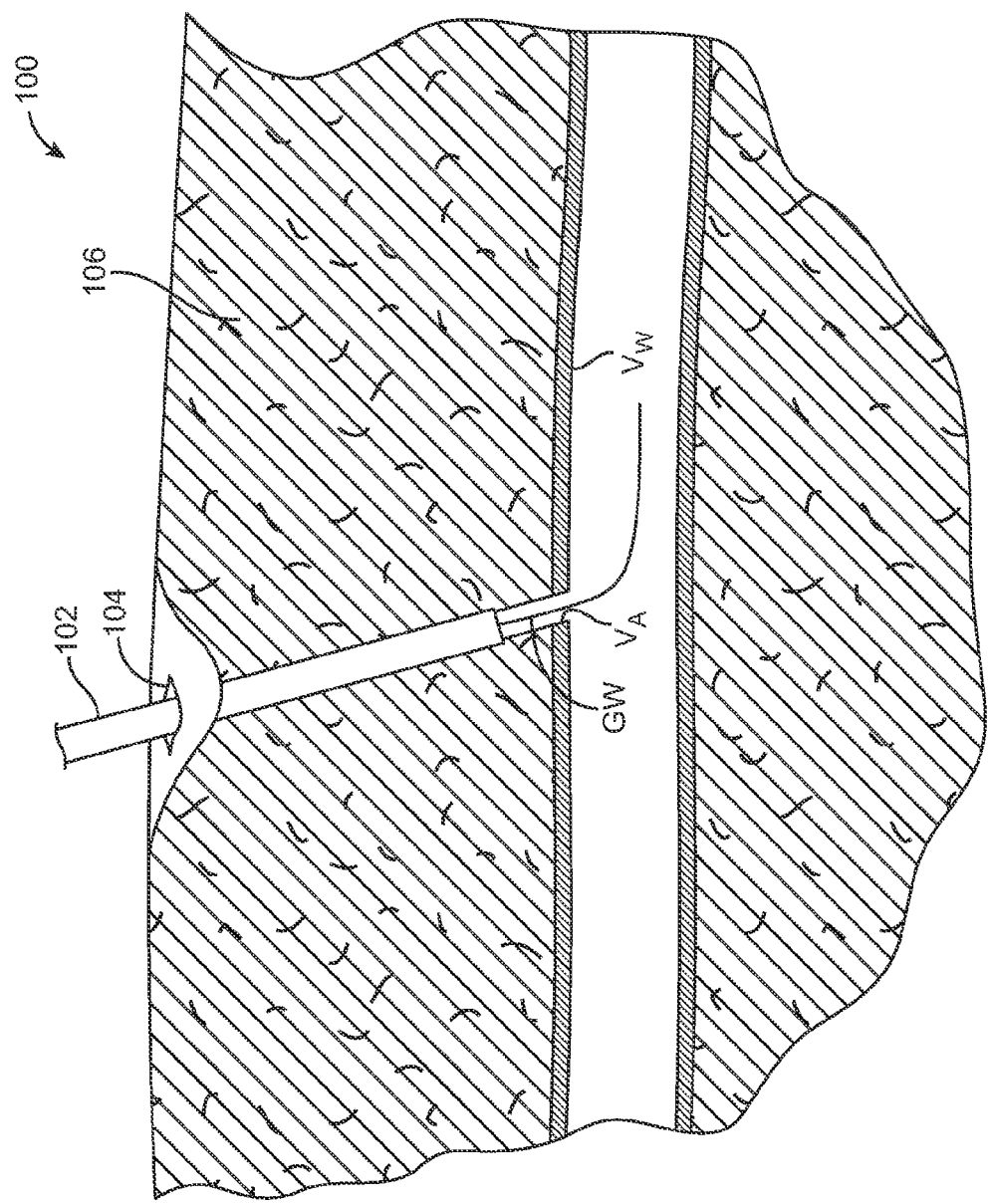
Figure 3:
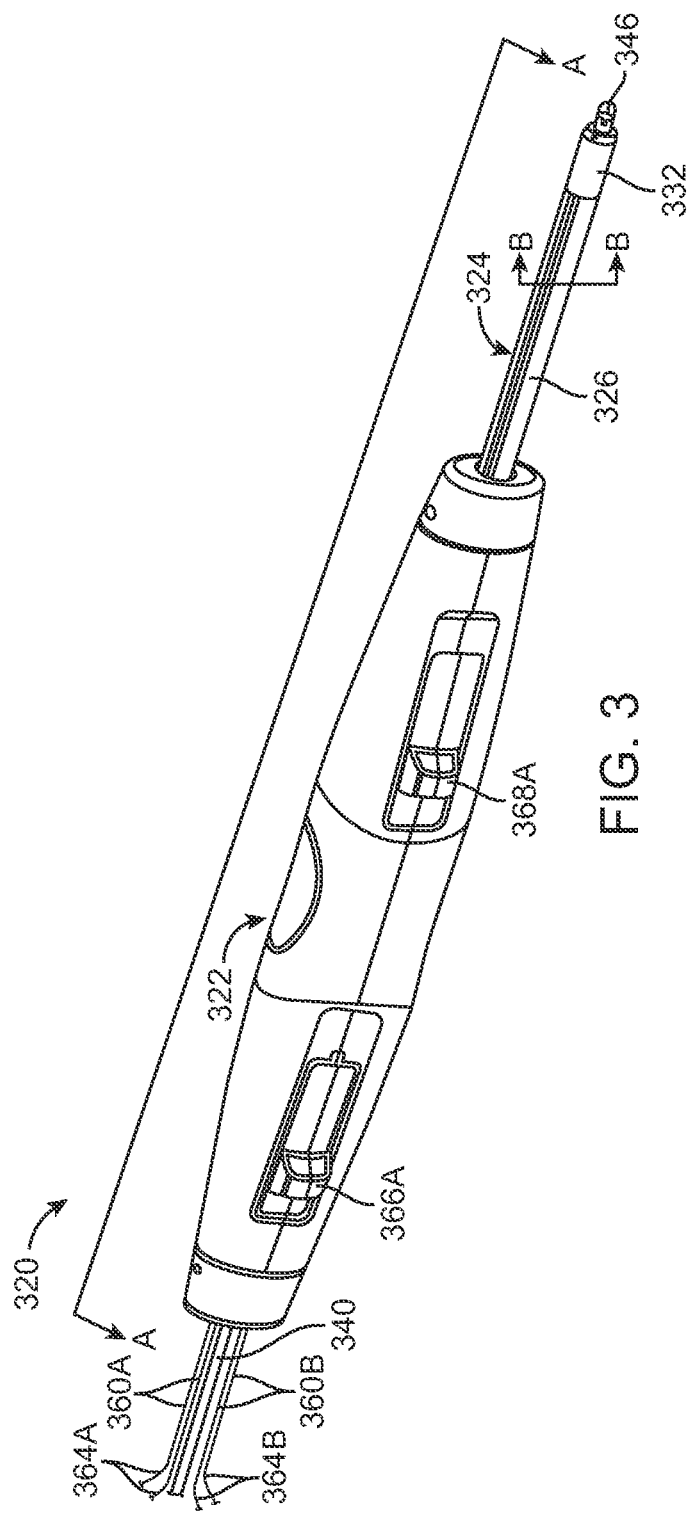
FIG. 3 is a perspective view of a suturing device according to an embodiment hereof for sealing or closing an arteriotomy, wherein the suturing device is in a delivery configuration in which the suture snags are in a retracted position and the needles and sutures are in a loaded position.
Figure 4C:
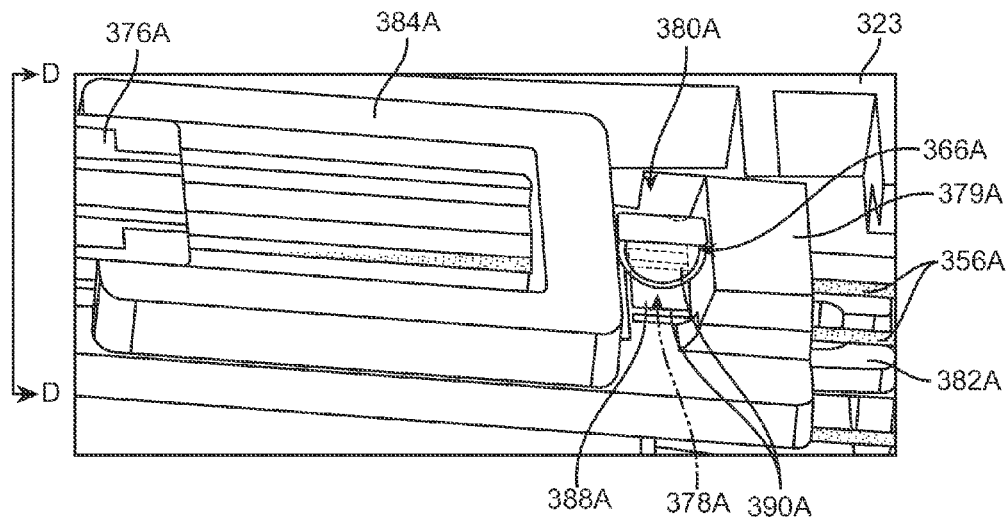
FIG. 4C is a cutaway view of a proximal portion of the handle of the suturing device of FIG. 3 exposing an actuation mechanism for deploying the needles and sutures.
Figure 4D:
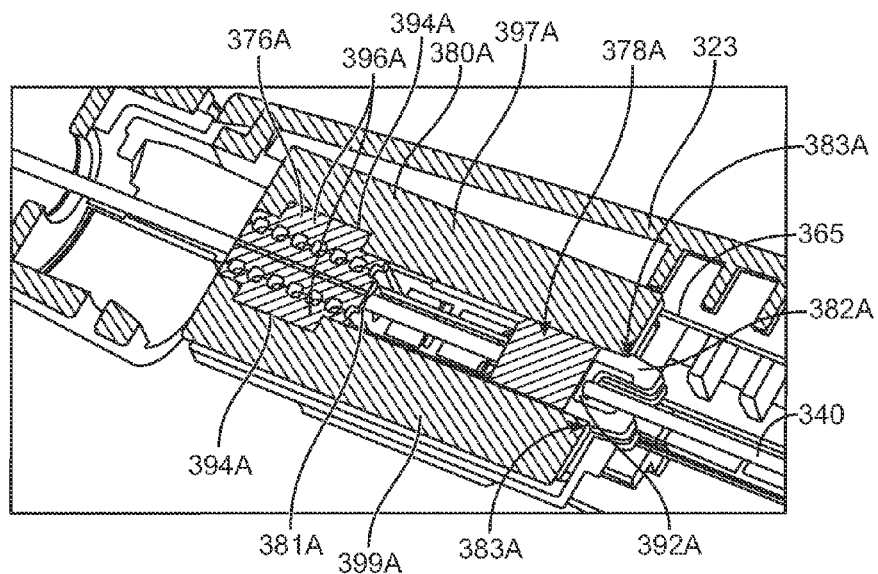
FIG. 4D is a sectional view taken along line D-D of FIG. 4C.
Figure 4E:
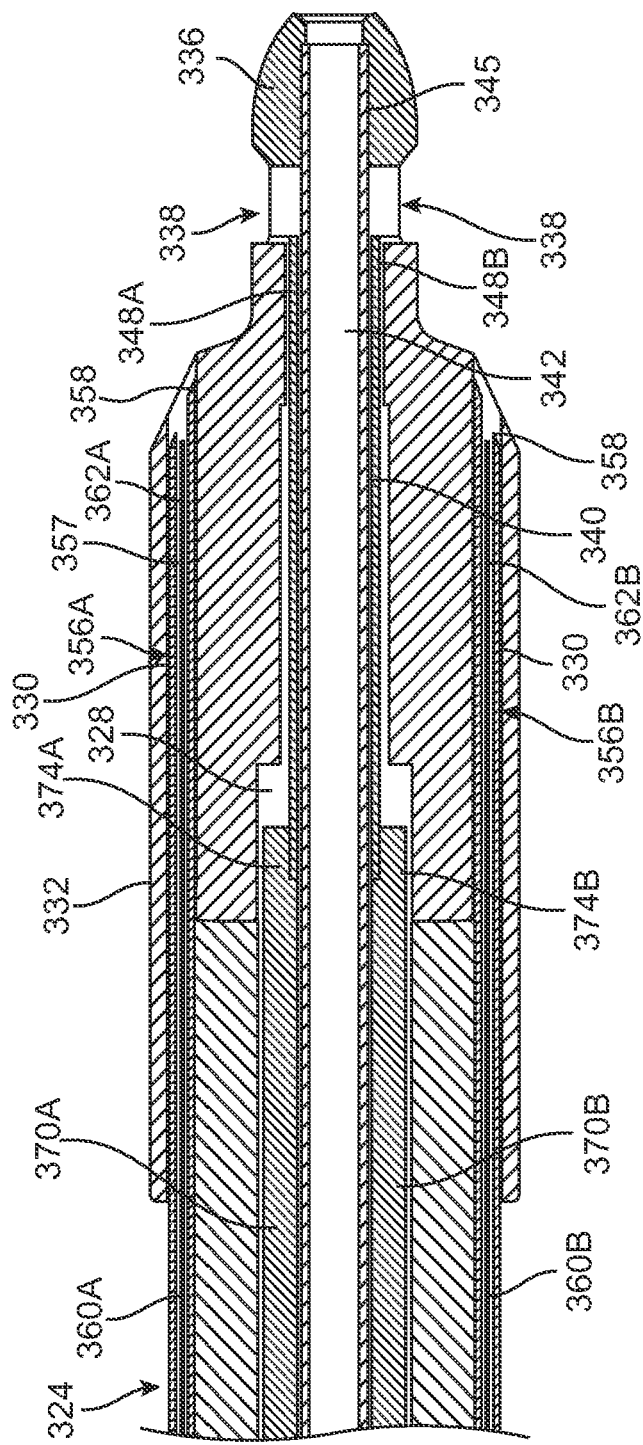
FIG. 4E is a sectional view of a distal portion of the suturing device of FIG. 3, wherein the suture snags are in the retracted position and the needles and sutures are in the loaded position.
Figure 4F:
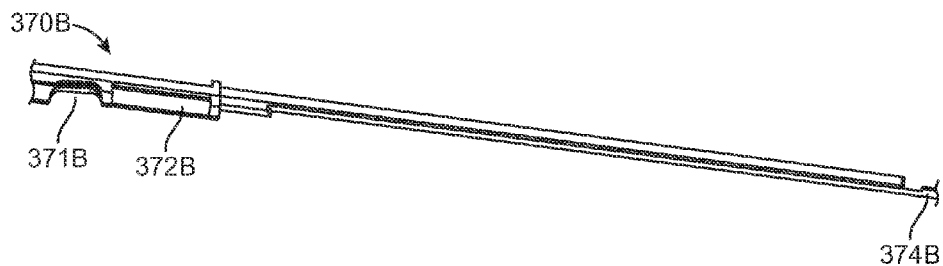
FIG. 4F is a perspective view of a transmission member of the suturing device of FIG. 3, wherein the transmission member is removed from the suturing device for illustrative purposes only.
Figure 4G:
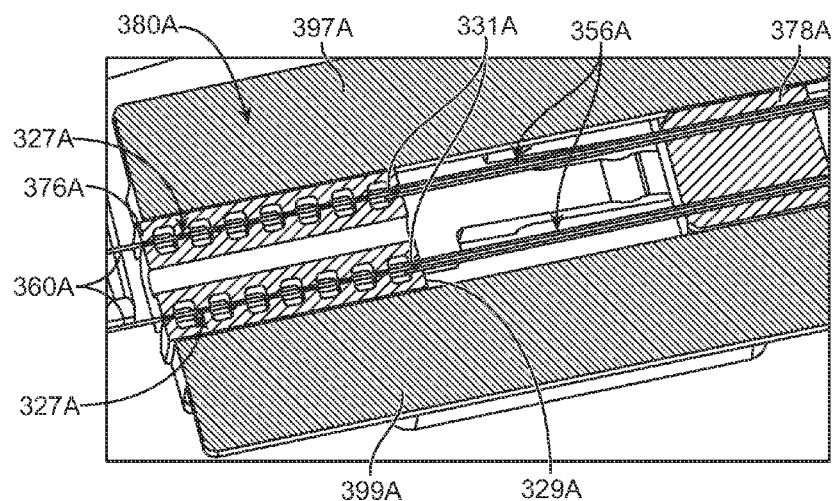
FIG. 4G is a sectional view taken along line G-G of FIG. 4D.

More particularly, as shown in the sectional view of FIG. 4E, two suture snags 348A, 348B in the collapsed or retracted position are located or housed in lumen 328 of elongated body 324 and are substantially parallel to a longitudinal axis of elongated body 324. Suture snags 348A, 348B are disposed within distal guiding component 332 during delivery of suturing device 320 so that they do not catch on the vessel walls of the vasculature during insertion and removal of the suturing device. Suture snags 348A, 348B are deployed by third and fourth actuators 368A, 368B, respectively, on handle 322 that interact with respective suture snag actuation mechanisms within handle 322 comprised of transmission members 370A, 370B. Suture snags 348A, 348B are coupled to the actuators via transmission members 370A, 370B, respectively. With additional reference to FIG. 4B which is a sectional view of handle 322 at actuators 368A, 368B and FIG. 4F which is a perspective view of transmission member 372B removed from the suturing device for illustrative purposes only, proximal ends 372A, 372B of transmission members 370A, 370B are located adjacent to actuators 368A, 368B, respectively, while distal ends 374A, 374B of transmission members 370A, 370B are attached or connected to suture snags 348A, 348B, respectively. In another embodiment hereof (not shown), transmission members 370A, 370B may be integrally formed with suture snags 348A, 348B.

Proximal ends 372A, 372B of transmission members 370A, 370B each include a recess or groove 371A, 371B, respectively, that form proximal surfaces 375A, 375B and distal surfaces 373A, 373B, respectively. When it is desired to deploy suture snag 348A, actuator 368A is slid forward or distally advanced such that a knob or boss 369A thereof slides or moves within recess 371A until it abuts against distal surface 373A and pushes or distally advances transmission member 370A, thereby also pushing or distally advancing suture snag 348A. Similarly, when it is desired to deploy suture snag 348B, actuator 368B is slid forward or distally advanced such that a knob or boss 369B thereof slides or moves within recess 371B until it abuts against distal surface 373B and pushes or distally advances transmission member 370B, thereby also pushing or distally advancing suture snag 348B. In the delivery configuration of the suturing device shown in FIGS. 4B and 4E, suture snags 348A, 348B are both in a retracted position with bosses 369A, 369B of actuators 368A, 368B, respectively, abutting against proximal surfaces 375A, 375B of recesses 371A, 371B of transmission members 370A, 370B, respectively. In addition, actuators 368A, 368B also abut against stops 359A, 359B, respectively, of a housing 323 of the handle 322 that project or protrude radially to limit proximal retraction of actuators 368A, 368B.

FIG. 4E also illustrates the loaded position of needles pairs 356A, 356B and suture pairs 360A, 360B. Each needle is a generally straight tubular shaft component or hypotube which defines a lumen 357 for slidingly receiving a suture and includes a distal end 358 configured to penetrate or pierce through the vessel wall. During delivery, a first suture of first suture pair 360A has a distal length disposed within a first needle of needle pair 356A and a second suture of first suture strand pair 360A has a distal length disposed within a second needle of needle pair 356A, wherein distal ends of the first and second sutures do not extend from the distal ends of their respective needles. Similarly, a first suture of second suture pair 360B has a distal length disposed within a first needle of needle pair 356B and a second suture of second suture pair 360B has a distal length disposed within a second needle of needle pair 356B, wherein distal ends of the first and second sutures do not extend from the distal ends of their respective needles. Each of the sutures of suture pairs 360A, 360B has a proximal length that extends proximally of handle 322 to be accessible to a clinician as described in more detail below. Outer shaft 326 and distal guiding component 332 collectively define or include a plurality of needle pathways or guides 330 for housing needle pairs 356A, 356B, which are slidingly disposed thereon or therein. With reference to the cross-sectional view of FIG. 3B, needle guides 330 may be formed via channels or grooves formed on an exterior surface of outer shaft 326 that mate with a plurality of lumens formed through distal guiding component 332. Alternatively, rather than channels or grooves formed on the outer surface thereof, outer shaft 326 may define individual lumens for housing each needle.

Needle pair 356A and suture pair 360A are deployed by actuator 366A that interact with a first needle and suture actuation mechanism within handle 322 comprised of a suture holder 376A, a needle holder 378A, and a carriage 380A. An identical second needle and suture actuation mechanism comprised of a needle holder 378B, a suture holder 376B, and a carriage 380B within handle 322 is utilized to deploy needle pair 356B and suture pair 360B via interaction with actuator 366B. In FIG. 4A, needle pairs 356A, 356B and suture pairs 360A, 360B are each in a loaded position, with suture pairs 360A, 360B disposed within their respective needle pair 356A, 356B. With reference to FIGS. 4A, 4C, and 4D, needle pair 356A is coupled to needle holder 378A and needle pair 356B is coupled to needle holder 378B. The needle pairs may be coupled to the respective needle holder via adhesive or other bonding mechanism. Similarly, when in the loaded position, suture pair 360A is coupled to a suture holder 376A which is formed of a resilient material such as silicone. As best shown in the sectional view of FIG. 4G, in the loaded position of the needle pairs and the suture pairs, proximal ends 331A of needle pair 356A are located within a portion of longitudinal slits 327A of suture holder 376A, adjacent to a distal end 329A of suture holder 376A, but at this stage of deployment the needle pair 365A does not extend through the suture holder. In order to couple each suture of suture pair 360A to suture holder 376A, each suture of suture pair 360A extends proximally from a respective proximal end 331A of needle pair 356A and extends through a respective longitudinal slit 327A of suture holder 376A. When suture holder 376A is distally advanced first with needle holder 378A during deployment of needle pair 365A and second decoupled from needle holder 378A during deployment of suture pair 360A, each suture of suture pair 360A is essentially squeezed or held via an interference fit within its respective slit 327A of suture holder 376A and therefore is distally advanced or carried by suture holder 376A. Suture pair 360B is similarly coupled to a suture holder 376B which is obscured from the views of FIGS. 4A, 4C, and 4D but may be seen in FIG. 8D.

In the delivery configuration of the suturing device, suture holder 376A and needle holder 378A are both coupled to a shuttle or carriage 380A of the actuation mechanism. As will be explained in more detail herein, actuator 366A pushes or distally advances carriage 380A in order to first extend or deploy needle pair 356A (via needle holder 378A coupled to carriage 380A) from the suturing device while carrying suture pair 360A loaded therein, and thereafter to extend or deploy suture pair 360A (via suture holder 376A which is also coupled to carriage 380A) relative to and distal of needle pair 356A. Similarly, in the delivery configuration of the suturing device, suture holder 376B and needle holder 378B are both coupled to a shuttle or carriage 380B, and actuator 366B pushes or distally advances carriage 380B in order to extend or deploy first needle pair 356B and then suture pair 360B. Needle holder 378A, suture holder 376A, carriage 380A, and actuator 366A are mirror images of needle holder 378B, suture holder 376B, carriage 380B, and actuator 3668, respectively, and as such, interactions of the actuation mechanism of needle holder 378A, suture holder 376A, and carriage 380A with actuator 366A is described herein.

More particularly, carriage 380A includes a first leg 397A, a second leg 399A, which extends substantially parallel but spaced apart from first leg 397A, and a distal bridge 379A, which extends between the distal ends of first and second legs 397A, 399A. Each leg 397A, 399A rides or slides along a track 365 of housing 323 of handle 322. Track 365 projects radially inward from the housing of the handle, and carriage 380A rides or slides along the track as it is distally advanced during extension of needle pair 356A and/or suture pair 360A as will be explained in more detail herein. Suture holder 376A is positioned within a proximal portion of carriage 380A, to be sandwiched between first and second legs 397A, 399A thereof, and is coupled to carriage 380A via integrally formed protrusions 396A of suture holder 376A which extend into corresponding recesses 394A of first and second legs 397A, 399A. Since suture holder 376A is coupled to carriage 380A, carriage 380A essentially pulls or carries suture holder 376A, and thus suture pair 360A attached thereto, forward when carriage 380A is distally advanced via actuator 366A. Suture holder 376A includes a longitudinal channel or groove 381A (see FIG. 4D) formed on an inner surface thereof for sliding or riding along inner shaft 340A.

Needle holder 378A includes a distal portion having claws or prongs 382A, a U-shaped proximal portion 384A, and an intermediate portion 388A extending therebetween. Intermediate portion 388A includes a pair of channels or grooves 390A formed on an outer surface thereof for receiving respective needles of needle pair 356A and also includes a channel or groove 392A (see FIG. 4D) formed on an inner surface thereof for sliding or riding along inner shaft 340A. In a delivery configuration of the suturing device, needle holder 378A is coupled to carriage 380A via mating or bearing surfaces 383A (see FIG. 4D). As a result of the interference fit between needle holder 378A and carriage 380A at bearing surfaces 383A, carriage 380A pushes or carries needle holder 378A, and thus needle pair 356A attached thereto, forward, i.e., in a distal direction, when carriage 380A is distally advanced via actuator 366A.

Figure 5:
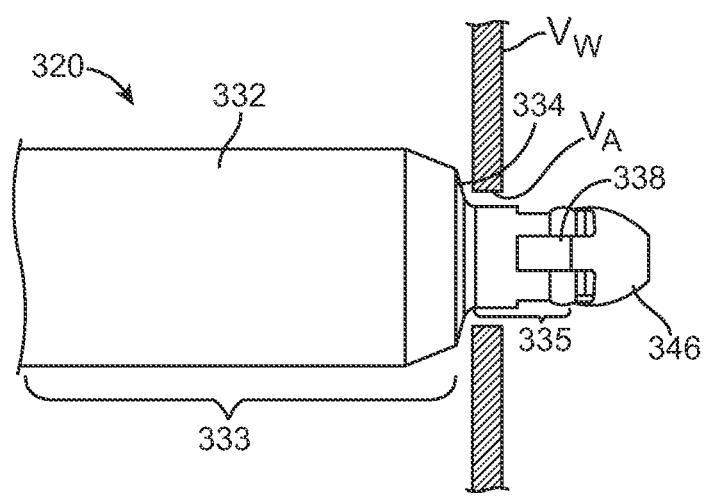
FIG. 5 is a side view illustration of a second step of the method of using the suturing device of FIG. 3 according to an embodiment hereof, wherein the suturing device is positioned through the arteriotomy.

Referring to FIG. 5, suturing device 320 is shown advanced to a position in which a distal portion thereof is positioned through a target arteriotomy $V_A$ such that distal tip 346 is disposed within a lumen of the vessel. Suturing device 320 is still in a delivery configuration, in which suture snags 348A, 348B are in a retracted position and needle pairs 356A, 356B and suture pairs 360A, 360B are in a loaded position as described above with respect to FIG. 4. Distal guiding component 332 includes a stepped or tapered region which creates an abutment surface 334. The outer diameter of a proximal portion 333 of distal guiding component 332, i.e., a portion which is proximal to abutment surface 334, is greater than the outer diameter of a distal portion 335 of distal guiding component 332, i.e., a portion which is distal to abutment surface 334. For example, the outer diameter of proximal portion 333 of distal guiding component 332 may be between 15 and 20 French while the outer diameter of distal portion 335 of distal guiding component 332 may be between 8 and 12 French. As shown in FIG. 5, distal portion 335 of distal guiding component 332 is sized to protrude through the arteriotomy $V_A$ and extend into the lumen of the vessel, while proximal portion 333 of distal guiding component 332 is sized to abut against the outer surface of the vessel wall $V_W$ and not protrude or extend through the arteriotomy $V_A$ and into the lumen of the vessel. When the user is advancing suturing device 320 to the arteriotomy $V_A$, a resistance to further advancement is felt when abutment surface 334 contacts the vessel wall, thereby notifying the user that the suturing device is in place within the arteriotomy $V_A$ as desired.

Figure 6:
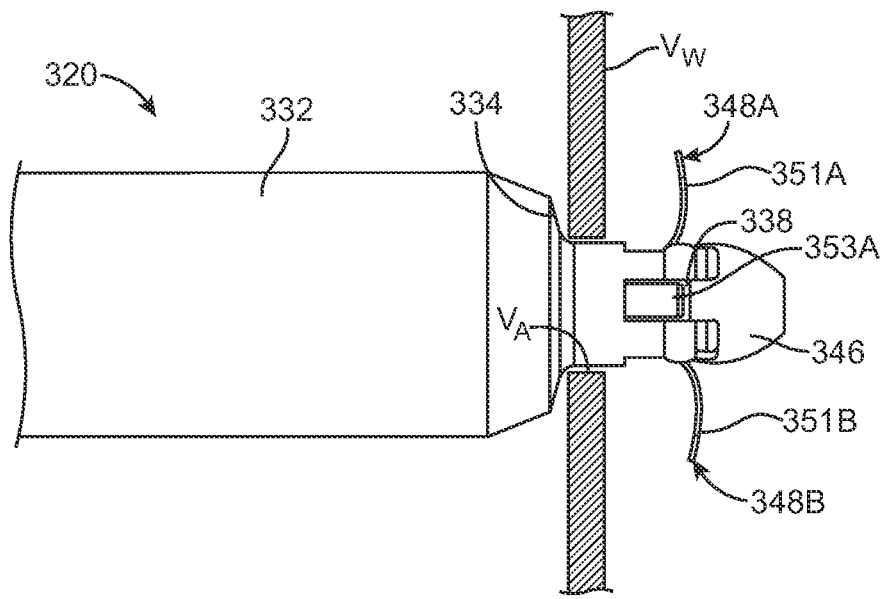
FIG. 6 is a side view illustration of a third step of the method of using the suturing device of FIG. 3 according to an embodiment hereof, wherein suture snags of the suturing device are deployed.

Once the distal portion of distal guiding component 332 is positioned through the arteriotomy $V_A$ of the vessel to reside within the lumen of the vessel, suture snags 348A, 348B are deployed against the vessel wall $V_W$ around the arteriotomy $V_A$ of the vessel as shown in FIG. 6. For illustrative purposes, suture snag 348A is shown in FIG. 6C in a deployed configuration removed from the suturing device. Suture snag 348B is identical to suture snag 348A and thus only the structure of suture snag 348A is described herein. Suture snag 348A includes two arms 350A, 352A which are disposed at an angle of approximately 90 degrees relative to each other. "Approximately" as utilized herein includes a range of plus or minus ten degrees. The proximal ends of arms 350A, 352A are joined via a connector 354A. Distal ends 374A, 374B of transmission members 370A, 370B may fit within a space or gap 337 between arms 350A, 352A to thereby couple transmission members 370A, 370B to suture snag 348A, although other mechanisms for coupling the transmission members and the suture snags may be used. When suturing device 320 is being delivered, arms 350A, 352A are generally straight. However, in the deployed configuration shown in FIG. 60, distal arm portions 351A, 353A of each arm 350A, 352A, respectively, curve or extend radially outward from a longitudinal axis of the suturing device because at least distal arm portions 351A, 353A are formed from a resilient material having a mechanical memory. Mechanical memory may be imparted by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. Distal arm portions 351A, 353A of suture snag 348A each include a thru-hole or aperture 355 there through. Aperture 355 is generally circular or elliptical but includes two radial extensions 339 of the aperture or hole that function to catch or grip the ends of the suture as will be described in more detail herein. As will be shown in an additional embodiment described herein, if a single needle pair and a single suture snag are included on a suturing device to deploy a single suture pair, the distal arm portions of the suture snag are circumferentially spaced at approximately 180 degrees from each other. However, when two suture snags are included on a suturing device such as suturing device 320, the distal arm portions of each suture snag are circumferentially spaced approximately 90 degrees from each other.

Figure 6A:
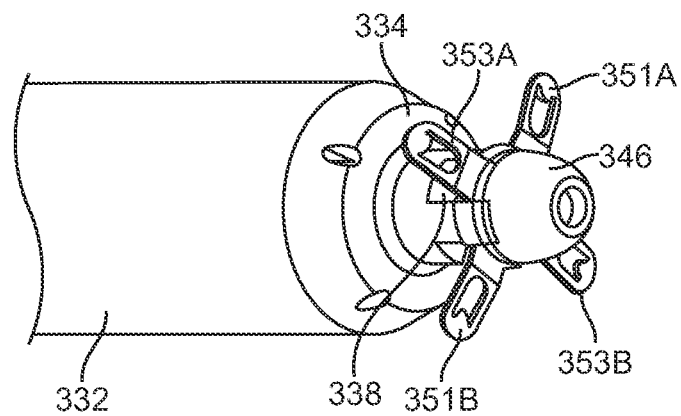
FIG. 6A is a perspective view of a distal portion of the suturing device of FIG. 3, wherein the suture snags of the suturing device are deployed.
Figure 6D:
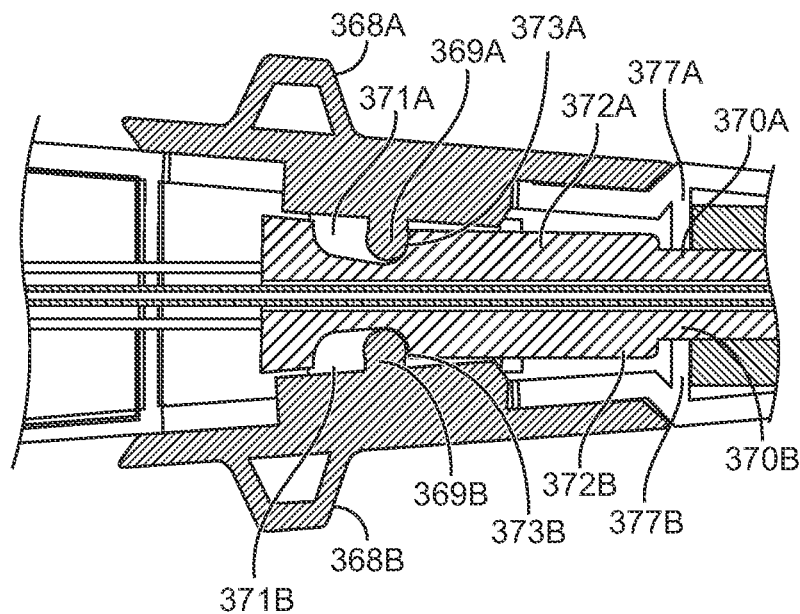
FIG. 6D is a sectional view of a distal portion of the handle of the suturing device of FIG. 3 with the actuation mechanisms for deploying the suture snags shown in a deployed position.
Figure 6E:
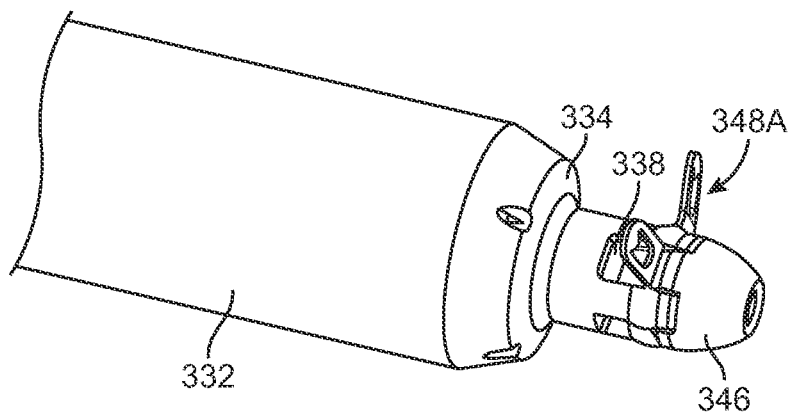
FIG. 6E is a perspective view of a distal portion of the suturing device of FIG. 3, wherein only one suture snag of the suturing device is deployed.

Distal guiding component 332 includes four passageways or openings 338 formed at a distalmost end thereof which allow the distal arm portions of the two suture snags 348A, 348B to alternate between the retracted position during delivery in which each suture snag 326 is disposed within and is substantially parallel to elongated body 324, as shown and described above with respect to FIGS. 4 and 5, and a second deployed position in which the distal arm portions of each suture snag 348A, 348B extend radially outward from openings 338 away from the elongated body, as shown in FIGS. 6, 6A, and 6B. With reference to FIG. 6D which is a sectional view of handle 322 at actuators 368A, 368B, when it is desired to deploy suture snag 348A, actuator 368A is distally advanced such that boss 369A thereof abuts against distal surface 373A and pushes or distally advances transmission member 370A, thereby also pushing or distally advancing distal arm portions 351A, 353A of suture snag 348A out of two of the four openings 338 of distal guiding component 332. Similarly, when it is desired to deploy suture snag 348B, actuator 368B is distally advanced such that boss 369B thereof abuts against distal surface 373B and pushes or distally advances transmission member 370B, thereby also pushing or distally advancing distal arm portions 351B, 353B of suture snag 348B out of the other two of the four openings 338 of distal guiding component 332. It will be apparent to one of ordinary skill in the art that suture snags 348A, 348B may be deployed simultaneously or independently. FIGS. 6A and 6B illustrate both suture snags 348A, 348B deployed, while FIG. 6E illustrates only suture snag 348A deployed. When each suture snag 348A, 348B is distally advanced via actuator 368A, 368B, respectively, distal arm portions 351A, 353A, 351B, 353B extend out of openings 338 formed at a distalmost end of distal guiding component 332. The mechanical memory of each suture snag causes the distal arm portions 351A, 353A, 351B, 353B to assume their deployed configurations and radially extend. When deployed, distal arm portions 351A, 353A, 351B, 353B of suture snags 348A, 348B, respectively, lie adjacent to or against an inside surface of the vessel wall $V_W$ with respective apertures 355 thereof positioned radially outward of the arteriotomy $V_A$. FIG. 6D illustrates actuators 368A, 368B when both suture snags 348A, 348B are in a deployed position with bosses 369A, 369B of actuators 368A, 368B, respectively, abutting against distal surfaces 373A, 373B of recesses 371A, 371B of transmission members 370A, 370B, respectively. Proximal ends 372A, 372B of transmission members 370A, 370B, respectively, abut against stops 377A, 377B, respectively, of housing 323 of handle 322 which project radially inward to limit distal advancement of actuators 368A, 368B.

Figure 7:
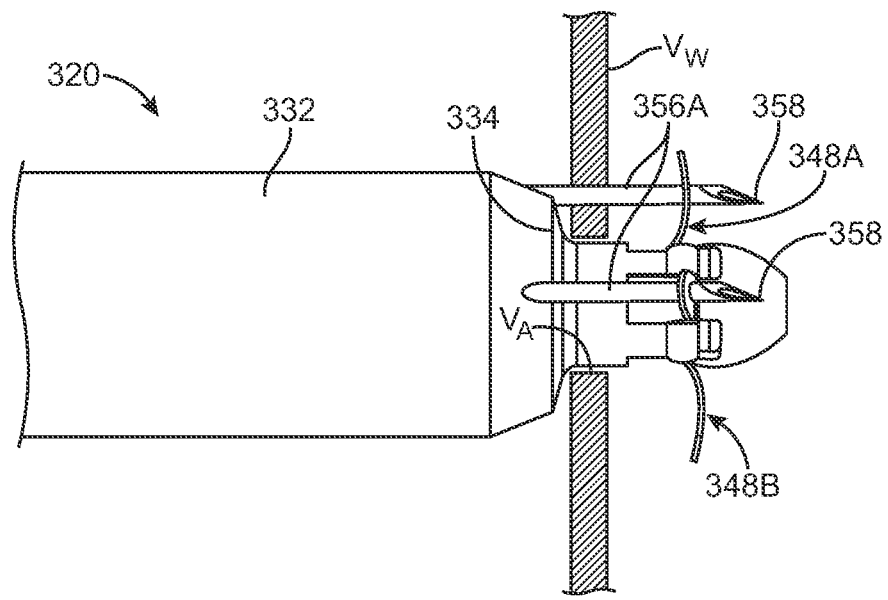
FIG. 7 is a side view illustration of a fourth step of the method of using the suturing device of FIG. 3 according to an embodiment hereof, wherein a pair of needles with sutures therein are deployed to extend through the vessel wall adjacent to the arteriotomy.
Figure 7A:
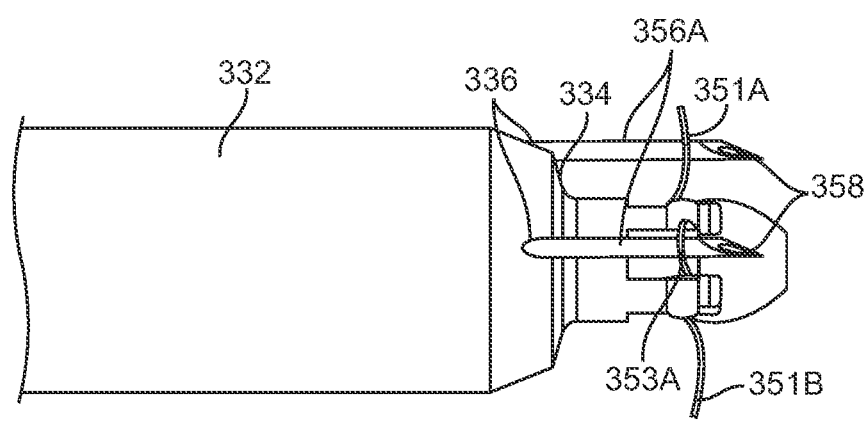
FIG. 7A is a perspective view of a distal portion of the suturing device of FIG. 3, wherein the needles with the sutures therein are deployed.

After suture snags 348A, 348B are deployed, needle pair 356A and suture pair 360A are distally advanced until the respective actuation mechanism has reached a needle deployment position wherein the needles pierce through the vessel wall $V_W$ at points that are radially outward of the arteriotomy $V_A$ as shown in FIG. 7. In one embodiment, as shown in FIGS. 7 and 7A, only needle pair 356A is first extended into a lumen of a vessel. Extending only one needle pair into the vessel at a time provides access to relatively smaller vessels. However, it will be understood that both needle pairs may alternatively be extended or deployed into the vessel wall at the same time. With additional reference to the perspective view of FIG. 7A, needle pair 356A is distally advanced out of distal ports 336 of distal guiding component 332 and is distally advanced through tissue around the arteriotomy of a vessel until distal ends 358 of the needles extend through apertures 355 of deployed suture snags 348A, 348B. Accordingly, in situ, needle pair 356A creates incisions or pathways within tissue around the arteriotomy during deployment. Although not visible in the views of FIGS. 7 and 7A, suture pair 360A extending within and carried with needle pair 356A is similarly distally advanced concurrently with needle pair 356A. Notably, since needle pair 356A is distally deployed out of the relatively larger proximal portion of distal guiding component 332, the needles extend straight out of ports 336 to pierce through the vessel wall $V_W$ and do not need to bend or curve. As such, the amount of force or energy required to extend the needles is minimized. Further, since no bending is required, the needles may be formed from stainless steel for improved pushability. In an embodiment, the outer diameter of the needles ranges between 0.015 and 0.025 inches, but needles with other diameters may be used herewith.

Figure 7B:
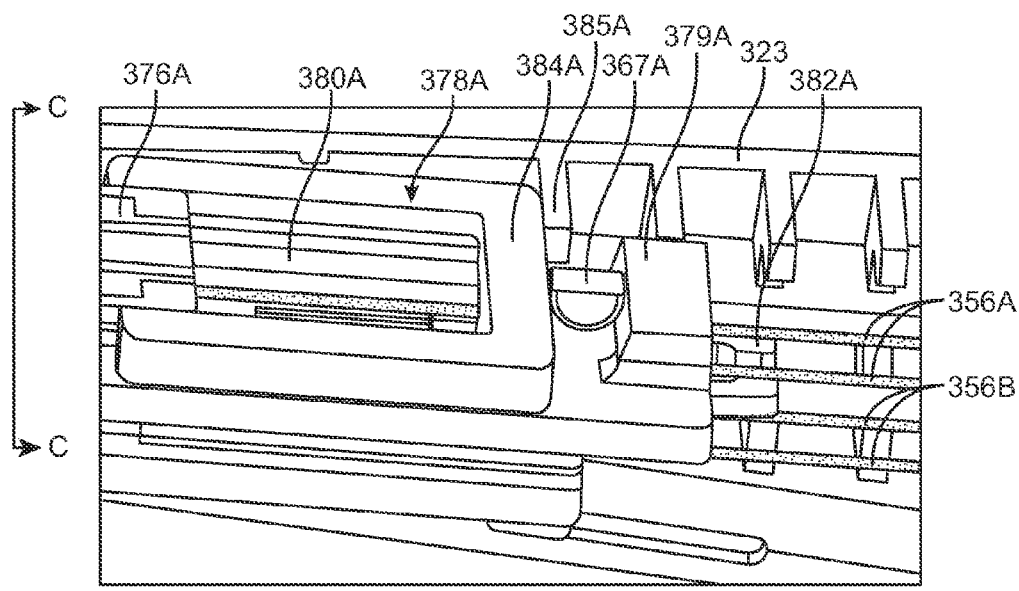
FIG. 7B is a cutaway view of a distal portion of the handle of the suturing device of FIG. 3 exposing actuation mechanisms for deploying the needles and sutures with the top actuation mechanism shown in a needle deployment position.

In order to extend needle pair 356A and suture pair 360A to the position shown in FIG. 7, actuator 366A on handle 322 is distally advanced until the actuation mechanism associated therewith reaches a needle deployment position. With reference to FIG. 7B which is a cutaway view of handle 322 at actuator 366A, a knob or boss 367A (shown in phantom) of actuator 366A is positioned proximal to and abuts against distal bridge 379A of carriage 380A. When actuator 366A is pushed forward or distally advanced, boss 367A pushes or distally advances carriage 380A, thereby also distally advancing in unison both suture holder 376A (and suture pair 360A coupled thereto) and needle holder 378A (and needle pair 356A coupled thereto). Since suture holder 376A is coupled to carriage 380A via protrusions 396A which mate with corresponding recesses 394A as described above, carriage 380A pulls or carries suture holder 376A, and thus suture pair 360A attached thereto, forward when carriage 380A is distally advanced via actuator 366A. In addition, since needle holder 378A is coupled to carriage 380A via an interference fit between bearing surfaces 383A as described above, carriage 380A pushes or carries needle holder 378A, and thus needle pair 356A attached thereto, forward when carriage 380A is distally advanced via actuator 366A. Needle holder 378A is carried by or moves concurrently with carriage 380A until U-shaped proximal portion 384A of the needle holder abuts against a stop 385A of housing 323 of handle 322, such that the needle deployment position has been reached as shown in FIG. 7B. Needle holder 378A, as well as needle pair 356A attached thereto, cannot be distally advanced after U-shaped proximal portion 384A of the needle holder abuts against stop 385A. As such, at this point in the method of use, needle pair 356A is in an extended deployed position while suture pair 360A may be considered to be in a partially extended position or as remaining in a loaded position within needle pair 356A.

Figure 7C:
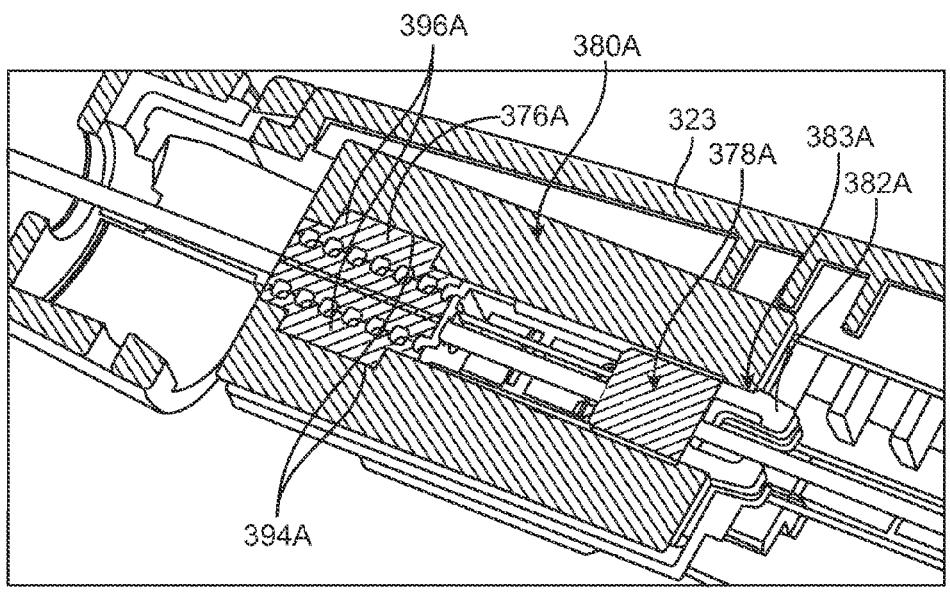
FIG. 7C is a sectional view taken along line C-C of FIG. 7B.
Figure 8:
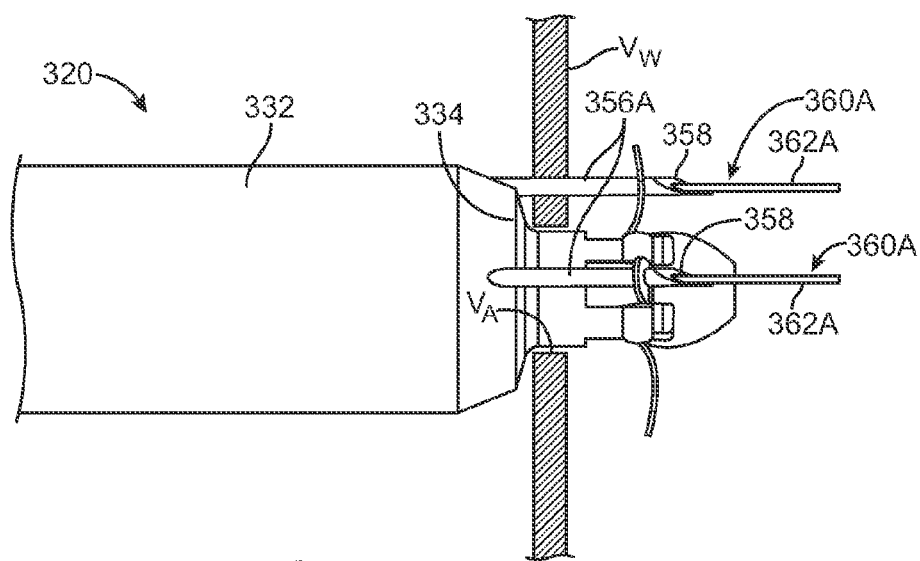
FIG. 8 is a side view illustration of a fifth step of the method of using the suturing device of FIG. 3 according to an embodiment hereof, wherein the sutures are deployed to extend beyond the distal ends of the needles.
Figure 8A:
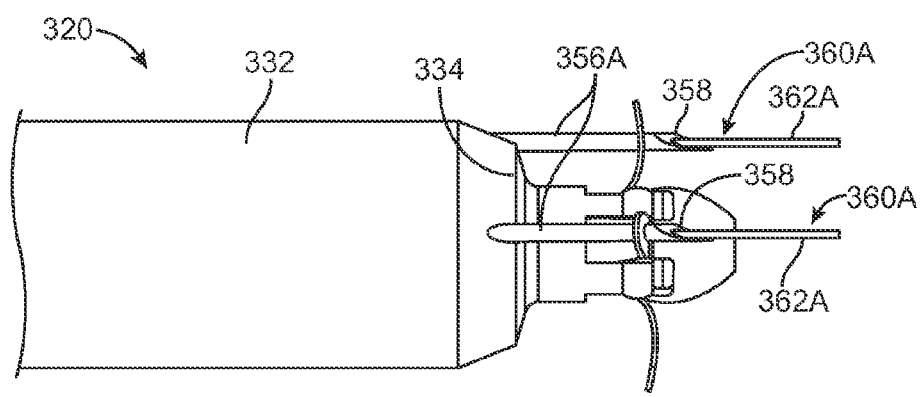
FIG. 8A is a perspective view of a distal portion of the suturing device of FIG. 3, wherein the sutures of the suturing device are deployed to extend beyond the distal ends of the needles.
Figure 8B:
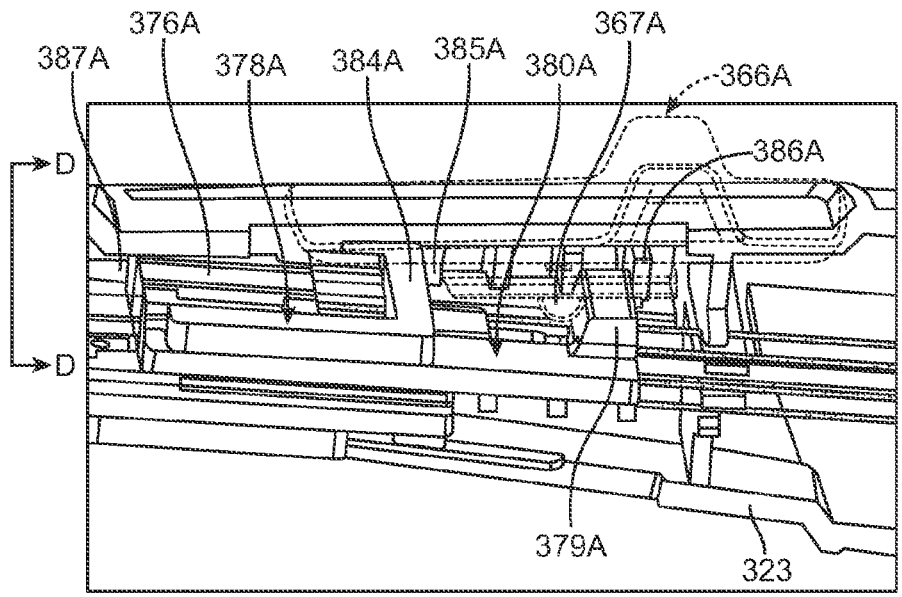
FIG. 8B is a cutaway view of a proximal portion of the handle of the suturing device of FIG. 3 exposing actuation mechanisms for deploying the needles and sutures with the top actuation mechanism shown in a suture deployment position.
Figure 8C:
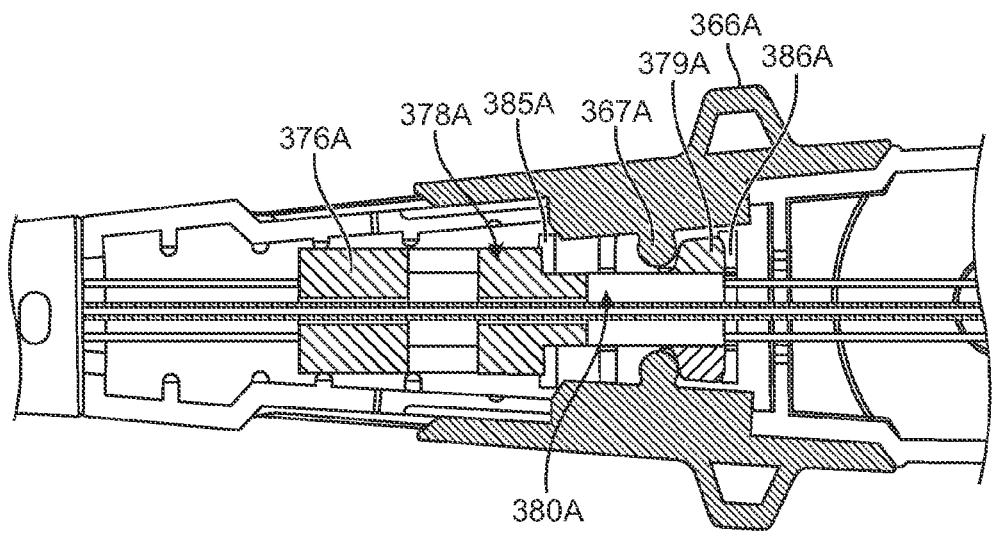
FIG. 8C is a sectional view of a proximal portion of the handle of the suturing device of FIG. 3, wherein the actuation mechanisms for extending the needles and sutures are both shown in a fully extended suture deployment position.
Figure 8D:
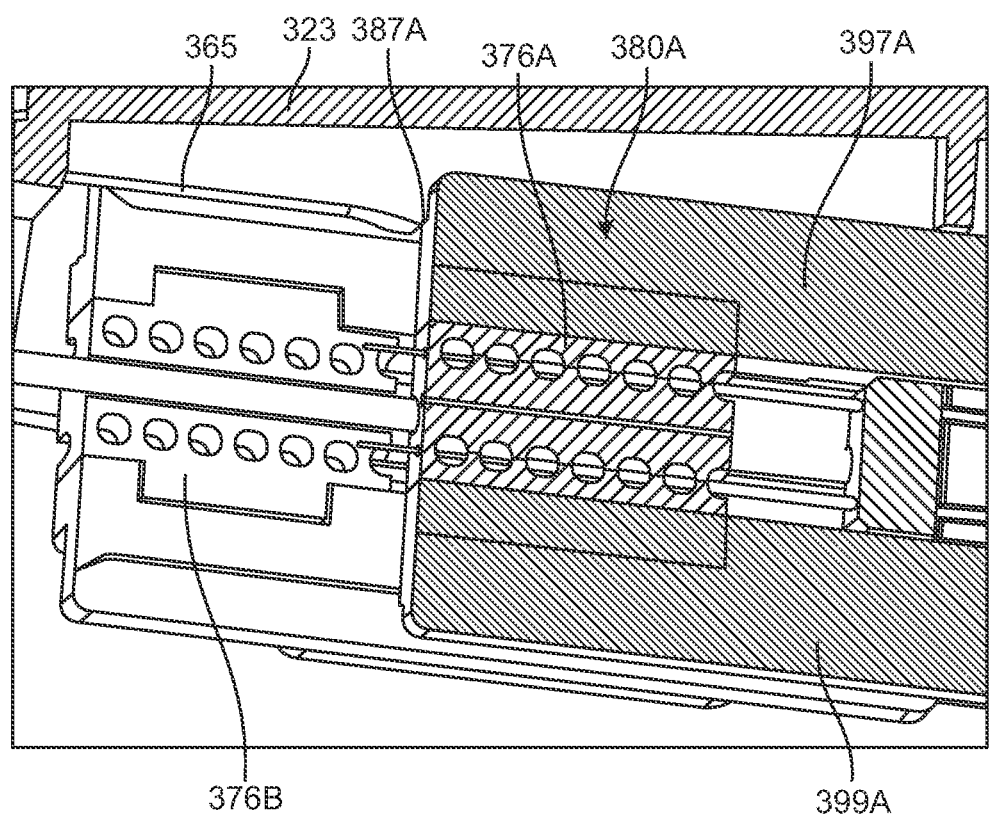
FIG. 8D is a sectional view taken along line D-D of FIG. 8B.

First ends 362A of suture pair 360A are then deployed out of or beyond distal ends 358 of needle pair 356A as shown in FIGS. 8 and 8A. In order to extend or deploy suture pair 360A out of needle pair 356A, actuator 366A on handle 322 is further distally advanced until the actuation mechanism associated therewith reaches a suture deployment position. With reference to FIGS. 8B and 8C which are cutaway and sectional views, respectively, of handle 322 at actuator 366A, further distal advancement of actuator 366A (shown in phantom in FIG. 8B) results in carriage 380A disengaging or decoupling from needle holder 378A so that carriage 380A and suture holder 376A may be further distally advanced. As previously explained, needle holder 378A is prevented from further distal movement because U-shaped proximal portion 384A of the needle holder abuts against stop 385A of housing 323 of handle 322. With additional reference back to the sectional view of FIG. 7C, as carriage 380A is further distally advanced via actuator 366A, carriage 380A overcomes the interference fit between bearing surfaces 383A and thereby squeezes or compresses distal prongs 382A of needle holder 378A to allow the carriage to slidingly advance over the needle holder. Carriage 380A, as well as suture holder 376A and suture pair 360A coupled thereto, are distally advanced via actuator 366A until distal bridge 379A of carriage 380A abuts against a stop 386A of housing 323 of handle 322 such that the suture deployment position has been reached. As such, suture pair 360A is distally advanced relative to needle pair 356A by continued movement of actuator 366A. Although the distal advancement of actuator 366A is described in two sequential method steps within FIGS. 7 and 8, it will be understood by those of ordinary skill in the art that such steps are performed by a single user action, i.e., distal advancement of actuator 366A.

Carriage 380A rides or slides along track 365 of housing 323 of handle 322 as carriage 380A is distally advanced towards stop 386A. Track 365 includes a stop 387A that projects radially inward from housing 323 of handle 322. When carriage 380A is distally advanced to the point that distal bridge 379A abuts against stop 386A, a proximalmost end or surface of carriage 380A passes over stop 387A such that the proximalmost end or surface of carriage 380A is located distal to stop 387A as shown in the sectional view of FIG. 8D. Carriage 380A may bow or arch as it passes or rides over stop 387A, and then snap back to its flat or planar shape when the proximalmost end or surface of carriage 380A is located distal to stop 387A. Stop 387A prevents retraction of carriage 380A and suture holder 376A coupled thereto, thereby locking the fully extended deployed position of suture pair 360A.

Figure 9:
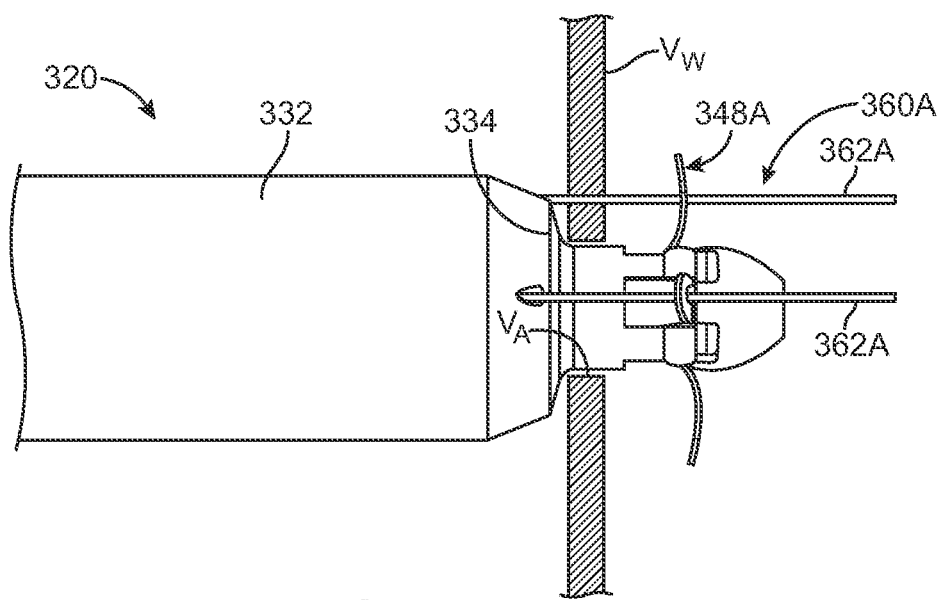
FIG. 9 is a side view illustration of a sixth step of the method of using the suturing device of FIG. 3 according to an embodiment hereof, wherein the pair of needles have been proximally retracted leaving a pair of sutures deployed within a corresponding pair of suture snags.
Figure 9A:
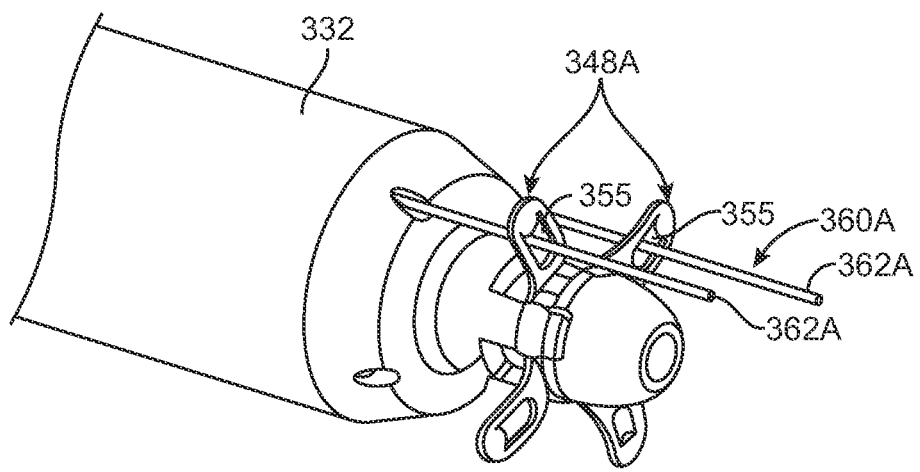
FIG. 9A is a perspective view of a distal portion of the suturing device of FIG. 3, wherein the pair of needles shown in FIG. 8A have been proximally retracted leaving a pair of sutures deployed within a corresponding pair of suture snags.
Figure 9B:
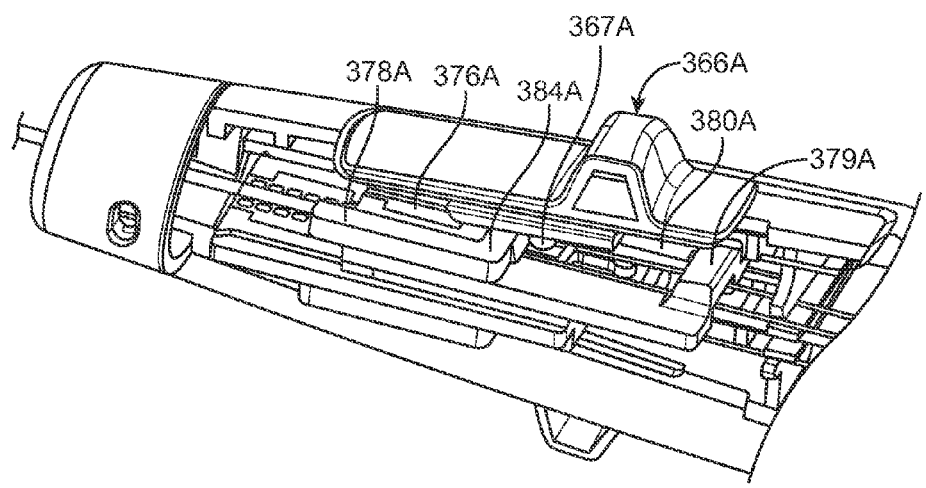
FIG. 9B is a cutaway view of a proximal portion of the handle of the suturing device of FIG. 3 exposing actuation mechanisms for deploying the needles and sutures with the actuation mechanisms shown in needle retraction positions with the sutures deployed.
Figure 9C:
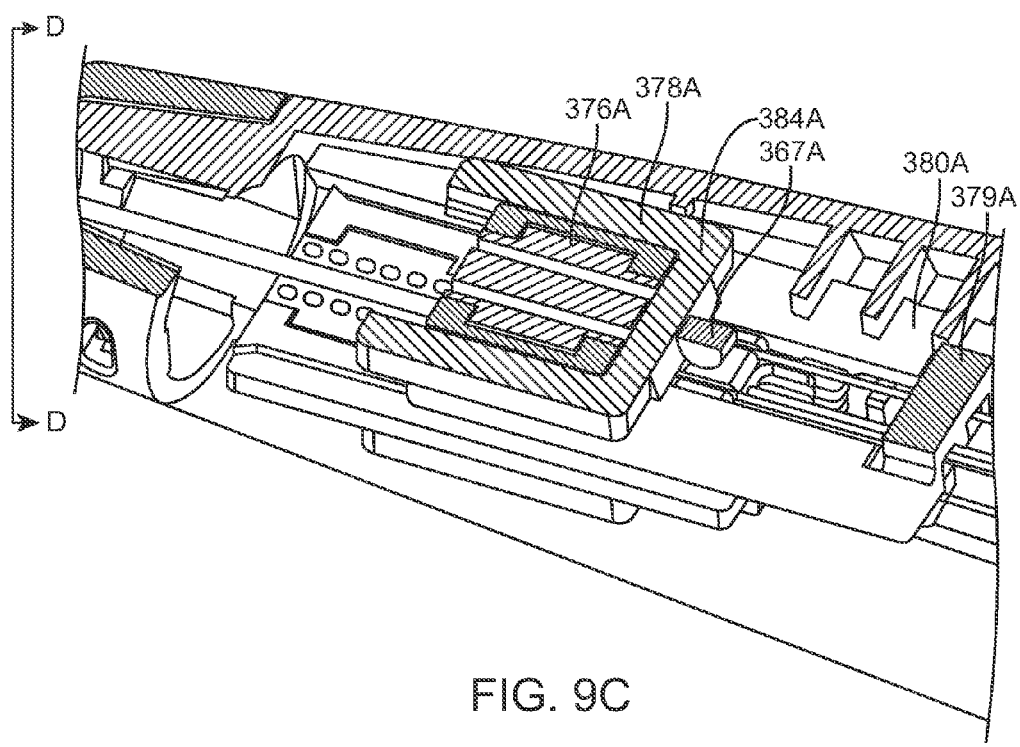
FIG. 9C is a sectional view of a proximal portion of the handle of the suturing device of FIG. 3 exposing actuation mechanisms for deploying the needles and sutures the actuation mechanisms are shown having retracted the needles while the sutures remain extended.

After distal portions of suture pair 360A are extended or deployed beyond needle pair 356A, needle pair 356A is retracted as shown in FIGS. 9 and 9A, thereby leaving only the suture ends extending through the vessel wall and through apertures 355 of deployed suture snag 348A. With additional reference to the cutaway and sectional views of FIGS. 9B and 9C, respectively, actuator 366A is proximally retracted until boss 367A thereof abuts against U-shaped proximal portion 384A of needle holder 378A and then actuator 366A pushes or proximally retracts the needle holder, thereby also proximally retracting needle pair 356A. Carriage 380A and suture pair 360A cannot be retracted since they are locked in their extended positions due to stop 387A, as described above, and needle holder 378A is free to move independently from and relative to carriage 380A since it was previously decoupled therefrom. Needle holder 378A and needle pair 356A attached thereto are proximally retracted until U-shaped proximal portion 384A of the needle holder abuts against suture holder 376A, such that the actuation mechanism may be considered to have reached a needle retraction position as shown in FIGS. 9B and 9C. Once needle holder 378A is in its needle retraction position, distal tips 358 of needle pair 356A are retracted back into distal guiding component 332.

Figure 9D:
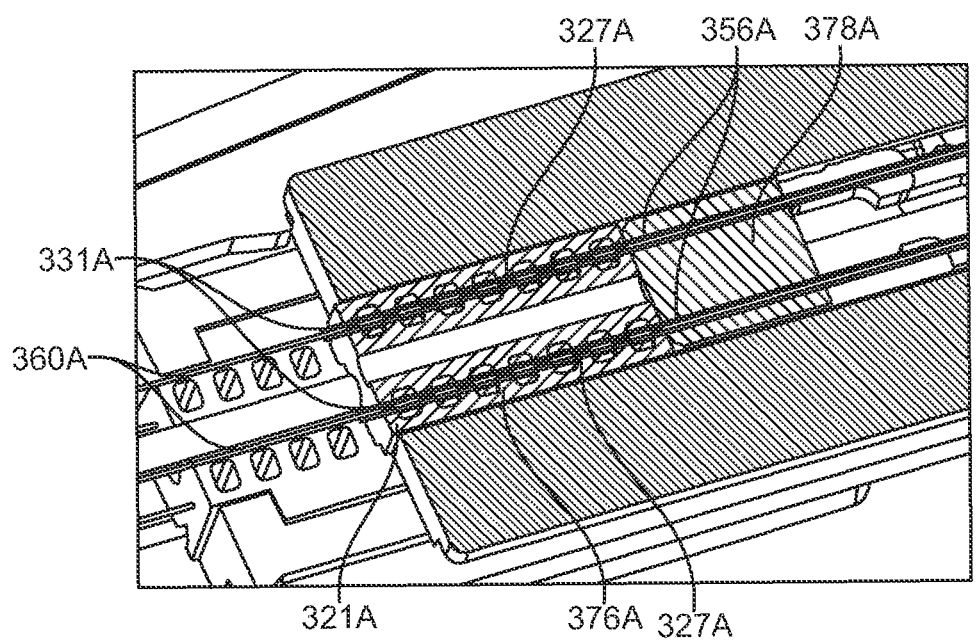
FIG. 9D is a sectional view taken along line D-D of FIG. 9C.

In addition, when needle pair 356A is in the retracted position shown in FIGS. 9, 9A, 9B, and 9C, needle pair 356A extends through longitudinal slits 327A of suture holder 376A such that proximal ends 331A of needle pair 356A are located proximal to a proximal end 321A of suture holder 376A as best shown in the sectional view of FIG. 9D to envelop or surround suture pair 360A such that suture pair 360A is slidingly positioned through needle pair 356A, and therefore is no longer coupled to suture holder 376A. Stated another way, since suture pair 360A is slidably disposed within needle pair 356A for the entire length of suture holder 376A, suture pair 360A no longer contacts the suture holder and therefore is no longer squeezed or held via an interference fit within longitudinal slits 327A of suture holder 376A. Since needle pair 356A extends through the length of suture holder 376A, suture pair 360A disengages from or decouples from suture holder 376A.

Figure 10:
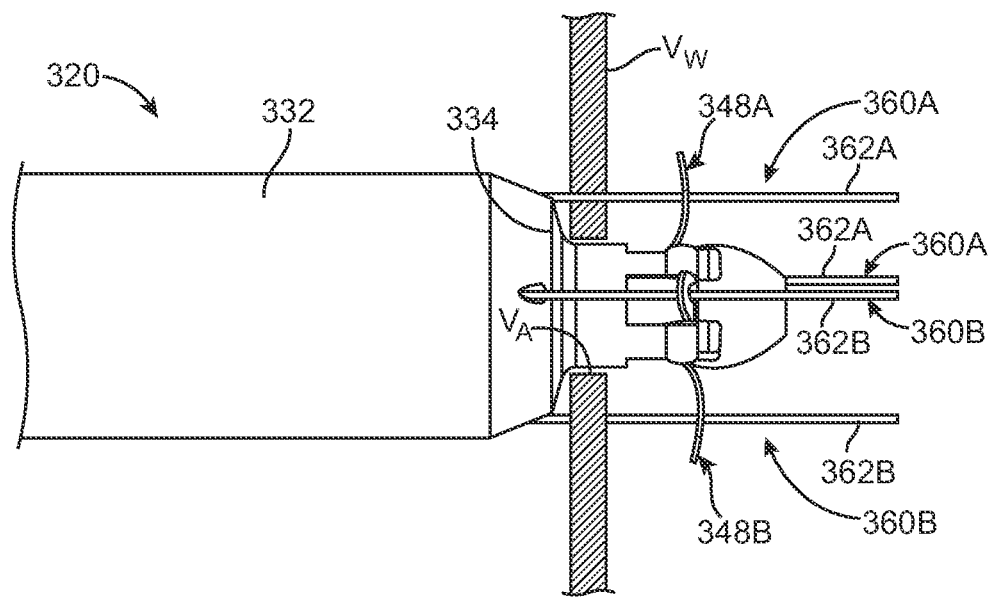
FIG. 10 is a side view illustration of a seventh step of the method of using the suturing device of FIG. 3 according to an embodiment hereof, wherein two sutures are shown extending into the arteriotomy.

As previously mentioned with respect to FIG. 7, it may be desirable to extend only a single needle pair at a time into a lumen of a vessel if the vessel is of a relatively smaller size. If only a single needle pair and corresponding suture pair has been deployed into the lumen of the vessel, the remaining needle pair 368B and first ends 362B of suture pair 360B are subsequently extended into the lumen of the vessel via actuator 366B as shown in FIG. 10 by following the method steps described above with respect to actuator 366A. Alternatively, suture pair 360B may have been extended into the lumen of the vessel via actuator 366B before or concurrently with suture pair 360A.

Figure 11:
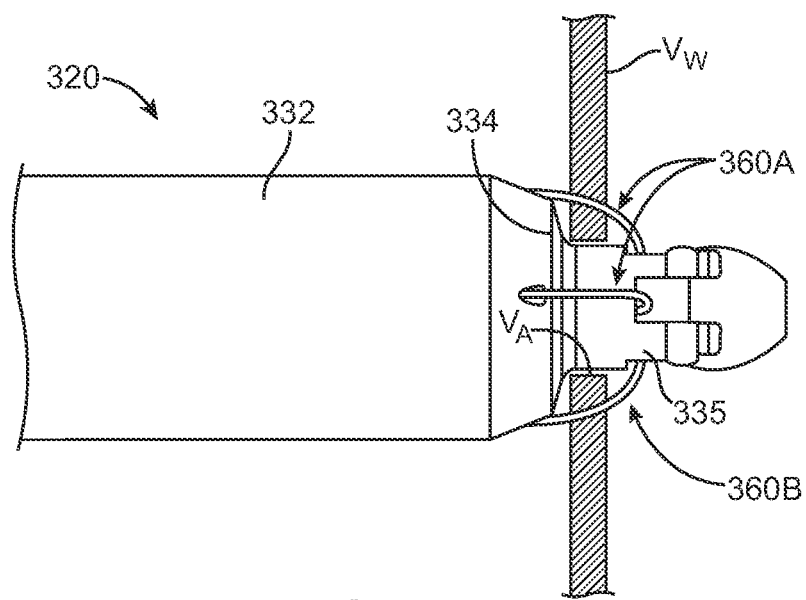
FIG. 11 is a side view illustration of an eighth step of the method of using the suturing device of FIG. 3 according to an embodiment hereof, wherein the suture snags of the suturing device are proximally retracted, thereby capturing the suture ends.
Figure 11A:
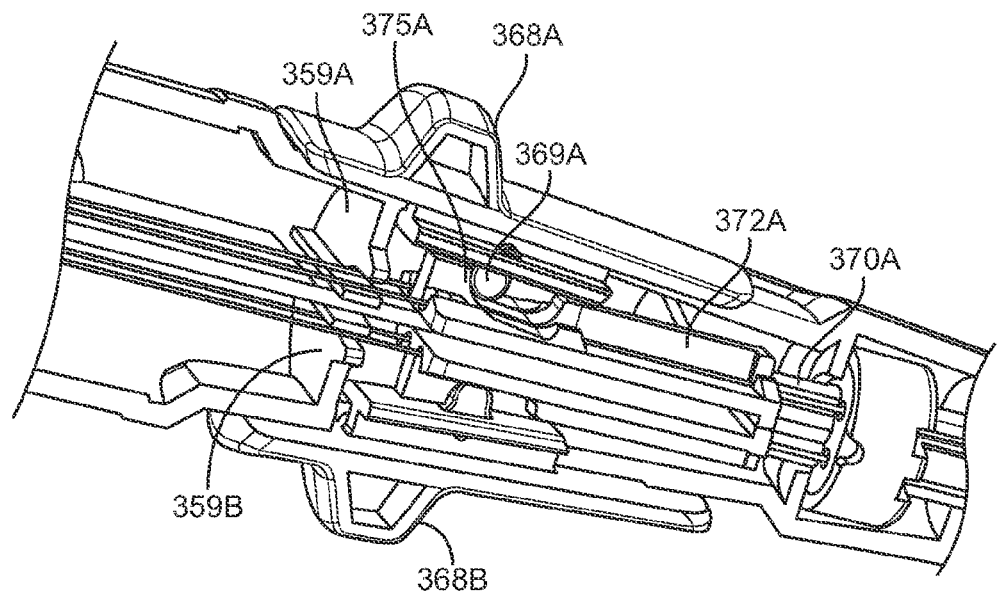
FIG. 11A is a cutaway view of a distal portion of the handle of the suturing device of FIG. 3 exposing actuation mechanisms for deploying and retracting the suture snags with the actuation mechanisms shown in a retracted position.
Figure 11B:
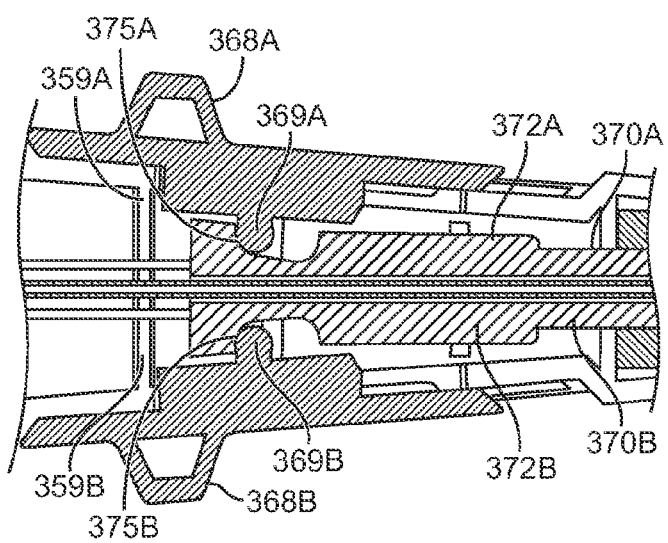
FIG. 11B is a sectional view of a portion of the handle of the suturing device of FIG. 3, wherein the handle portion includes actuation mechanisms for deploying and retracting the suture snags with the actuation mechanisms shown in a retracted position.

After respective ends of suture pairs 360A, 360B all extend into the lumen of the vessel and both needle pairs 356A, 356B have been retracted into elongated body 324 of the suturing device, suture snags 348A, 348B are proximally retracted to thereby capture the four extended suture ends and pull them into suturing device 320 as shown in FIG. 11. In order to retract suture snags 348A, 348B, actuators 368A, 368B are proximally retracted until bosses 369A, 369B thereof abut against and push proximal surfaces 375A, 375B of recesses 371A, 371B of transmission members 370A, 370B. By pushing transmission members 370A, 370B, suture snags 348A, 348B are thereby pushed or retracted back through openings 338 and into distal guiding component 332. Essentially, proximal ends 372A, 372B of transmission members 370A, 370B are returned to the position described above with respect to FIG. 4. Proximal ends 372A, 372B of transmission members 370A, 370B are proximally retracted until bosses 369A, 369B of actuators 368A, 368B, abut against stops 359A, 359B, respectively, of housing 323 of handle 322 that project radially inward to limit proximal retraction of actuators 368A, 368B. When the suture snags are retracted, suture pairs 360A, 360B extend out of ports 336 of distal guiding component 332, through tissue around the arteriotomy via the pathways or incisions created by needle pairs 356A, 356B, and then the ends of suture pairs 360A, 360B are captured within distal portion 335 of distal guiding component 332 as shown in FIG. 11. When captured, the ends of suture pairs 360A, 360B are pushed into catches or grips 339 of apertures 355 (see FIG. 6C) and therefore are tightly secured within apertures 355 of the suture snags.

Notably, other suturing devices known in the art utilize extendable needles to capture modified suture ends of a suture which have been delivered through an arteriotomy to a position within a vessel lumen. However, suturing device 320 positions ends of a suture through a vessel wall around an arteriotomy and then utilizes deployable suture snags to capture or catch the suture ends back into the suturing device. As such, suturing device 320 does not require modification of the suture ends for capture thereof. In addition, suturing device 320 improves consistency and reliability of capturing the suture ends.

At this point in the method of use, suturing device 320 having the captured suture ends therein is retracted until it is withdrawn from a patient so that a clinician gains access to second ends 364A, 364B of suture pairs 360A, 360B. More particularly, since suture pairs 360A, 360B are no longer coupled to suture holders 376A, 376B, respectively, and are instead slidingly positioned through retracted needle pairs 356A, 356B, suture pairs 360A, 360B slide through the needle pairs as the suturing device 320 (having first ends 362A, 362B captured therein) is retracted until second ends 364A, 364B of the suture pairs exit out of distal ends 358 of needle pairs 356A, 356B. The clinician then ties or forms at least one surgical knot 363 between the respective second ends of each suture pair, thereby forming a first elongated suture 361A from suture pair 360A and a second elongated suture 361B from suture pair 360B. In order to facilitate tying or forming the surgical knot between each pair of opposing suture ends, suture pair 360A may be formed from a different color and/or may be a different length than suture pair 360B so that the physician can easily identify the suture ends that are to be tied together. With reference to FIG. 12, which is a top view of vessel V having an arteriotomy $V_A$, newly formed elongated sutures 361A, 361B extend through the vessel wall around the arteriotomy and the opposing ends thereof (originally first ends 362A, 362B of suture pairs 360A, 360B) are still captured within suturing device 320. The clinician then pulls on or further proximally retracts suturing device 320 such that surgical knots 363 of elongated sutures 361A, 361B are positioned over the vessel wall and/or arteriotomy $V_A$ as shown in FIG. 12. The physician then cuts or severs elongated sutures 361A, 361B from suturing device 320. The physician may then pull one end of each elongated suture until surgical knots are accessible, i.e. located outside of the patient. A slip knot (not shown) is then tied below each surgical knot 363, and one end of each elongated suture 361A, 361B is pulled to move or slide each slip knot over the length of each elongated suture towards arteriotomy $V_A$. Hemostasis occurs when each slip knot abuts against the inside of the vessel wall, thereby closing or substantially closing the arteriotomy $V_A$ with a first stitch 393A and a second stitch 393B as shown in FIG. 13. FIG. 13 illustrates arteriotomy $V_A$ closed for illustrative purposes; however, if suturing device 320 is being utilized in a pre-closure technique, stitches 393A, 393B would seal the arteriotomy $V_A$ around an interventional device inserted through the arteriotomy $V_A$ as would be understood by one of ordinary skill in the art. The method steps described above for forming two stitches from suture pairs 360A, 360B are merely exemplary. Other devices or methods known in the art may be utilized to form two stitches from suture pairs 360A, 360B after suturing device 320 has captured the suture ends and thereby positioned the suture pairs through the vessel wall around the arteriotomy as desired. For example, although the above method illustrates forming two essentially parallel stitches 393A, 393B as shown in FIG. 13, different combinations of sutures may be tied together for forming the stitches, such as opposing sutures located 180 degrees from each other, to thereby form two stitches that crisscross in an "X" configuration. Stated another way, the elongated sutures 361A, 361B need not be formed from sutures of the same suture pair. Sutures of suture pair 360A may be tied to opposing sutures of suture pair 360B.

Figure 14A:
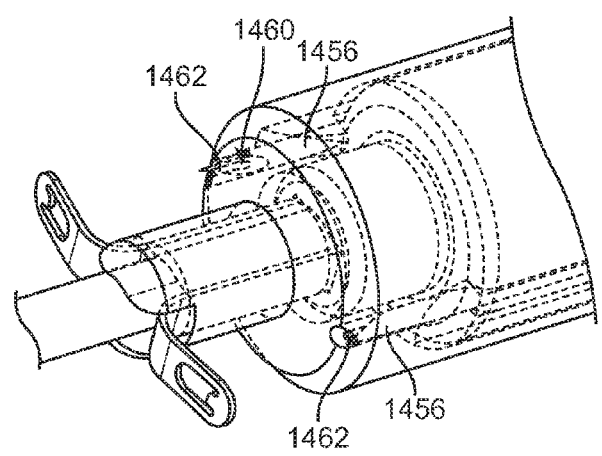
FIG. 14A is a perspective view of FIG. 14 showing the internal components in phantom.

In order to access smaller vessels, which have inherently smaller arteriotomies due to the relatively smaller diameters of the vessels themselves, it may be desirable to utilize a relatively smaller suturing device which delivers a single suture pair. FIGS. 14 and 15 illustrate an embodiment in which a suturing device 1420 includes a single suture snag 1448 and a single needle pair 1456 for delivering a single suture pair 1460. FIG. 14 and FIG. 14A are perspective views of a distal portion of suturing device 1420. As shown, suturing device 1420 includes an elongated body 1424 including an outer shaft 1426 and a distal guiding component 1432. Distal guiding component 1432 includes a distally tapered region that ends at an abutment surface 1434, and distal guiding component 1432 is utilized for guiding needle pair 1456 towards deployed suture snag 1448 having radially expandable distal arm portions 1451, 1453. A first suture of suture pair 1460 is housed within a first needle of needle pair 1456, and a second suture of suture pair 1460 is housed within a second needle of needle pair 1456. FIG. 14A illustrates first ends 1462 of suture pair 1460 housed within the distal ends of needle pair 1456.

Figure 15A:
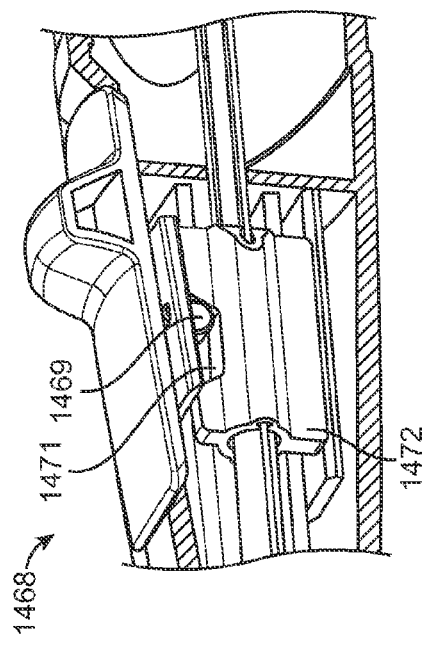
FIG. 15A is an enlarged sectional view of a distal portion of the handle of FIG. 15 illustrating an actuation mechanism for deploying the single suture snag.

FIG. 15 illustrates a sectional view of a handle 1422 of suturing device 1420, which deploys a single suture snag 1448 as well as only a single needle pair 1456 and single suture pair 1460. FIG. 15A is an enlarged sectional view of actuator 1468 for deploying and retracting suture snag 1448. As shown, similar to actuator 368, actuator 1468 includes a knob or boss 1469 which slidingly operates within a recess or groove 1471 of a proximal end 1472 of a transmission member 1470 which extends to and couples with a proximal end of suture snag 1448. Actuator 1468 distally advances or proximally retracts transmission member 1470, thereby distally advancing or proximally retracting suture snag 1448. FIGS. 15B, 15C, and 15D are views of actuator 1466 for extending and retracting needle pair 1456, as well as for extending suture pair 1460. As shown, similar to actuator 366, actuator 1466 includes a knob or boss 1467 which operates to distally advance a shuttle or carriage 1480. In the delivery configuration of the suturing device, a suture holder 1476 and a needle holder 1478 are both coupled to carriage 1480. Carriage 1480 includes a first leg 1497, a second leg 1499, which extends substantially parallel but spaced apart from first leg 1497, and a distal bridge 1479 which extends between the proximal ends of first and second legs 1497, 1499. Suture holder 1476 is positioned adjacent to and coupled to a distal portion of carriage 1480, between first and second legs 1497, 1499 thereof. Since suture holder 1476 is coupled to carriage 1480, carriage 1480 essentially pulls or carries suture holder 1476, and thus suture pair 1460 attached thereto, forward when carriage 1480 is distally advanced via actuator 1466. Needle holder 1478 includes a distal portion having claws or prongs 1482, which in this embodiment essentially clips or bosses to distal bridge 1479 of carriage 1480. Needle holder 1478 also includes a U-shaped proximal portion 1484A which includes a pair of channels or lumens 1490 formed there through for receiving needle pair 1456 and also includes a channel 1492 formed on an inner surface thereof for sliding or riding along inner shaft 1440. In a delivery configuration of the suturing device, needle holder 1478 is coupled to carriage 1480 via mating or bearing surfaces 1483 formed between prongs 1483 of the needle holder and distal bridge 1479 of the carriage. As a result of the interference fit between needle holder 1478 and carriage 1480 at bearing surfaces 1483, carriage 1480 pushes or carries needle holder 1478, and thus needle pair 1456 attached thereto, forward when carriage 1480 is distally advanced via actuator 1466 until the needle holder abuts against a stop 1485 of a housing 1423 of handle 1422. Needle holder 1478, as well as needle pair 1456 attached thereto, cannot be distally advanced any further but continued distal advancement of actuator 1466 results in continued distal advancement of carriage 1480, as well as suture holder 1476 and the ends of suture pair 1460. As best shown in FIG. 15C, continued distal advancement of carriage 1480 results in carriage 1480 overcoming the interference fit between bearing surfaces 1483 and thereby spreading or pushing apart distal prongs 1482 of needle holder 1478, thereby decoupling needle holder 1478 and carriage 1480 to allow the carriage to slidingly advance through or past the needle holder. As such, suture pair 1460 is distally advanced by continued movement of actuator 1466 while needle pair 1456 is not.

Figure 16:
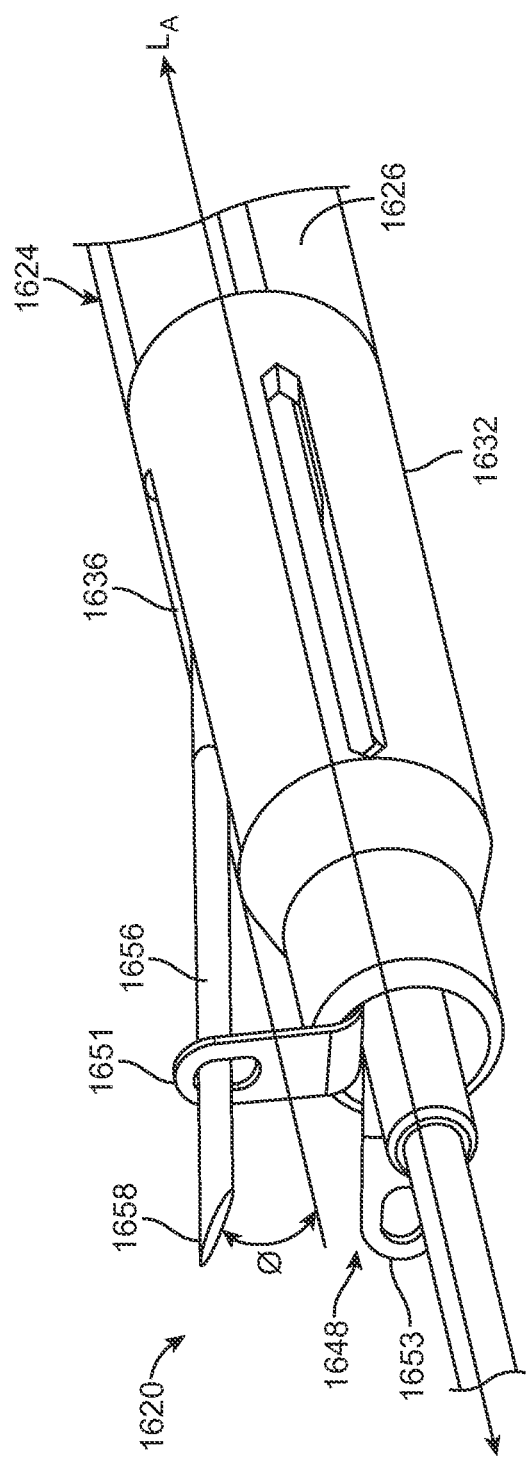
FIG. 16 is a perspective view of a distal end of a suturing device according to another embodiment hereof, wherein the suturing device includes needles that bend when extended from the suturing device.

In another embodiment hereof, in order to access smaller vessels, the size or outer diameter of the elongated body of the suturing devices described herein may be minimized by designing the plurality of needles to bend when being extended out of the distal guiding component. In an embodiment shown in FIG. 16, a suturing device 1620 includes an elongated body 1624 having an outer shaft 1626 and a distal guiding component 1632. Distal guiding component 1632 is utilized for guiding a needle pair 1656 towards deployed suture snag 1648 having radially extendable distal arm portions 1651, 1653. Only one suture snag is shown deployed in FIG. 16, and only one needle is shown for sake of clarity and illustration. In this embodiment, distal guiding component 1632 includes a plurality of side openings or ports 1636 in a wall thereof that each allow the needle associated therewith to be alternately extended and retracted therethrough. In a retracted position each needle is disposed within the elongated body and in an extended position each needle extends distally and radially outward from a longitudinal axis $L_A$ of elongated body 1624. As will be understood by one of ordinary skill in the art, the number of ports 1636 formed through distal guiding component 1632 corresponds to the number of needles located within the elongated body of suturing device 1620. When each needle pair 1656 is distally advanced, distal ends 1658 comes into contact with a curved deflection surface or edge formed within transverse port 1636 that operates to guide distal ends 1658 of each needle out of elongated body 1624 and causes each needle to bend radially outward at an acute angle relative to the longitudinal axis $L_A$ of elongated body 1624. As distal end 1658 exits from transverse port 1636, each needle gradually bends and assumes the extended position shown in FIG. 16 in which each needle extends distally and outwardly from elongated body 1624. In embodiment hereof, the angle ⊖ of the needle deflection may be in a range of between 5 and 25 degrees. When needle pair 1656 is retracted back into elongated body 1624, they return to their original generally straight configurations since they are no longer in contact with the deflection surface of distal guiding component 1632 that caused the needles to bend radially outward in the extended position.

Figure 17:
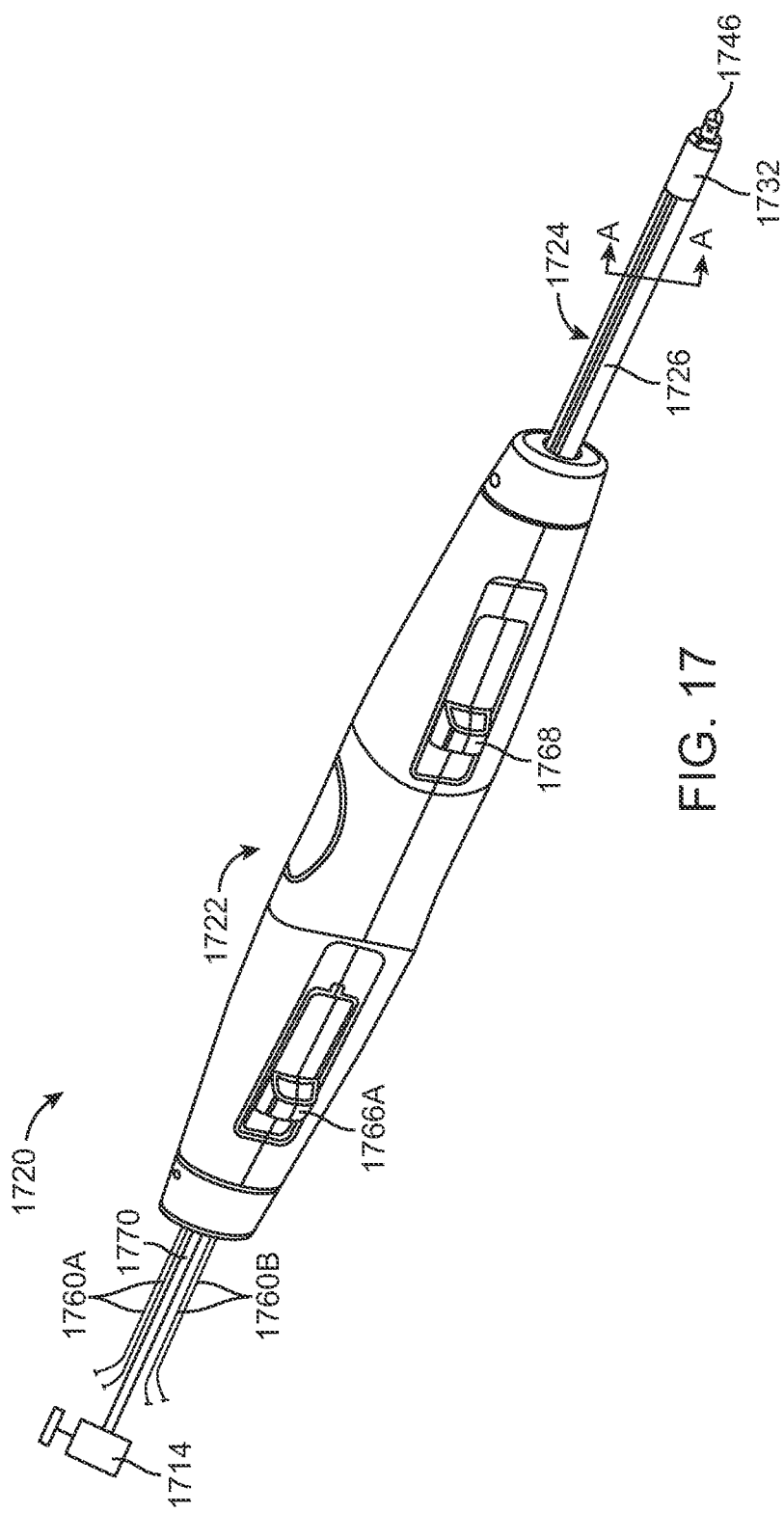
FIG. 17 is a perspective view of a suturing device according to another embodiment hereof for sealing or closing an arteriotomy, wherein the suturing device is in a delivery configuration in which an inflatable balloon thereof is in a retracted position and the needles and sutures are in a loaded position.

In another embodiment hereof, an inflatable balloon may be utilized as an alternative to suture snags for capturing the ends of the suture(s) beyond the boundaries of the arteriotomy. An inflatable balloon provides a relatively larger target area or zone for placement of the needles of the suturing device. In addition, an inflatable balloon may provide apposition to the inner vessel wall during the suturing procedure, thereby improving the structural integrity of the vessel wall for the needles to puncture or penetrate there through. More particularly, with initial reference to FIGS. 17 and 17A, suturing device 1720 includes first and second needle pairs 1756A, 1756B and an inflatable balloon 1810 (shown in FIG. 18) for positioning and capturing respective ends of first and second suture pairs 1760A, 17608 beyond the boundaries of the arteriotomy. Suturing device 1720 includes a transmission shaft 1770, as well as suture pairs 1760A, 1760B extending proximally from a handle 1722 and an elongated body 1724 extending distally from handle 1722. Handle 1722 includes first and second sliders or actuators 1766A, 1766B (slider 1766B is not shown on the view of FIG. 17 but is located on the handle similar to slider 366B described above) which each interact with a suture holder, needle holder, and carriage (not shown in FIG. 17 but disposed within handle 1722) to extend needle pairs 1756A, 1756B, respectively, and suture pairs 1760A, 1760B, respectively, as described above with respect to actuators 366A, 366B. Handle 1722 also includes a third slider or actuator 1768 which is utilized to distally advance or extend inflatable balloon 1810 as will be described in more detail herein.

Similar to elongated body 324 described above, elongated body 1724 includes an outer shaft 1726 and a distal guiding component 1732 which is disposed over and coupled to a distal portion of outer shaft 1726. Outer shaft 1726 and distal guiding component 1732 collectively define or include a plurality of needle pathways or guides 1730 for housing needle pairs 1756A, 1756B, which are slidingly disposed thereon or therein. With reference to the cross-sectional view of FIG. 17A, needle guides 1730 may be formed via channels or grooves formed on an exterior surface of outer shaft 1726 that mate with a plurality of lumens formed through distal guiding component 1732. Alternatively, rather than channels or grooves formed on the outer surface thereof, outer shaft 1726 may define individual lumens for housing each needle. Each of the outer shaft and the distal guiding component are hollow tubular components and collectively define at least one continuous lumen 1728 through elongated body 1724 for housing transmission shaft 1770, as shown in the cross-sectional view of FIG. 17A. Transmission shaft 1770 extends through handle 1732 to a tapered distal tip or nosecone 1746, which is coupled to a distal end portion 1745 (shown in FIGS. 18-19) of transmission shaft 1770.

Figure 18:
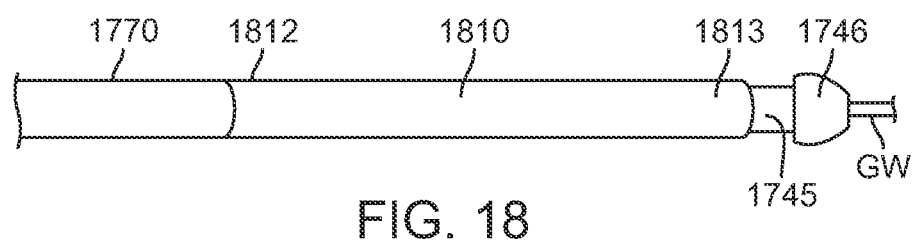
FIG. 18 is a side view of a distal portion of a transmission shaft and the inflatable balloon coupled thereto, removed from the suturing device for illustrative purposes only, wherein the inflatable balloon is in the delivery configuration.
Figure 19:
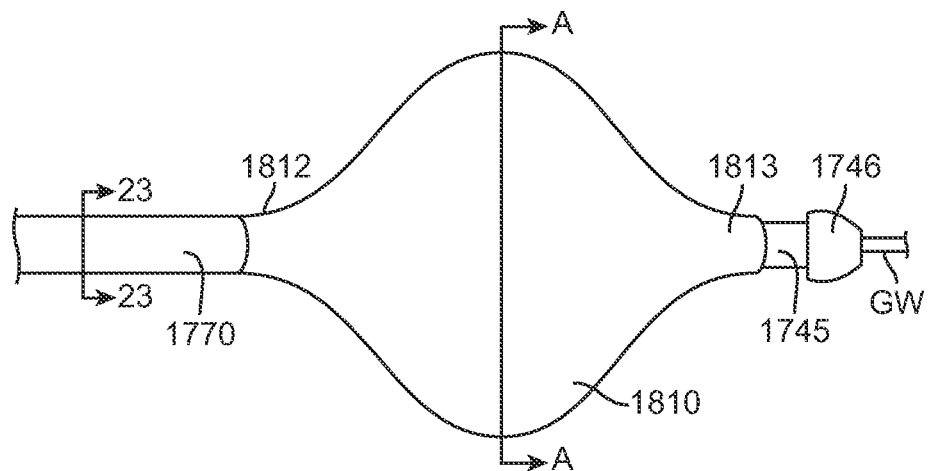
FIG. 19 is a side view of the distal portion of the transmission shaft and the inflatable balloon of FIG. 18, removed from the suturing device for illustrative purposes only, wherein the inflatable balloon is in the expanded or inflated configuration.

A distal portion of transmission shaft 1770 is shown removed from suturing device 1720 for illustration purposes only in FIGS. 18 and 19. The distal portion of transmission shaft 1770 is positionable through an arteriotomy and includes inflatable balloon 1810, which is shown in a deflated or delivery configuration in FIG. 18 and in an expanded or inflated configuration in FIG. 19. As will be understood by those of ordinary skill in the art, transmission shaft 1770 and balloon 1810 collectively form a balloon catheter. A proximal end or neck 1812 and a distal end or neck 1813 of balloon 1810 is coupled to distal end portion 1745 of transmission shaft 1770. Proximal and distal necks 1812, 1813 of balloon 1810 may be joined to transmission shaft 1770 in any conventional manner known to one of skill in the art of balloon catheter construction, such as by laser welding, adhesives, heat fusing, or ultrasonic welding. Transmission shown 1770 is a tubular shaft formed by multi-lumen profile extrusion. Transmission shaft 1770 defines at least an inflation lumen 1715 and a guidewire lumen 1742 for tracking suturing device 1720 over a guidewire GW (shown in FIGS. 18-19). Inflation lumen 1715 extends the full length of transmission shaft 1770 to allow inflation fluid received through an inflation port of a hub 1714 (shown in FIG. 17) to be delivered to inflatable balloon 1810. Inflation lumen 1715 is in fluid communication with an interior of balloon 1810 via a port or opening (not shown) of transmission shaft 1770 to allow inflation fluid, i.e., saline, to flow between the inflation lumen and the interior of the balloon. As would be understood by one of ordinary skill in the art of balloon catheter design, hub 1714 provides a luer hub or other type of fitting that may be connected to a source of inflation fluid and may be of another construction or configuration without departing from the scope of the present invention. In addition, hub 1714 includes a guidewire port (not shown) that communicates with lumen 1742 of transmission shaft 1770 for receiving a guidewire GW there through. Transmission shaft 1770 may be formed of a polymeric material, non-exhaustive examples of which include polyethylene, PEBA, polyamide and/or combinations thereof, either blended or co-extruded.

Figure 17B:
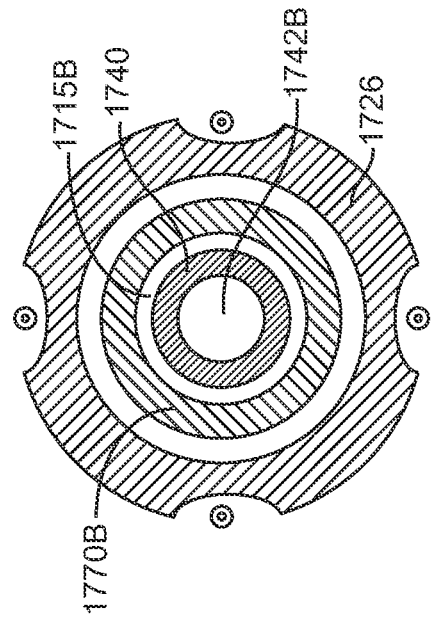
FIG. 17B is a cross-sectional view of FIG. 17 taken along line A-A according to another embodiment hereof.
Figure 17A:
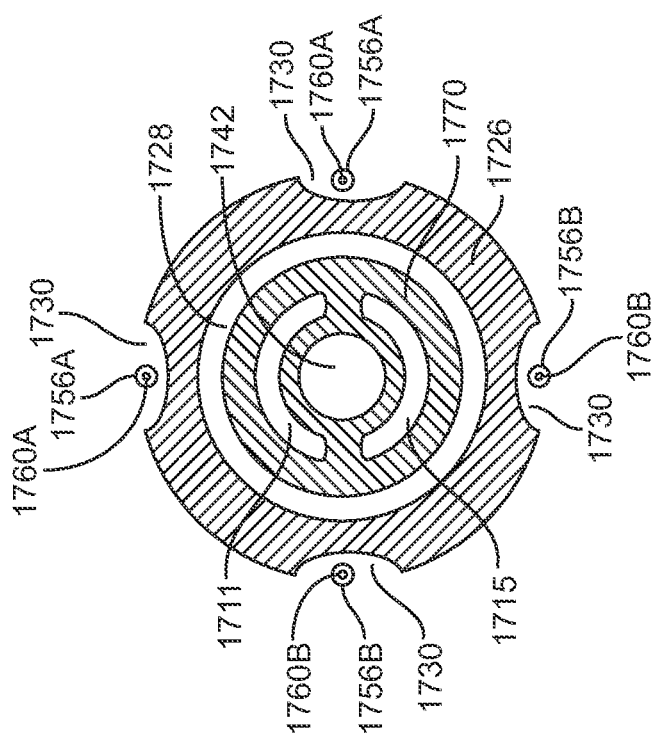
FIG. 17A is a cross-sectional view of FIG. 17 taken along line A-A.

As shown in FIG. 17A, although not required, transmission shaft 1770 may also define further lumens in addition to inflation lumen 1715 and guidewire lumen 1742. In the embodiment of FIG. 17A, transmission shaft 1770 defines a gas egress lumen 1711 that provides a pathway for gas to exit as balloon 1810 is filled with inflation fluid via inflation lumen 1715. Gas egress lumen 1711 is in fluid communication with an interior of balloon 1810 via a port or opening (not shown) of transmission shaft 1770 to allow gas or air to exit from the interior of the balloon into the gas egress lumen. More particularly, prior to inflation of balloon 1810, gas or air may be present within inflation lumen 1715. During balloon inflation, such gas gets pushed into the interior volume of balloon 1810 and creates a trapped gas or air bubble inside the balloon. Such gas bubbles may be released into the blood stream when needle pairs 1756A, 1756B are distally advanced or deployed into the balloon, as will be described in more detail herein. Although small amounts of gas or air can be introduced into the blood stream without patient injury, it is desired to minimize the amount of gas that can expel from the balloon after it is punctured by the needle(s). Thus, gas egress lumen 1711 provides a pathway for the gas to travel through during balloon inflation so that the trapped gas bubbles do not form within the interior of balloon 1810.

As previously mentioned, third slider or actuator 1768 of handle 1722 is utilized to distally advance or extend inflatable balloon 1810. Balloon 1810 in its deflated or delivery configuration is disposed or housed within distal guiding component 1732 during delivery of suturing device 1720 so that it does not catch on the vessel walls of the vasculature during insertion and removal of the suturing device. Balloon 1810 is deployed by third actuator 1768 on handle 1722 that interacts with transmission shaft 1770, which extends from balloon 1810 and through handle 1722. More particularly, third actuator 1768 is coupled to transmission shaft 1770 within handle 1722 so that when it is desired to distally advance balloon 1810, actuator 1768 is slid forward or distally advanced to push or distally advance transmission shaft 1770, thereby also pushing or distally advancing balloon 1810 coupled thereto. Thus, when it is desired to proximally retract balloon 1810, actuator 1768 is slid backward or proximally retracted to pull or proximally retract transmission shaft 1770, thereby also pulling or proximally retracting balloon 1810.

In the construction of FIG. 17A, transmission shown 1770 is a single shaft formed by multi-lumen profile extrusion and defines a plurality of lumens there-through. Other types of construction of the transmission shaft are also amendable to the invention, such as, without limitation thereto, dual concentric shafts. More particularly, as shown in the embodiment of FIG. 17B, an inner shaft 1740 which defines a guidewire lumen 1742B may extend within a transmission shaft 1770B such that an annular inflation lumen 1715B is defined between an inner surface of transmission shaft 1770B and an outer surface of inner shaft 1740. As will be understood by those of ordinary skill in the art, transmission shaft 1770B, inner shaft 1740, and a balloon (not shown) collectively form a balloon catheter having an over-the-wire (OTW) configuration with a proximal end or neck the balloon coupled to a distal end of transmission shaft 1770B, and a distal end or neck of the balloon is coupled to a distal end portion of inner shaft 1740. In this embodiment, transmission shaft 1770B and inner shaft 1740 may be coupled together so that the concentric shafts as well as the balloon are distally advanced and proximally retracted as a single unit or assembly. The concentric shafts may be coupled together via one or more bonds (not shown) which are non-circumferential so as not to interfere with the flow of inflation fluid through inflation lumen 1715B.

Figure 19A:
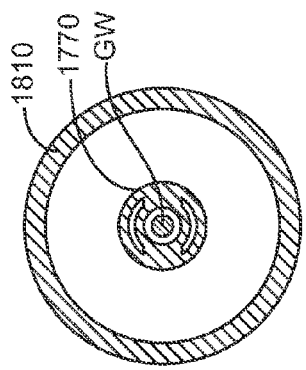
FIG. 19A is a cross-sectional view of FIG. 19 taken along line A-A.

With reference to the cross-sectional view of FIG. 19A, taken along line A-A of FIG. 19, in one embodiment hereof, balloon 1810 is a single layer balloon defining a single compartment or interior volume. Balloon 1810 may be formed from any material that is relatively elastic and deformable, including a compliant or semi-compliant material. Balloon compliance can be defined as the change in balloon diameter and length as a function of inflation pressure. A high compliance balloon has a relatively large increase in diameter and length in response to an increase in inflation pressure, while a balloon having a relatively small increase in diameter and length in response to an increase in inflation pressure is said to be a low compliance balloon or a non-compliant balloon. Non-exhaustive examples of materials for balloon 1810 include polymers such as silicone, polyethylene, PEBA, polyethylene terephthalate (PET), polyamide, and polyurethane, copolymers or blends thereof. In one embodiment, balloon 1810 is a relatively compliant thermoplastic elastomer (TPE) material. The compliant material of balloon 1810 is self-sealing such that the insertion and removal of needles through the balloon material does not affect the operation, i.e., the inflation and deflation, of the balloon. Compliant or semi-compliant materials such as those listed above as non-exhaustive examples of materials for balloon 1810 exhibit self-sealing characteristics due to the compliant nature thereof. In general, the compliance of the material is directly related or proportional to the self-sealing ability of the material such that higher compliance materials result in more self-sealing characteristics.

In an embodiment hereof, balloon 1810 is pre-blown or pre-formed, i.e., formed by extruding material into a tube shape and then forming the tube into a balloon through a process known as blow molding as will be understood by those of ordinary skill in the art of catheter balloon manufacture. When inflated, pre-formed balloons expand to the predetermined expanded or inflated shape or diameter of the mold that was used in the blow molding process. In another embodiment hereof, balloon 1810 is not pre-formed but rather may be an extruded tubular component that freely expands and deflates back to a tubular configuration. As used herein, "freely expands" refers to uncontrolled expansion of the balloon rather than expansion to a predetermined expanded or inflated shape of the mold that was used in the blow molding process. The inflated or expanded configuration of a non pre-formed balloon is generally spherical and may be similar to that of a pre-formed balloon, however, such expansion is less controlled and the outer diameter thereof is less predictable. Such a non pre-formed balloon may be deflated via retraction or removal of the needles of the suturing device, and thus does not require a vacuum to cause deflation thereof. More particularly, when the needles of suturing device 1720 are proximally retracted as described in more detail herein, removal of the needles causes the non pre-formed balloon to deflate or revert back to its tubular deflated or delivery configuration due to the elastic nature of the balloon. As the non pre-formed balloon deflates, the inflation fluid, i.e., saline, leaks out of the holes formed by needle pairs 1756A, 1756B. Although a vacuum is not required to cause deflation of a non pre-formed balloon, it will be apparent to one of ordinary skill in the art that a vacuum may be applied to accelerate deflation of the balloon.

Figure 20:
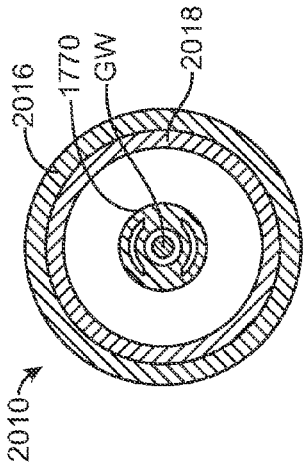
FIG. 20 is a cross-sectional view of FIG. 19 taken along line A-A according to another embodiment hereof, wherein the inflatable balloon includes dual layers.

In embodiments hereof, the balloon may include dual or double layers of different materials and/or may include multiple compartments or chambers. For example, as illustrated in FIG. 20 in another embodiment taken along line A-A of FIG. 19, a balloon 2010 includes an outer layer 2016 and an inner layer 2018. Outer layer 2016 is formed from a compliant or semi-compliant material that is self-sealing, such as those listed above with respect to balloon 1810, while inner layer 2018 is formed from a non-compliant or low-compliant material such as but not limited to polyethylene terephthalate, or nylon-based non-compliant materials such as Grilamid™ or Vestamid™. Since non-compliant materials generally expand more predictably than compliant materials and have a higher tensile strength than compliant materials, the addition of non-compliant inner layer 2018 allows balloon 2010 to be pre-blown or pre-formed to a predetermined inflated or expanded diameter while compliant outer layer 2016 provides the self-sealing function.

Figure 22:
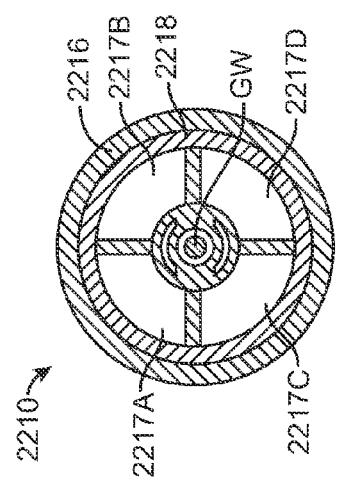
FIG. 22 is a cross-sectional view of FIG. 19 taken along line A-A according to another embodiment hereof, wherein the inflatable balloon includes dual layers and multiple compartments.
Figure 21:
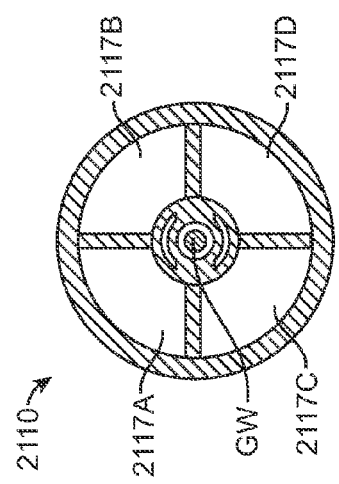
FIG. 21 is a cross-sectional view of FIG. 19 taken along line A-A according to another embodiment hereof, wherein the inflatable balloon includes multiple compartments.
Figure 23:
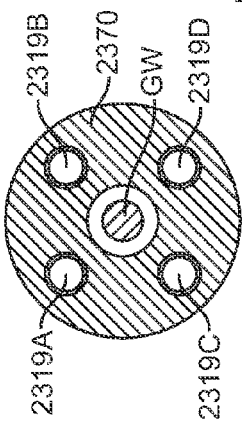
FIG. 23 is a cross-sectional view of FIG. 19 taken along line 19-19 according to another embodiment hereof, wherein the transmission shaft includes multiple lumens for independent inflation of the multiple compartments of the inflatable balloon.

Balloons having multiple compartments or chambers are illustrated in FIGS. 21-22, other embodiments taken along line A-A of FIG. 19. FIG. 21 illustrates a single layer balloon 2110 having four internal compartments 2117A, 2117B, 2117C, 2117D, collectively referred to as compartments 2117. Four compartments 2117 correspond to the four needles of needle pairs 1756A, 1756B. Multiple compartments 2117 ensure that if any leakage of inflation fluid occurs when a needle pierces into its respective compartment, the leakage would be confined to a single chamber of the balloon and pressure may be maintained in the non-affected compartments. In addition, multiple compartments 2117 are beneficial when needle pairs 1756A, 1756B are deployed non-simultaneously because each compartment is individually inflatable as described in more detail herein and may be selectively inflated immediately prior to deployment of the corresponding needle pair. Balloon 2110 is formed from a compliant or semi-compliant material that is self-sealing, such as those listed above with respect to balloon 1810. FIG. 22 illustrates a dual layer balloon 2210 having four compartments 2217A, 2217B, 2217C, 2217D. Balloon 2210 includes an outer layer 2216 and an inner layer 2218. Outer layer 2216 is formed from a compliant or semi-compliant material that is self-sealing, such as those listed above with respect to balloon 1810, while inner layer 2218 is formed from a non-compliant or low-compliant material such as but not limited to polyethylene terephthalate. If the suturing device includes a balloon having multiple internal compartments, i.e., balloon 2110 or balloon 2210, transmission shaft 2370 as shown in FIG. 23 defines a plurality of individual inflation lumens 2319A, 2319B, 2319C, 2319D extending there-through rather than a single inflation lumen such that inflation and deflation of each individual compartment of the balloon may be separately and selectively controlled. Thus, each chamber or compartment of the balloon is independently inflatable.

Figure 24:
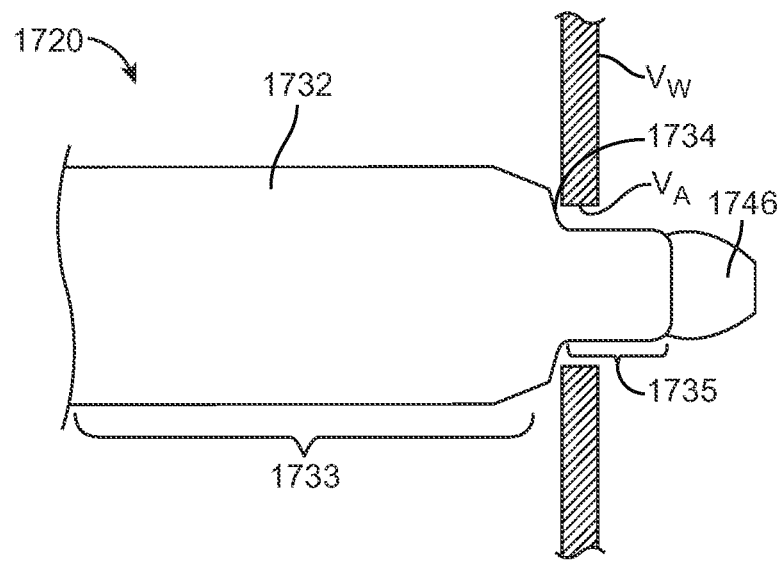
FIG. 24 is a side view illustration of a first step of the method of using the suturing device of FIG. 17 according to an embodiment hereof, wherein the suturing device is advanced towards and positioned through the arteriotomy.

FIGS. 24-32 illustrate a method of using suturing device 1720 in order to position two sutures at an arteriotomy of a vessel wall of a vessel. Referring to FIG. 24, suturing device 1720 is shown advanced to a position in which a distal portion thereof is positioned through a target arteriotomy $V_A$ such that distal tip 1746 is disposed within a lumen of the vessel. Suturing device 1720 is in a delivery configuration, in which inflatable balloon 1810 is in a deflated configuration and disposed within the elongated body of the suturing device. In addition, needle pairs 1756A, 1756B and suture pairs 1760A, 1760B are in a loaded position described above with respect to FIGS. 4 and 17. Similar to distal guiding component 332, distal guiding component 1732 includes a stepped or tapered region which creates an abutment surface 1734. As shown in FIG. 24, a distal portion 1735 of distal guiding component 1732 is sized to protrude through the arteriotomy $V_A$ and extend into the lumen of the vessel, while a proximal portion 1733 of distal guiding component 1732 is sized to abut against the outer surface of the vessel wall $V_W$ and not protrude or extend through the arteriotomy $V_A$ and into the lumen of the vessel. When the user is advancing suturing device 1720 to the arteriotomy $V_A$, a resistance to further advancement is felt when abutment surface 1734 contacts the vessel wall, thereby notifying the user that the suturing device is in place within the arteriotomy $V_A$ as desired.

Figure 25:
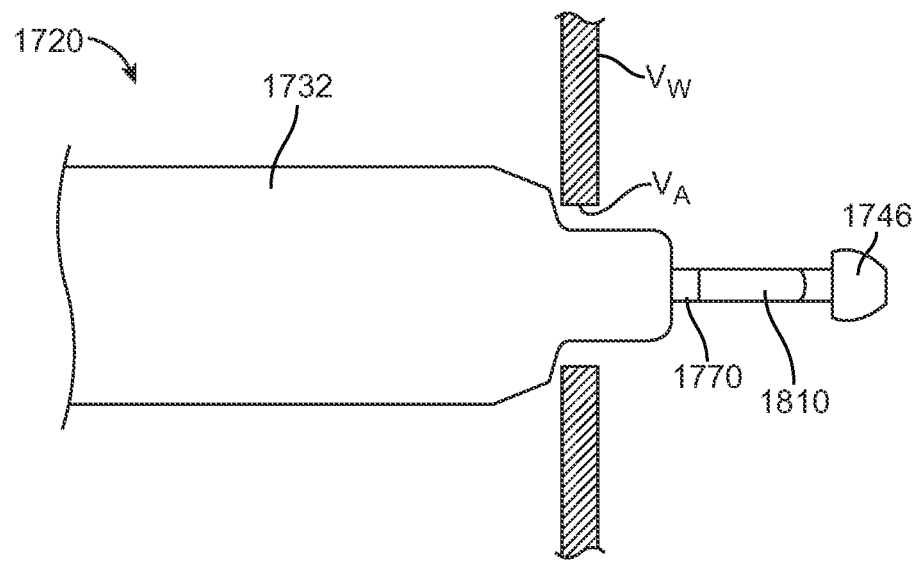
FIG. 25 is a side view illustration of a second step of the method of using the suturing device of FIG. 17 according to an embodiment hereof, wherein the inflatable balloon of the suturing device is distally advanced.

Once the distal portion of distal guiding component 1732 is positioned through the arteriotomy $V_A$ of the vessel to reside within the lumen of the vessel, transmission shaft 1770, and balloon 1810 coupled thereto are distally advanced such that balloon 1810 exits from a distalmost opening of distal guiding component 1732 and is positioned within the lumen of the vessel as shown in FIG. 25. While being distally advanced or extended into position, balloon 1810 remains in its deflated or delivery configuration. When it is desired to distally advance or extend balloon 1810, actuator or slider 1768 of handle 1722 is distally advanced such that the actuator pushes or distally advances transmission shaft 1770 as described above.

Figure 26:
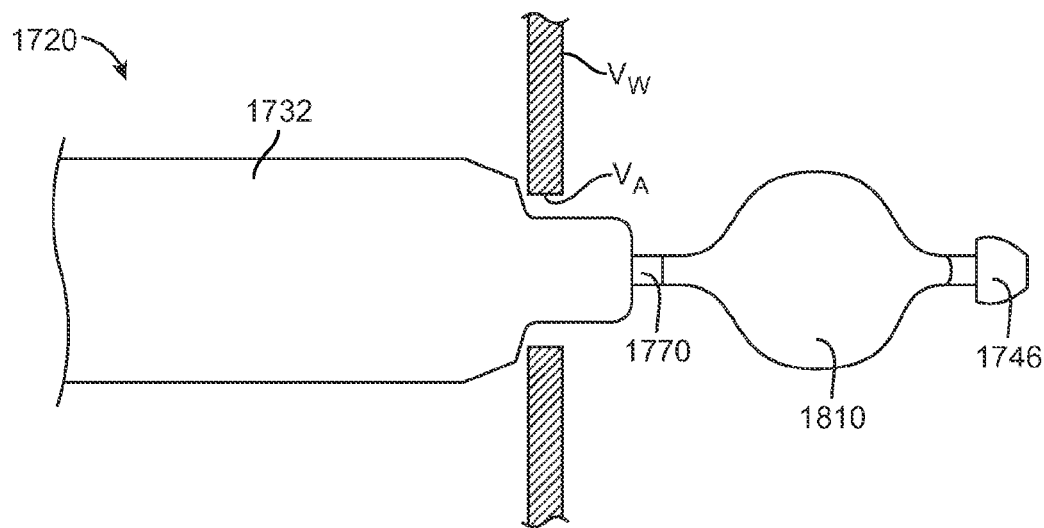
FIG. 26 is a side view illustration of a third step of the method of using the suturing device of FIG. 17 according to an embodiment hereof, wherein the inflatable balloon of the suturing device is inflated or radially expanded.

Next, balloon 1810 is inflated within the lumen of the vessel to an inflated or expanded configuration as shown in FIG. 26. More particularly, a source of inflation fluid is connected to the inflation port of hub 1714 so that balloon 1810 may be inflated as is known to one of ordinary skill in the art. In an embodiment hereof, the inflation fluid may be saline. In another embodiment hereof, the inflation fluid may be a contrast fluid to assist in visualization of balloon 1810 in situ. When inflated, balloon 1810 radially expands and extends away from the elongated body of the suturing device. Balloon 1810 may lie against an inside surface of the vessel wall $V_W$ or be slightly spaced apart from the vessel wall, with the balloon outer surface positioned radially outward of the arteriotomy $V_A$. As such, balloon 1810 provides apposition to vessel wall $V_W$ during the suturing procedure, thereby improving the structural integrity of vessel wall when needle pairs 1756A, 1756B are distally advanced to penetrate through the vessel wall and through inflated balloon 1810 as described in more detail below.

Figure 27:
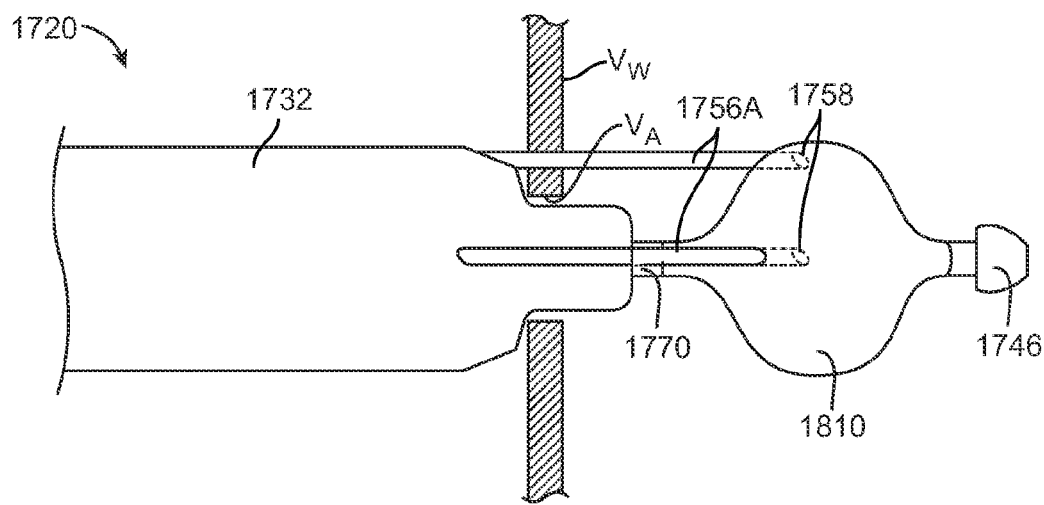
FIG. 27 is a side view illustration of a fourth step of the method of using the suturing device of FIG. 17 according to an embodiment hereof, wherein a pair of needles with sutures therein are deployed to extend through the vessel wall adjacent to the arteriotomy and into the inflated balloon.

After balloon 1810 is inflated, needle pair 1756A and suture pair 1760A are distally advanced or extended to a deployed position in which needle pair 1756A and suture pair 1760A distally extend from a distal end of the elongated body of the suturing device and penetrate through the vessel wall and through inflated balloon 1810. More particularly, as shown in FIG. 27, needle pair 1756A and suture pair 1760A are distally advanced until the respective actuation mechanism has reached a needle deployment position wherein the needles pierce through the vessel wall $V_W$ and extend into balloon 1810. Accordingly, in situ, needle pair 1756A creates incisions or pathways within tissue around the arteriotomy during deployment. In one embodiment, as shown in FIG. 27, only needle pair 1756A is first extended into a lumen of a vessel although, as in the embodiment described above with respect to FIGS. 3-13, it will be understood that both needle pairs may alternatively be extended or deployed into the vessel wall at the same time. Although not visible in the view of FIG. 27, suture pair 1760A extending within and carried with needle pair 1756A is similarly distally advanced concurrently with needle pair 1756A. In order to extend needle pair 1756A and suture pair 1760A to the position shown in FIG. 27, actuator 1766A on handle 1722 is distally advanced until the actuation mechanism associated therewith reaches a needle deployment position as described above with respect to actuator 366A. As previously stated, balloon 1810 is formed from a compliant material that is self-sealing such that the material seals around the needles when the needles penetrate into the inflated balloon. Thus, the insertion and removal of needles through the balloon material does not affect the operation, i.e., the inflation and deflation, of the balloon.

Figure 28:
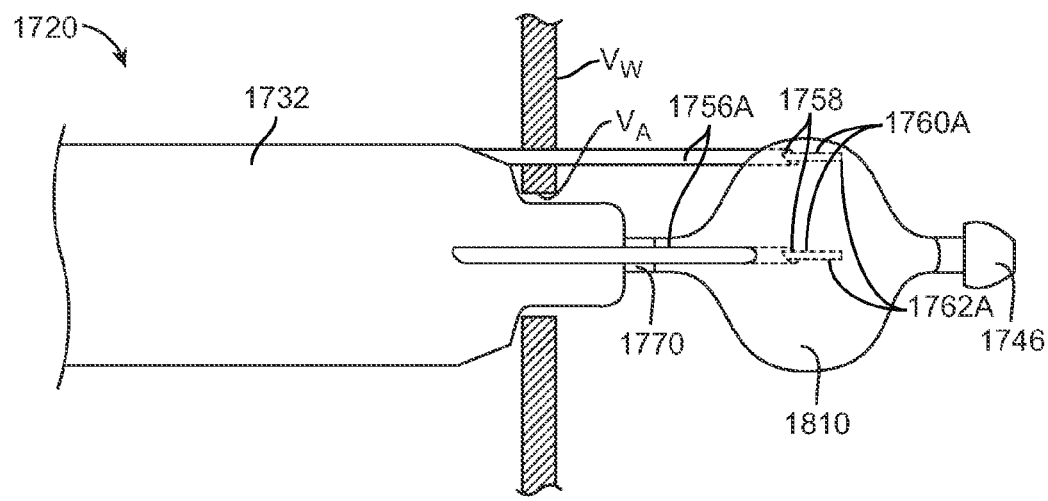
FIG. 28 is a side view illustration of a fifth step of the method of using the suturing device of FIG. 17 according to an embodiment hereof, wherein the sutures are deployed to extend beyond the distal ends of the needles.

First ends 1762A of suture pair 1760A are then deployed out of or beyond distal ends 1758 of needle pair 1756A as shown in FIG. 28. In order to extend or deploy suture pair 1760A out of needle pair 1756A, actuator 1766A on handle 1722 is further distally advanced until the actuation mechanism associated therewith reaches a suture deployment position as described with respect to actuator 366A above. As such, suture pair 1760A is distally advanced relative to needle pair 1756A by continued movement of actuator 1766A. Although the distal advancement of actuator 1766A is described in two sequential method steps within FIGS. 27 and 28, it will be understood by those of ordinary skill in the art that such steps are performed by a single user action, i.e., distal advancement of actuator 1766A.

Figure 29:
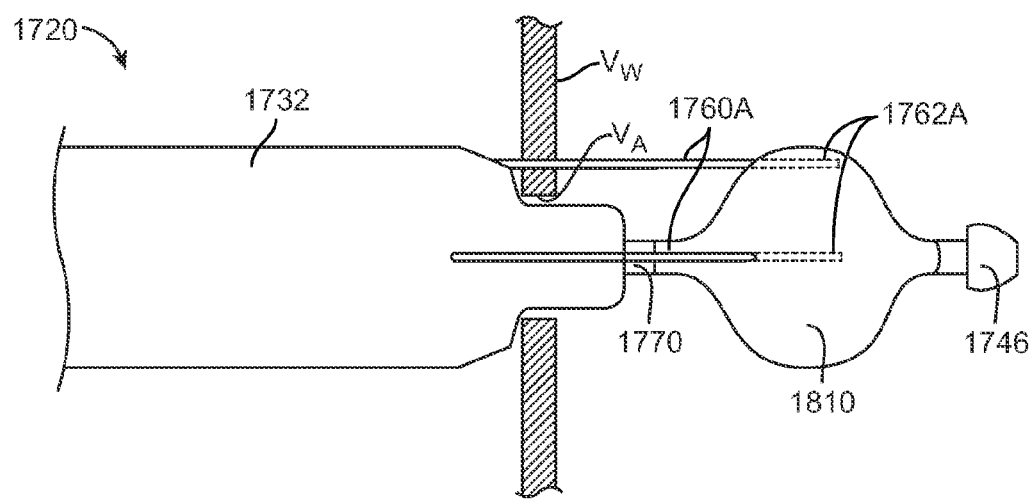
FIG. 29 is a side view illustration of a sixth step of the method of using the suturing device of FIG. 17 according to an embodiment hereof, wherein the pair of needles have been proximally retracted leaving a pair of sutures deployed within the inflated balloon.

After distal portions of suture pair 1760A are extended or deployed beyond needle pair 1756A, needle pair 1756A is retracted as shown in FIG. 29, thereby leaving only the suture ends extending through the vessel wall and within an interior volume of inflated balloon 1810. Needle pair 1756A is retracted and suture pair 1760A remains extended or deployed via operation of actuator 1766A, as described with respect to actuator 366A above.

Figure 30:
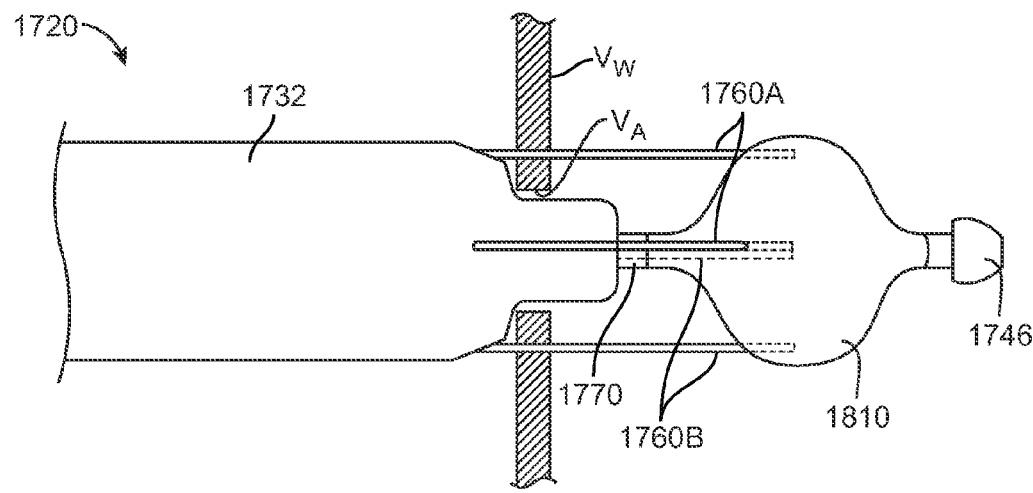
FIG. 30 is a side view illustration of a seventh step of the method of using the suturing device of FIG. 17 according to an embodiment hereof, wherein two sutures are shown extending into the arteriotomy.

As previously mentioned with respect to FIG. 27, it may be desirable to extend only a single needle pair at a time into a lumen of a vessel if the vessel is of a relatively smaller size. If only a single needle pair and corresponding suture pair has been deployed into the lumen of the vessel, the remaining needle pair 1768B and first ends 1762B of suture pair 1760B are subsequently extended into the lumen of the vessel via actuator 1766B as shown in FIG. 30 by following the method steps described above with respect to actuator 1766A. Alternatively, suture pair 1760B may have been extended into the lumen of the vessel via actuator 17668 before or concurrently with suture pair 1760A.

Figure 31:
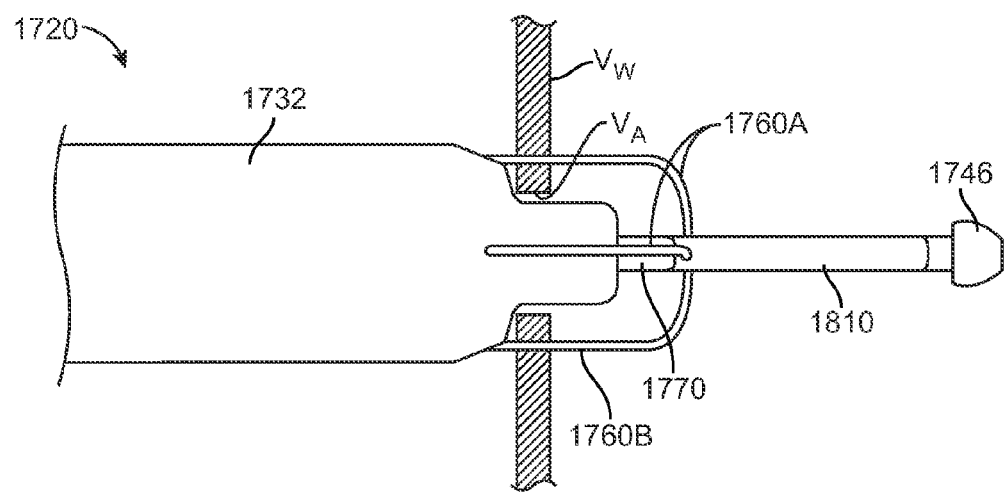
FIG. 31 is a side view illustration of an eighth step of the method of using the suturing device of FIG. 17 according to an embodiment hereof, wherein the inflatable balloon is deflated or unexpanded with the suture ends captured therein.

After respective ends of suture pairs 1760A, 1760B all extend into the lumen of the vessel and both needle pairs 1756A, 1756B have been retracted into elongated body 1724 of the suturing device, balloon 1810 is deflated to thereby capture the four extended suture ends into the balloon as shown in FIG. 31. More particularly, in order to capture the extended suture ends, balloon 1810 deflates and holes formed by the retracted needle pairs compress over or around the sutures. In one embodiment hereof in which balloon 1810 is a pre-formed or pre-blown balloon, a vacuum (not shown) may be applied to hub 1714 in order to remove the inflation fluid from the interior of balloon 1810 and deflate balloon 1810, to as would be understood by one of ordinary skill in the art. When the vacuum is applied and the balloon deflates, the suture ends are compacted, packed, or otherwise clamped within the compressed interior volume of the balloon. In another embodiment hereof in which balloon 1810 is not a pre-formed or pre-blown balloon, the use of a vacuum to deflate balloon 1810 may not be required as described in more detail above. If a vacuum is not applied to deflate the balloon, the inflation fluid leaks out of the holes formed by needle pairs 1756A, 1756B as the balloon reverts or returns to its deflated or delivery configuration.

Figure 32:
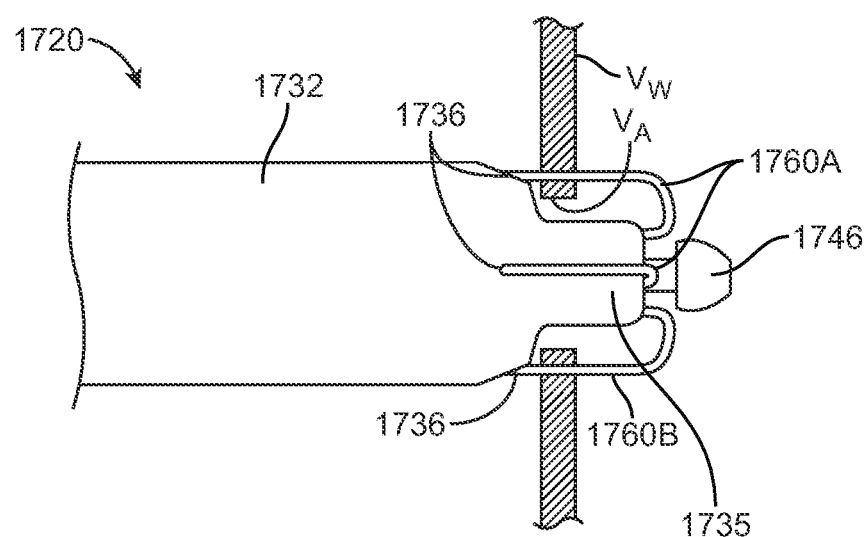
FIG. 32 is a side view illustration of a ninth step of the method of using the suturing device of FIG. 17 according to an embodiment hereof, wherein the transmission shaft and inflatable balloon coupled thereto are proximally retracted, thereby capturing the suture ends within the suturing device.

Once balloon 1810 is deflated with the suture ends captured therein, transmission shaft 1770 and balloon 1810 are proximally retracted until balloon 1810 is positioned within distal guiding component 1732 and/or elongated body 1724 of the suturing device as shown in FIG. 32, thereby pulling the captured first ends of the sutures into the suturing device. In order to proximally retract deflated balloon 1810, actuator or slider 1768 of handle 1722 is proximally retracted such that the actuator pulls or proximally retracts transmission shaft 1770 as described above. When balloon 1810 is disposed within the elongated body of the suturing device, suture pairs 1760A, 1760B extend out of ports 1736 of distal guiding component 1732, through tissue around the arteriotomy $V_A$ via the pathways or incisions created by needle pairs 1756A, 1756B, and then the ends of suture pairs 1760A, 1760B are captured within distal portion 1735 of distal guiding component 1732 as shown in FIG. 32. The friction between deflated balloon 1810 and the inner surface of the distal guiding component 1732 secures or locks the ends of the sutures within the distal guiding component. In addition, when transmission shaft 1770 is retracted, tapered distal tip or nosecone 1746 is adjacent to or abuts against the distalmost end of distal guiding component 1732 to operate as a plug or stop that tightly secures the ends of the sutures within the distal guiding component. At this point in the method of use, suturing device 1720 having the captured suture ends therein is retracted until it is withdrawn from a patient so that a clinician gains access to the second or non-captured suture ends in the same manner as described above with respect to suturing device 320. Once a clinician has gained access to the second suture ends, at least one surgical knot may be tied or formed between the respective second ends of each suture pair to form two elongated sutures that may be manipulated to close or substantially close the arteriotomy $V_A$ in the same manner as described above with respect to FIGS. 12-13 and suturing device 320.

Figure 33:
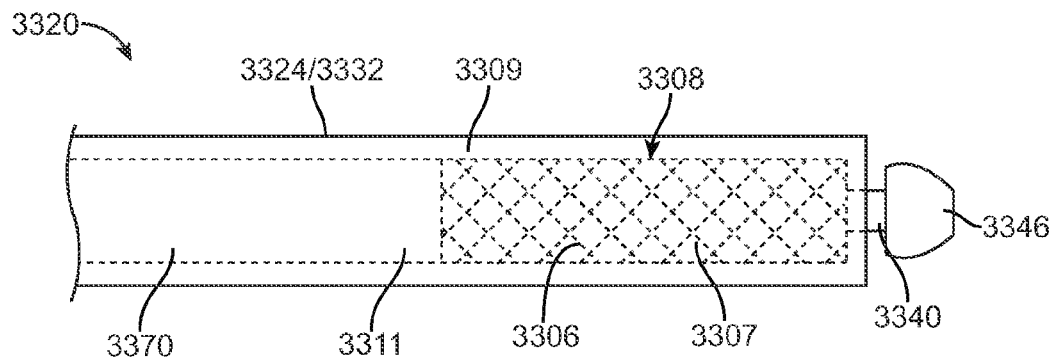
FIG. 33 is a side view of a distal portion of a transmission shaft and an expandable suture capture component coupled thereto according to another embodiment hereof, wherein the expandable suture capture component is in the delivery configuration.
Figure 34:
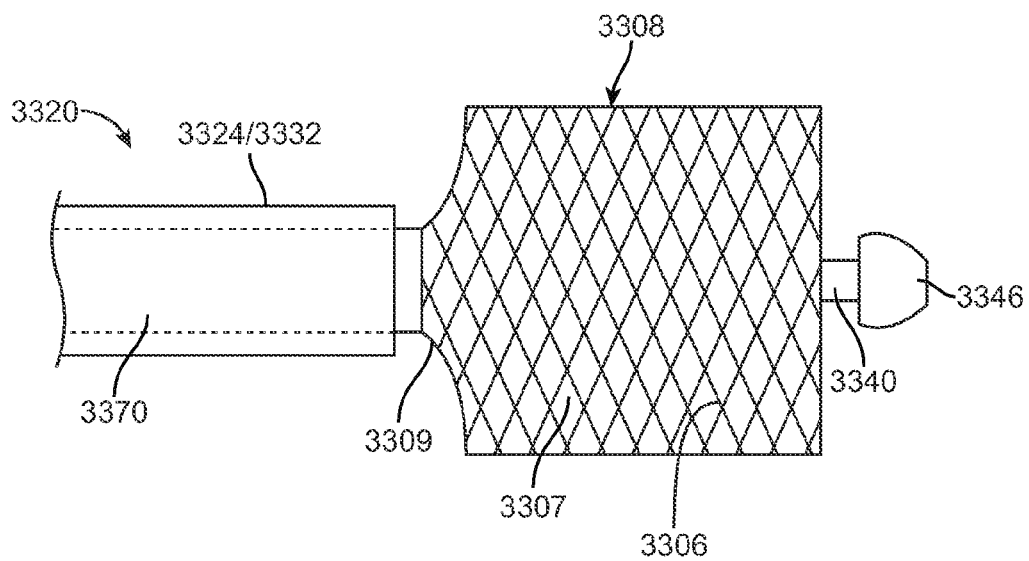
FIG. 34 is a side view of the distal portion of the transmission shaft and the expandable suture capture component of FIG. 33, wherein the expandable suture capture component is in the expanded or deployed configuration.

In another embodiment hereof, the suturing device may include an expandable suture capture or snare component as an alternative for capturing the ends of the suture(s) beyond the boundaries of the arteriotomy. An expandable suture capture or snare component provides a relatively larger target area or zone for placement of the needles of the suturing device and, if desired, may be configured to provide apposition to the inner vessel wall during the suturing procedure, thereby improving the structural integrity of the vessel wall for the needles to puncture or penetrate there through. For example, a suturing device 3320 having a distal guiding component 3332 of an elongated body 3324, a transmission shaft 3370, an inner shaft 3340, and expandable suture capture component 3308 is illustrated in FIGS. 33-34, with expandable suture capture component 3308 in a delivery or compressed configuration in FIG. 33 and in a deployed or expanded configuration in FIG. 34. Only a distal portion of suturing device 3320 is shown in FIGS. 33-34, but it will be understood that by those of ordinary skill in the art that transmission shaft 3370, inner shaft 3340, and expandable suture capture component 3308 may replace transmission shaft 1770 and inflatable balloon 1810 of suturing device 1720. A proximal end 3309 of expandable suture capture component 3308 is coupled to a distal end 3311 of a transmission shaft 3370. Proximal end 3309 of expandable suture capture component 3308 may be spot welded, laser welded or secured using a bonding sleeve or adhesive to transmission shaft 3370 as would be apparent to one skilled in the relevant art. Inner shaft 3340 having a tapered distal tip 3346 coupled to a distal end thereof extends through transmission shaft 3370 and expandable suture capture component 3308.

Expandable suture capture component 3308 is formed from a self-expanding material meaning it has a mechanical memory to return to the expanded or deployed configuration of FIG. 34. Mechanical memory may be imparted to expandable suture capture component 3308 by thermal treatment to achieve a spring temper in stainless steel, for example, or to set a shape memory in a susceptible metal alloy, such as Nitinol. In the delivery or compressed configuration, expandable suture capture component 3308 is a relatively straight cylindrical or tubular structure disposed within distal guiding component 3332 and/or elongated body 3324. The delivery or compressed configuration provides expandable suture capture component 3308 with a minimized delivery profile such that suturing device 3320 may be advanced to the target site. When it is desired to deploy expandable suture capture component 3308, expandable suture capture component 3308 is distally advanced until it is no longer disposed within distal guiding component 3332 and/or elongated body 3324. Once expandable suture capture component 3308 is no longer constrained, it assumes the deployed or expanded configuration of FIG. 34 and radially expands and extends away from distal guiding component 3332 and/or elongated body 3324. An expanded or deployed outer diameter of expandable suture capture component 3308 may vary according to application. In one embodiment, the expanded or deployed outer diameter of expandable suture capture component 3308 is predetermined to be smaller than an inner diameter of the target vessel, i.e., a diameter of the vessel lumen. In another embodiment, the expanded or deployed outer diameter of expandable suture capture component 3308 is predetermined to be equal to or slightly greater than the inner diameter of the target vessel. Stated another way, the expanded or deployed outer diameter of expandable suture capture component 3308 is predetermined to be over-sized with respect to the inner diameter of the target vessel such that when deployed, radially expandable suture capture component 3308 slightly over-expands the vessel and provides apposition to the inner vessel wall during the suturing procedure, thereby improving the structural integrity of the vessel wall for the needles to puncture or penetrate there through.

Expandable suture capture component 3308 includes a tubular braided or mesh structure 3306 that is expandable within a vessel at a treatment site of an arteriotomy. Open spaces 3307 in braided or mesh tubular structure 3306 allow blood or other fluid to flow there-through, such that the blood vessel is not blocked or occluded. In an embodiment, expandable suture capture component 3308 is a tubular braided structure constructed from a plurality of self-expanding metallic wires or filaments woven together to form a tubular or cylindrical structure. In another embodiment, expandable suture capture component 3308 may be constructed from a stamped metallic mesh of self-expanding material. In an embodiment hereof, the mesh pore size is 1000 microns. However, with respect to a minimum mesh pore size, the only requirement is that the mesh pore size may allow a needle to pass there-through. Similarly, with respect to a maximum pore size, the only requirement is that the mesh pore size captures a suture therein when collapsed. Thus, the mesh pore size can vary for example from 50 to 5000 microns. In addition to the size of open spaces 3307 or the mesh pore size, the flexibility and/or strength of expandable suture capture component 3308 may be tailored by controlling the diameter or thickness of the wire utilized in braided or mesh tubular structure 3306 or the thickness of the stamped metallic mesh, respectively. In general, smaller diameters and thicknesses result in a more flexible expandable suture capture component 3308 that conforms and bends to the native anatomy while larger diameters and thicknesses result in a stronger, stiffer expandable suture capture component 3308 that more precisely retains the expanded or deployed configuration in situ. In addition, pics per inch, or the number of winds in each braid per inch thereof, may be varied to tailor the characteristics of expandable suture capture component 3308. In an embodiment hereof, increasing the height and decreasing the width of the number of winds in each braid may more effectively capture or snare the sutures extending therein when expandable suture capture component 3308 is collapsed as described in more detail herein.

Figure 35:
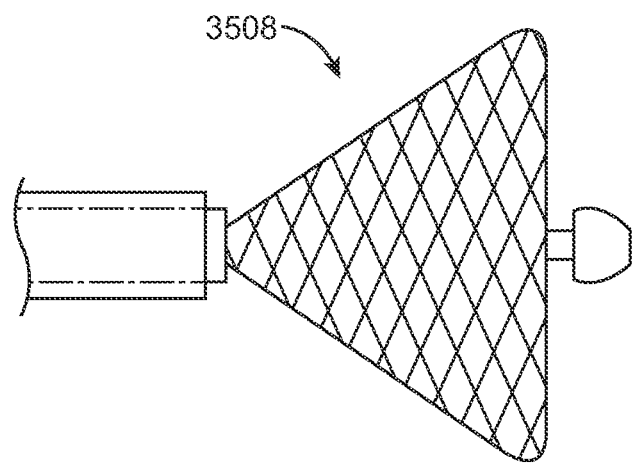
FIG. 35 is a side view of an alternative expanded or deployed configuration of the expandable suture capture component of FIG. 34.
Figure 36:
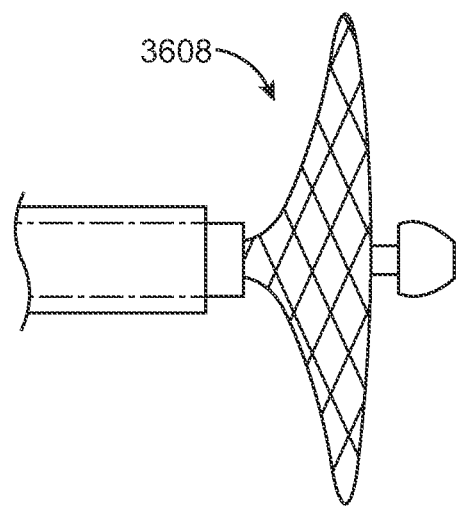
FIG. 36 is a side view of another alternative expanded or deployed configuration of the expandable suture capture component of FIG. 34.
Figure 36A:
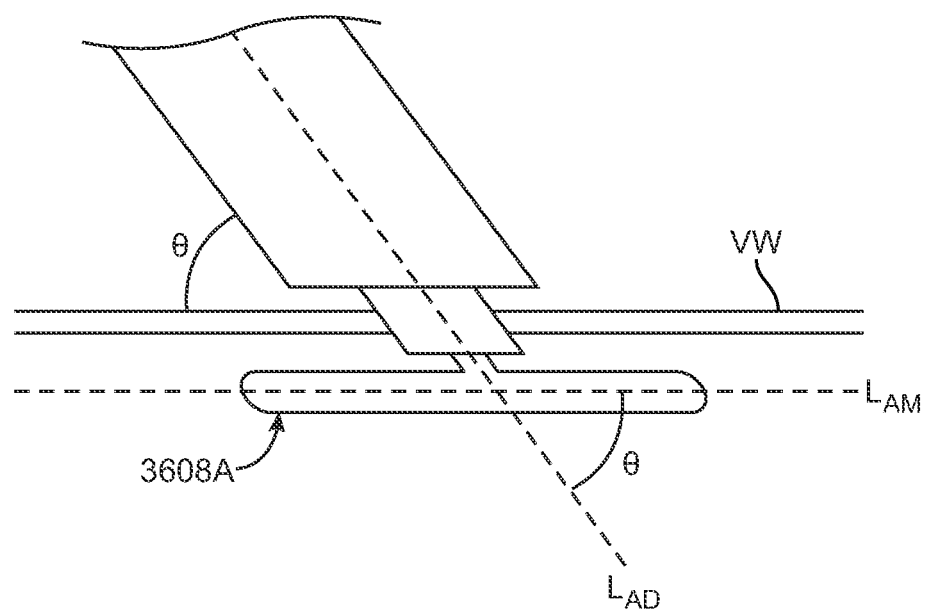
FIG. 36A is a side view of another alternative expanded or deployed configuration of the expandable suture capture component of FIG. 34, wherein the expandable suture capture component is schematically shown within a vessel having a vessel wall VW.

The deployed configuration of expandable suture capture component 3308 is cylindrical. However, the expandable suture capture component may have other deployed configurations that are operable to capture suture ends. For example, FIG. 35 illustrates an expandable suture capture component 3508 having a cone-shaped deployed or expanded configuration and FIG. 36 illustrates an expandable suture capture component 3608 having a disc-shaped deployed or expanded configuration. In addition, FIG. 36A illustrates an expandable suture capture component 3608A having a disc-shaped deployed or expanded configuration that is angled with respect to the longitudinal axis of the suturing device. More particularly, the suturing device may be introduced into a vessel having a vessel wall VW at an acute angle $\ominus$. In one embodiment, acute angle $\ominus$ is between 30 and 45 degrees but may range between 30 and 89 degrees. When deployed or expanded, disc-shaped expandable suture capture component 3608A is angled with respect to the suturing device to compensate or accommodate for the angled introduction into the vessel and permit disc-shaped expandable suture capture component 3608A to lie substantially flat against or parallel to the vessel wall VW of the vessel. As such, when deployed, a longitudinal axis $L_{AM}$ of disc-shaped expandable suture capture component 3608A forms acute angle $\ominus$ with a longitudinal axis $L_{AD}$ of the suturing device. Other deployed configurations are suitable for use herein, such as but not limited to a spherical or ellipsoidal deployed configuration.

Figure 37:
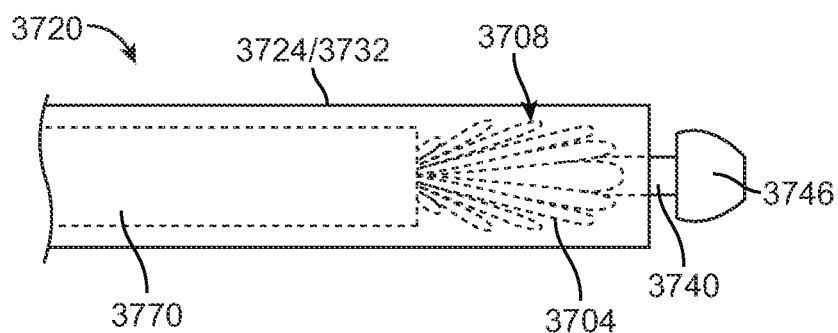
FIG. 37 is a side view of a distal portion of a transmission shaft and an expandable suture capture component coupled thereto according to another embodiment hereof, wherein the expandable suture capture component is in the delivery configuration.
Figure 38:
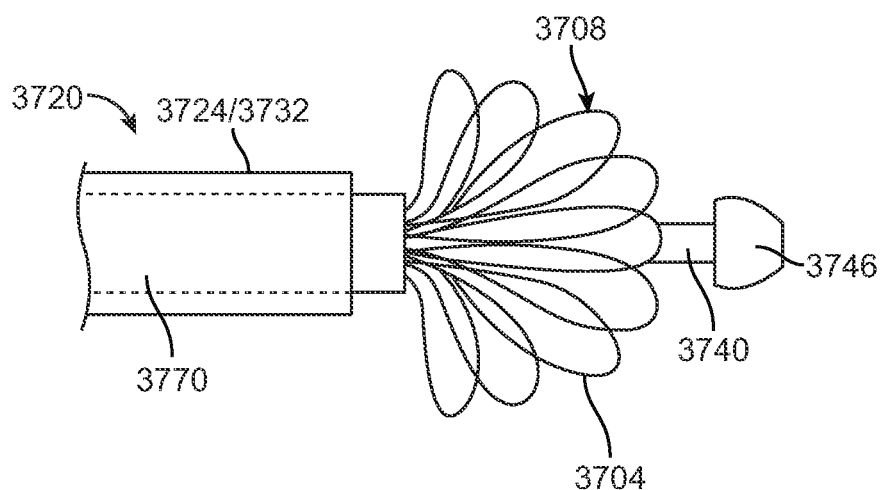
FIG. 38 is a side view of the distal portion of the transmission shaft and the expandable suture capture component of FIG. 37, wherein the expandable suture capture component is in the expanded or deployed configuration.

FIGS. 37-38 illustrate another embodiment of an expandable suture capture component for capturing the ends of the suture(s) beyond the boundaries of the arteriotomy. A suturing device 3720 having a distal guiding component 3732 of an elongated body 3724, a transmission shaft 3770, an inner shaft 3740, and expandable suture capture component 3708 is illustrated in FIGS. 37-38, with expandable suture capture component 3708 in a delivery or compressed configuration in FIG. 37 and in a deployed or expanded configuration in FIG. 38. Inner shaft 3740 having a tapered distal tip 3746 coupled to a distal end thereof extends through transmission shaft 3770 and expandable suture capture component 3708.

Similar to expandable suture capture component 3308, expandable suture capture component 3708 is formed from a self-expanding material meaning it has a mechanical memory to return to the expanded or deployed configuration of FIG. 38. However, in this embodiment, expandable suture capture component 3708 includes a plurality of overlapping or overlaying loops 3704. In the delivery or compressed configuration, loops 3704 of expandable suture capture component 3708 are compressed together and disposed within distal guiding component 3732 and/or elongated body 3724. When it is desired to deploy expandable suture capture component 3708, expandable suture capture component 3708 is distally advanced until it is no longer disposed within distal guiding component 3732 and/or elongated body 3724. Once expandable suture capture component 3708 is no longer constrained, it assumes the deployed or expanded configuration of FIG. 38 and the plurality of loops 3704 radially expand and extend away from distal guiding component 3732 and/or elongated body 3824.

Figure 39:
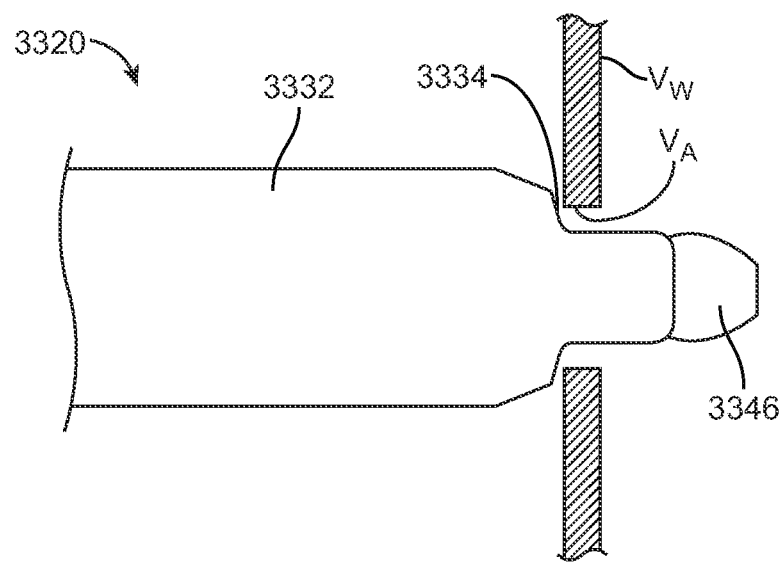
FIG. 39 is a side view illustration of a first step of the method of using the suturing device of FIG. 33 according to an embodiment hereof, wherein the suturing device is advanced towards and positioned through the arteriotomy.

The method for utilizing expandable suture capture components 3308, 3708 for capturing the ends of the suture(s) beyond the boundaries of the arteriotomy is similar to the method for utilizing inflatable balloon 1810 described with respect to FIGS. 24-32. More particularly, FIGS. 39-45 illustrate a method of using suturing device 3320 in order to position two sutures at an arteriotomy of a vessel wall of a vessel. Referring to FIG. 39, suturing device 3320 is shown advanced to a position in which a distal portion thereof is positioned through a target arteriotomy $V_A$ such that distal tip 3346 is disposed within a lumen of the vessel. Suturing device 3320 is in a delivery configuration, in which expandable suture capture component 3308 is in a delivery configuration and disposed within the elongated body of the suturing device. In addition, needle pairs 3356A, 3356B and suture pairs 3360A, 3360B are in a loaded position as described above with respect to previous embodiments. Similar to distal guiding component 332, distal guiding component 3332 includes a stepped or tapered region which creates an abutment surface 3334 that contacts the vessel wall, thereby notifying the user that the suturing device is in place within the arteriotomy $V_A$ as desired.

Figure 40:
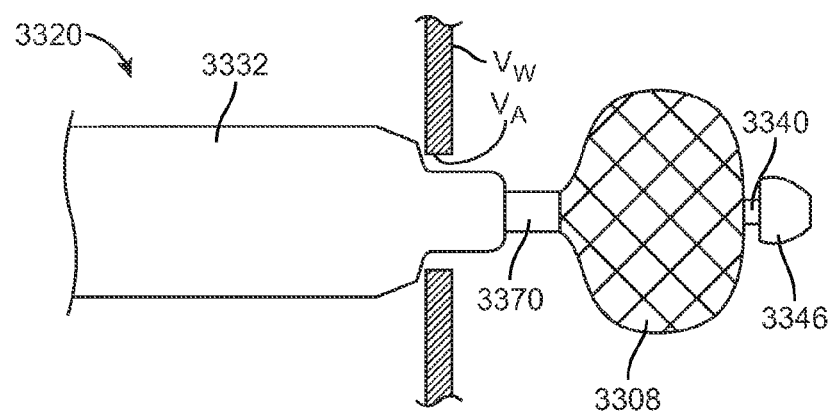
FIG. 40 is a side view illustration of a second step of the method of using the suturing device of FIG. 33 according to an embodiment hereof, wherein the expandable suture capture component of the suturing device is distally advanced in order to expand the expandable suture capture component of the suturing device.

Once the distal portion of distal guiding component 3332 is positioned through the arteriotomy $V_A$ of the vessel to reside within the lumen of the vessel, transmission shaft 3370 and expandable suture capture component 3308 coupled thereto are distally advanced or extended into the lumen of the vessel. When expandable suture capture component 3308 is released from distal guiding component 3332, it self-expands to its deployed configuration in which the expandable suture capture component radially expands and extends away from the elongated body as shown in FIG. 40. Expanded suture capture component 3308 may lie against an inside surface of the vessel wall $V_W$ or be slightly spaced apart from the vessel wall, with the component's outer surface positioned radially outward of the arteriotomy $V_A$. As such, expandable suture capture component 3308 provides apposition to vessel wall $V_W$ during the suturing procedure, thereby improving the structural integrity of vessel wall when needle pairs 3356A, 3356B are distally advanced to penetrate through the vessel wall and through expanded suture capture component 3308 as described in more detail below.

Figure 41:
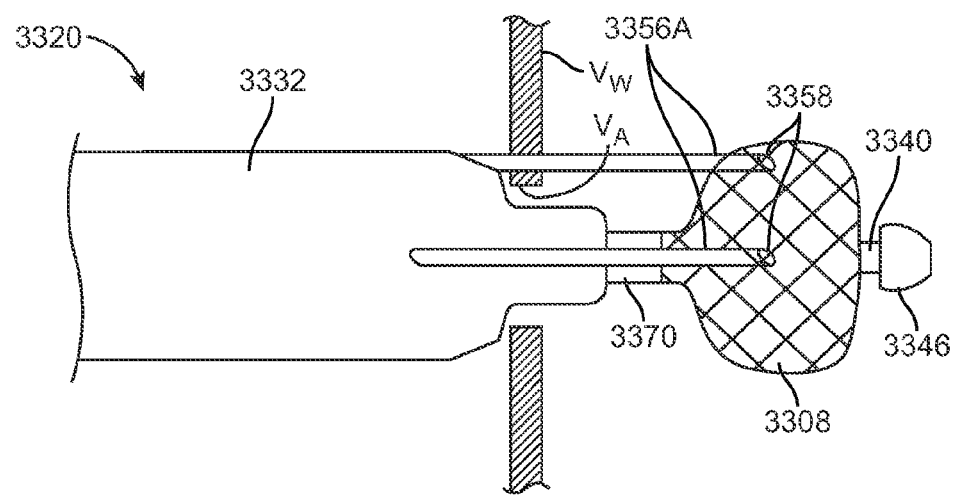
FIG. 41 is a side view illustration of a third step of the method of using the suturing device of FIG. 33 according to an embodiment hereof, wherein a pair of needles with sutures therein are deployed to extend through the vessel wall adjacent to the arteriotomy and into the expandable suture capture component.

After expandable suture capture component 3308 is deployed or expanded, needle pair 3356A and suture pair 3360A are distally advanced or extended to a deployed position in which needle pair 3356A and suture pair 3360A distally extend from a distal end of the elongated body of the suturing device and penetrate through the vessel wall and through expanded suture capture component 3308. More particularly, as shown in FIG. 41, needle pair 3356A and suture pair 3360A are distally advanced until the respective actuation mechanism has reached a needle deployment position wherein the needles pierce through the vessel wall $V_W$ and extend into the open spaces of the braided or mesh tubular structure of expanded suture capture component 3308. Accordingly, in situ, needle pair 3356A creates incisions or pathways within tissue around the arteriotomy during deployment. In one embodiment, as shown in FIG. 41, only needle pair 3356A is first extended into a lumen of a vessel although, as in the embodiment described above with respect to FIGS. 3-13, it will be understood that both needle pairs may alternatively be extended or deployed into the vessel wall at the same time. However, in this embodiment, unlike previous embodiments described herein, non-simultaneous deployment of the needle pairs is not required to accommodate smaller vessel sizes since expandable suture capture component 3308 expands to its expanded or deployed configuration within the vessel lumen and accommodates a range of vessel sizes. Although not visible in the view of FIG. 41, suture pair 3360A extending within and carried with needle pair 3356A is similarly distally advanced concurrently with needle pair 3356A.

Figure 42:
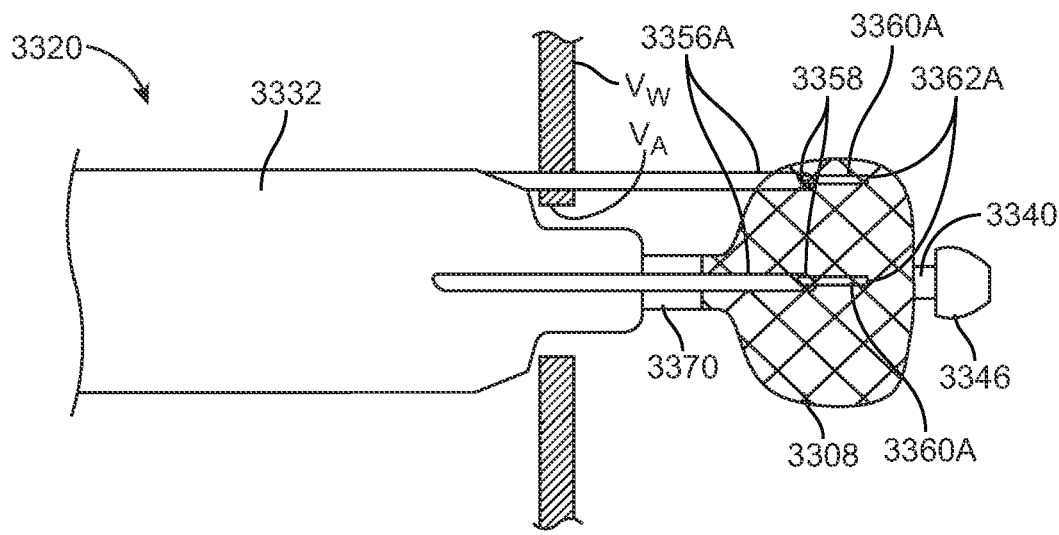
FIG. 42 is a side view illustration of a fourth step of the method of using the suturing device of FIG. 33 according to an embodiment hereof, wherein the sutures are deployed to extend beyond the distal ends of the needles.

First ends 3362A of suture pair 3360A are then deployed out of or beyond distal ends 3358 of needle pair 3356A as shown in FIG. 42. In order to extend or deploy suture pair 3360A out of needle pair 3356A, the actuator or slider associated therewith is further distally advanced until it reaches a suture deployment position as described with respect to actuator 366A above. As such, suture pair 3360A is distally advanced relative to needle pair 3356A by continued movement of the actuator associated therewith.

Figure 43:
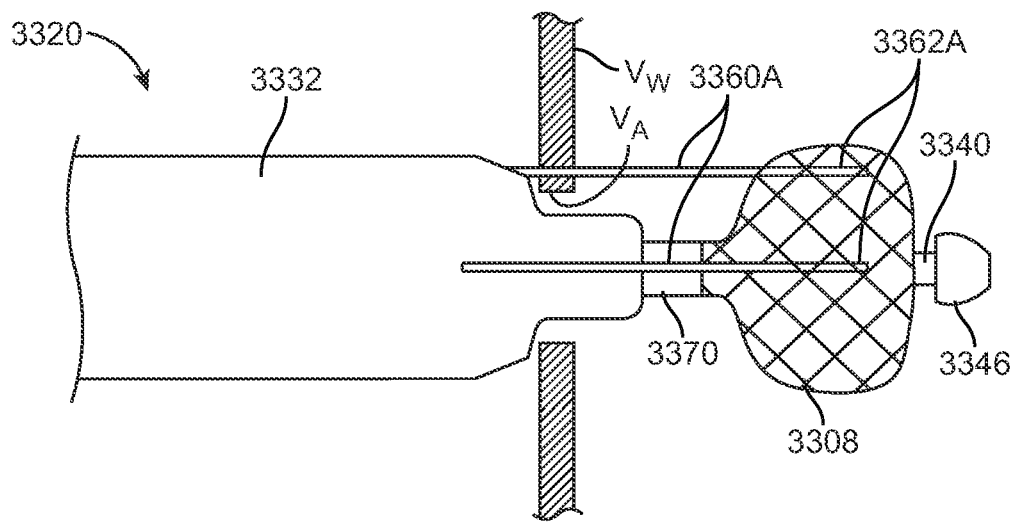
FIG. 43 is a side view illustration of a fifth step of the method of using the suturing device of FIG. 33 according to an embodiment hereof, wherein the pair of needles have been proximally retracted leaving a pair of sutures deployed within the expandable suture capture component.

After distal portions of suture pair 3360A are extended or deployed beyond needle pair 3356A, needle pair 3356A is retracted as shown in FIG. 43, thereby leaving only the suture ends extending through the vessel wall and within an interior volume of expanded suture capture component 3308. Needle pair 3356A is retracted and suture pair 3360A remains extended or deployed via operation of the actuator or slider associated therewith, as described with respect to actuator 366A above.

Figure 44:
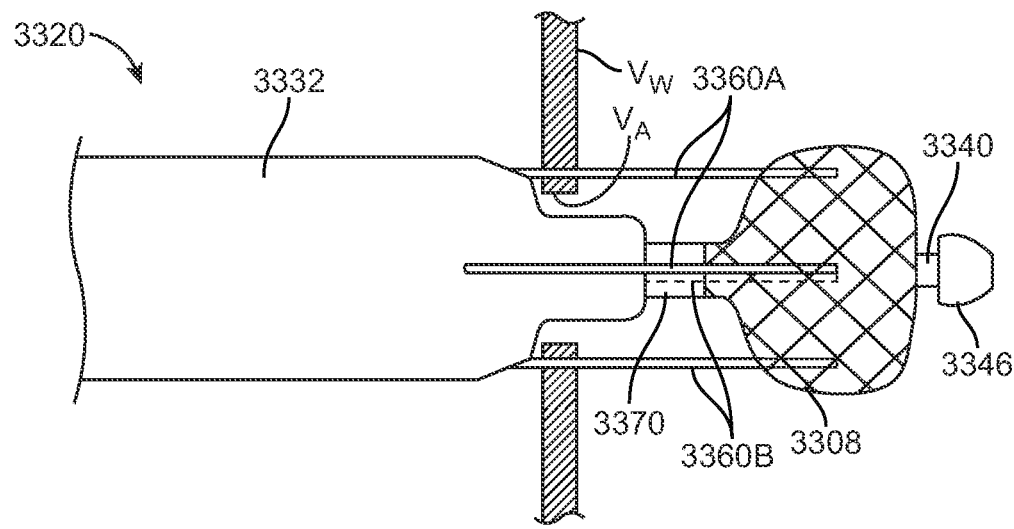
FIG. 44 is a side view illustration of a sixth step of the method of using the suturing device of FIG. 33 according to an embodiment hereof, wherein two sutures are shown extending into the arteriotomy.

As previously mentioned with respect to FIG. 41, it may be desirable to extend only a single needle pair at a time into a lumen of a vessel if the vessel is of a relatively smaller size. If only a single needle pair and corresponding suture pair has been deployed into the lumen of the vessel, the remaining needle pair 3368B and first ends 3362B of suture pair 3360B are subsequently extended into the lumen of the vessel via the actuator or slider associated therewith as shown in FIG. 44 by following the method steps described above for needle pair 3368A and suture pair 3360A. Alternatively, suture pair 3360B may have been extended into the lumen of the vessel via the actuator or slider associated therewith before or concurrently with suture pair 3360A.

Figure 45:
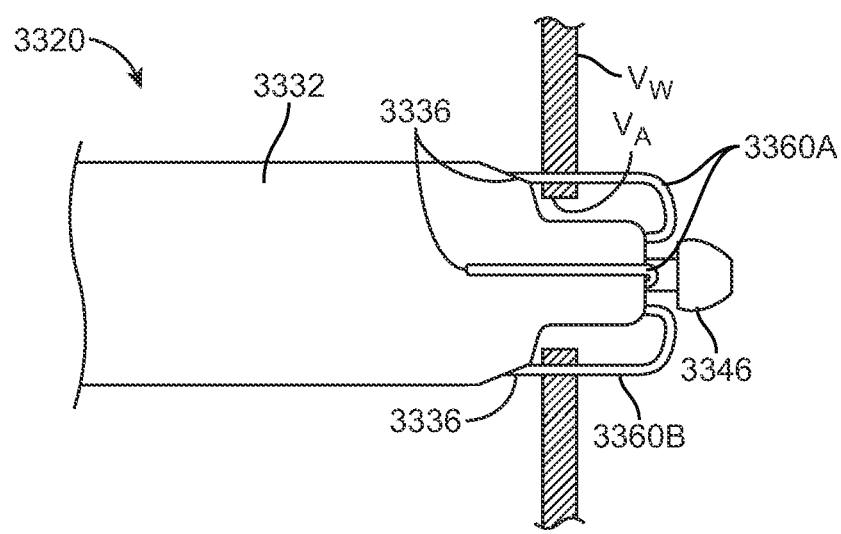
FIG. 45 is a side view illustration of a seventh step of the method of using the suturing device of FIG. 33 according to an embodiment hereof, wherein the transmission shaft and expandable suture capture component coupled thereto are proximally retracted, thereby capturing the suture ends within the suturing device.

After respective ends of suture pairs 3360A, 3360B all extend into the lumen of the vessel and both needle pairs 3356A, 3356B have been retracted into elongated body 3324 of the suturing device, transmission shaft 3370 and expandable suture capture component 3308 coupled thereto are proximally retracted back into distal guiding component 3332 and/or elongated body 3324 of the suturing device, thereby collapsing the expandable suture capture component to the compressed configuration and pulling the four extended suture ends into the elongated body of the suturing device as shown in FIG. 45. More particularly, in order to capture the extended suture ends, the suture ends are ensnared or trapped within the compressed interior volume of suture capture component 3308 when the suture capture component is pulled into the elongated body of the suturing device. When suture capture component 3308 is disposed within the elongated body of the suturing device, suture pairs 3360A, 3360B extend out of ports 3336 of distal guiding component 3332, through tissue around the arteriotomy $V_A$ via the pathways or incisions created by needle pairs 3356A, 3356B, and then the ends of suture pairs 3360A, 3360B are captured within distal guiding component 3332. The friction between compressed suture capture component 3308 and the inner surface of the distal guiding component 3332 secures or anchors the ends of the sutures within the distal guiding component. In addition, tapered distal tip or nosecone 3346 is adjacent to or abuts against the distalmost end of distal guiding component 3332 to operate as a plug or stop that tightly secures the ends of the sutures within the distal guiding component. At this point in the method of use, suturing device 3320 having the captured suture ends therein is retracted until it is withdrawn from a patient so that a clinician gains access to the second or non-captured suture ends in the same manner as described above with respect to suturing device 320. Once a clinician has gained access to the second suture ends, at least one surgical knot may be tied or formed between the respective second ends of each suture pair to form two elongated sutures that may be manipulated to close or substantially close the arteriotomy $V_A$ in the same manner as described above with respect to FIGS. 12-13 and suturing device 320.

Figure 46:
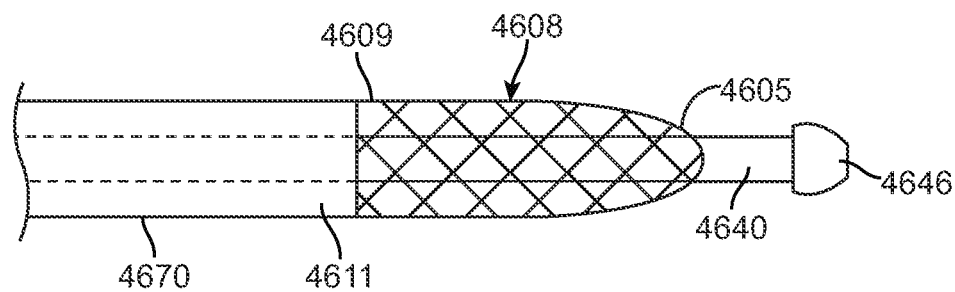
FIG. 46 is a side view of a distal portion of a transmission shaft and an expandable suture capture component coupled thereto according to another embodiment hereof, wherein the expandable suture capture component is in the delivery configuration.
Figure 47:
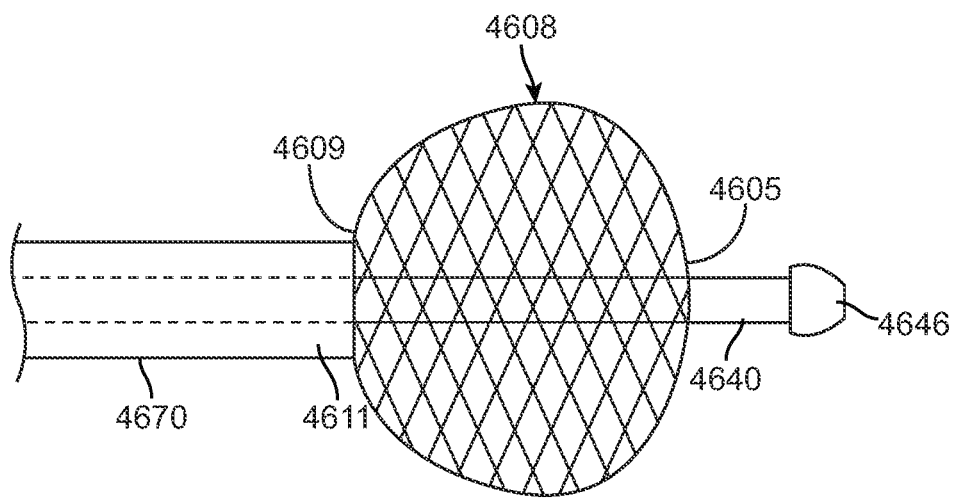
FIG. 47 is a side view of the distal portion of the transmission shaft and the expandable suture capture component of FIG. 46, wherein the expandable suture capture component is in the expanded or deployed configuration.

The expandable suture capture components described herein self-expand to their deployed or expanded configurations upon release or exit from the suturing device. However, it will be understood by one of ordinary skill in the art that deployment or expansion of the expandable suture capture components may be accomplished via other mechanisms. For example, expandable suture capture components may be coupled to both the transmission shaft and the inner or guidewire shaft, and expansion thereof may be accomplished via relative motion between the shafts. More particularly, a transmission shaft 4670, an inner shaft 4640, and expandable suture capture component 4608 is illustrated in FIGS. 46-47, with expandable suture capture component 4608 in a delivery or collapsed configuration in FIG. 46 and in a deployed or expanded configuration in FIG. 47. Only a distal portion of transmission shaft 4670 and inner shaft 4640 are shown in FIGS. 46-47, but it will be understood that by those of ordinary skill in the art that transmission shaft 4670, inner shaft 4640, and expandable suture capture component 4608 may replace transmission shaft 3370, inner shaft 3340, and expandable suture capture component 3308 of suturing device 3320. A proximal end 4609 of expandable suture capture component 4608 is coupled to a distal end 4611 of transmission shaft 4670. Inner shaft 4640 having a tapered distal tip 4646 coupled to a distal end thereof extends through transmission shaft 4670 and expandable suture capture component 4608. A distal end 4605 of expandable suture capture component 4608 is coupled to inner shaft 4640, proximal to tapered distal tip 4646. Expandable suture capture component 4608 may be spot welded, laser welded or secured using a bonding sleeve or adhesive to transmission shaft 4670 and inner shaft 4640 as would be apparent to one skilled in the relevant art.

Expandable suture capture component 4608 is expanded and contracted by relative movement between inner shaft 4640 and transmission shaft 4670. While inner shaft 4640 remains stationary or fixed, transmission shaft 4670 and expandable suture capture component 4608 coupled thereto are distally advanced over inner shaft 4640. When transmission shaft 4670 is distally advanced, the attachment point or bond between expandable suture capture component 4608 and inner shaft 4640 remains fixed such that expandable suture capture component 4608 radially expands to the bulbous or spherical deployed configuration shown in FIG. 47. Similarly, when transmission shaft 4670 and expandable suture capture component 4608 coupled thereto are proximally retracted over inner shaft 4640, expandable suture capture component 4608 collapses or straightens back to the delivery configuration of FIG. 46. Although described with transmission shaft 4670 being movable relative to inner shaft 4640 to expand expandable suture capture component 4608, it should be apparent to one of ordinary skill in the art that expandable suture capture component 4608 is expanded by shortening the distance between proximal and distal ends 4609, 4605 thereof. Thus, in another embodiment, expandable suture capture component 4608 may be expanded by proximally retracting inner shaft 4640 while holding transmission shaft 4670 stationary. In addition, expandable suture capture component 4608 may be expanded by a combination of distally advancing transmission shaft 4670 and proximally retracting inner shaft 4640.

When expansion of expandable suture capture component 4608 is accomplished via relative motion between the transmission shaft and inner shaft, the expandable suture capture component may be constructed from polymeric materials that are less traumatic than the metallic self-expanding materials that are utilized for expandable suture capture component 3308. In addition, when expansion of expandable suture capture component 4608 is accomplished via relative motion between the transmission shaft and inner shaft, the outer expanded or deployed diameter of the expandable suture capture component may be selectively controlled or varied in situ. For example, expandable suture capture component 4608 may be expanded to be selectively over-sized with respect to the inner diameter of the target vessel such that when deployed, radially expandable suture capture component 4608 slightly over-expands the vessel and provides apposition to the inner vessel wall during the suturing procedure, thereby improving the structural integrity of the vessel wall for the needles to puncture or penetrate there through.

Figure 48:
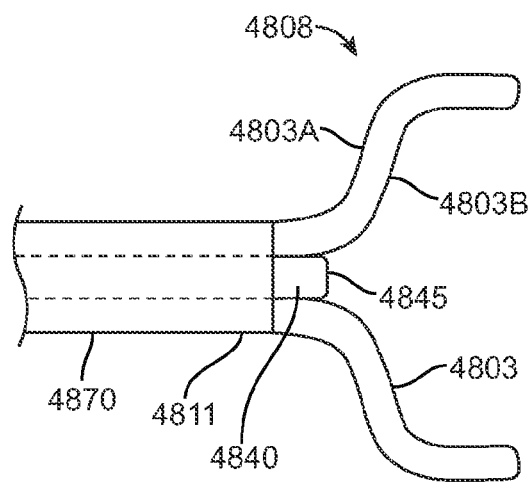
FIG. 48 is a side view of the distal portion of the transmission shaft and the expandable suture capture component coupled thereto according to another embodiment hereof, wherein the expandable suture capture component is in the expanded or deployed configuration.

FIG. 48 illustrates another embodiment of an expandable suture capture component 4808 having dual mesh layers 4803A, 4803B. More particularly, a transmission shaft 4870, an inner shaft 4840, and expandable suture capture component 4808 is illustrated in FIG. 48, with expandable suture capture component 4808 in a deployed or expanded configuration in FIG. 48. Only a distal portion of transmission shaft 4870 and inner shaft 4840 are shown in FIG. 48, but it will be understood that by those of ordinary skill in the art that transmission shaft 4870, inner shaft 4840, and expandable suture capture component 4808 may replace transmission shaft 3370, inner shaft 3340, and expandable suture capture component 3308 of suturing device 3320. First or outer layer 4803A of expandable suture capture component 4808 is coupled to a distal end 4811 of transmission shaft 4870. Inner shaft 4840 extends through transmission shaft 4870 and second or inner layer 4803B of expandable suture capture component 4808 is coupled to a distal end 4845 of inner shaft 4840. Each layer 4803A, 4803B is formed from a self-expanding material, and each layer may be spot welded, laser welded or secured using a bonding sleeve or adhesive to transmission shaft 4870 and inner shaft 4840 as would be apparent to one skilled in the relevant art.

Figure 48A:
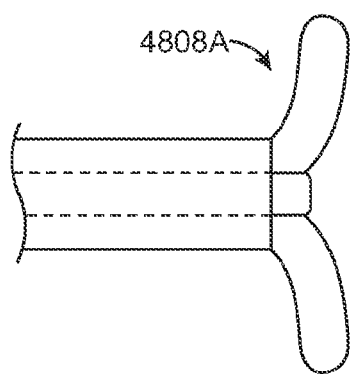
FIG. 48A is a side view of another alternative expanded or deployed configuration of the expandable suture capture component of FIG. 48.
Figure 48B:
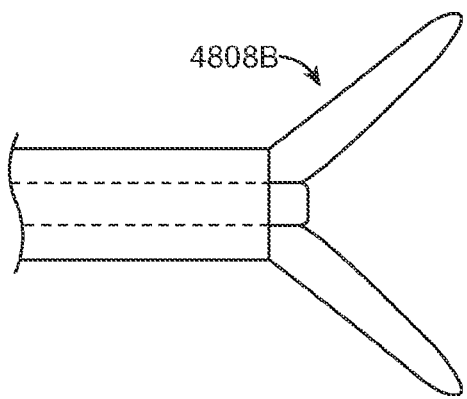
FIG. 48B is a side view of another alternative expanded or deployed configuration of the expandable suture capture component of FIG. 48.

Transmission shaft 4870 and inner shaft 4840 are independently or separately controlled at a proximal end of the suturing device (not shown) and, as such, expansion or deployment of outer and inner layers 4803A, 4803B of expandable suture capture component 4808 are independently or separately controlled by operation of its respective shaft, i.e., operation of transmission shaft 4870 controls expansion or deployment of outer layer 4803A coupled thereto and operation of inner shaft 4840 controls expansion or deployment of inner layer 4803B coupled thereto. Independent control of each layer may allow a user to better secure the suture ends within expandable suture capture component 4808. For example, after a suture is positioned through both layers of expandable suture capture component 4808, a user may selectively contract inner layer 4803B in order to bend the suture ends with respect to outer layer 4803A, thereby improving retention of the suture end within expandable suture capture component 4808. The deployed configuration of dual layer expandable suture capture component 4808 is exemplary and other deployed configurations may be utilized. For example, FIG. 48A illustrates a dual layer expandable suture capture component 4808A having an open-ended disc-shaped deployed or expanded configuration and FIG. 48B illustrates a dual layer expandable suture capture component 4808B having an open-ended cone-shaped deployed or expanded configuration.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A suturing device, comprising:
a handle;
an elongated body coupled to a distal end of the handle;
a shaft slidingly disposed within the handle and the elongated body, wherein an expandable suture capture component is mounted on a distal portion of the shaft, the expandable suture capture component being operable to alternate between a deployed configuration in which the expandable suture capture component radially expands and extends away from the elongated body and a compressed configuration in which the expandable suture capture component is disposed within the elongated body,
at least one pair of needles moveable to a deployed position in which the at least one pair of needles distally extend from the distal end of the elongated body and into the expandable suture capture component with the expandable suture capture component in its deployed configuration and a retracted position in which the at least one pair of needles is disposed within the elongated body, each needle including a distal end configured to penetrate through a vessel wall.

2. The suturing device of claim 1, wherein the expandable suture capture component includes a mesh tubular structure.

3. The suturing device of claim 1, wherein the expandable suture capture component includes a plurality of looped segments.

4. The suturing device of claim 1, wherein the looped segments are formed from a self-expanding material.

5. The suturing device of claim 1, wherein the deployed configuration of the expandable suture capture component is disc-shaped.

6. The suturing device of claim 1, wherein the deployed configuration of the expandable suture capture component is cone-shaped.

7. The suturing device of claim 1, wherein the expandable suture capture component has two mesh layers.

8. The suturing device of claim 1, further comprising:
a suture slidingly disposed through a lumen of each needle, a first end of each suture being disposed within its respective needle when the needle is in its deployed position, wherein each suture is moveable relative to its respective needle to a deployed position in which the first end of the suture extends distally from the distal end of its respective needle.

9. The suturing device of claim 8, wherein each suture remains in its deployed position when its respective needle is moved to its retracted position.

10. The suturing device of claim 1, wherein the elongated body comprises:
    an outer shaft, wherein the outer shaft defines a central lumen there through and at least two grooves for slidingly receiving the pair of needles there through;
    a distal guiding component coupled to a distal end of the outer shaft, wherein the distal guiding component includes a central lumen there through mating with the central lumen of the outer shaft and at least two lumens mating with the at least two grooves of the outer shaft for guiding the pair of needles between the retracted position and the deployed position.

11. A suturing device for positioning a suture in situ, comprising:
    a handle having a first actuation mechanism and a second actuation mechanism, wherein the second actuation mechanism includes a suture holder and a needle holder disposed within the handle;
    an elongated body coupled to a distal end of the handle;
    a shaft slidingly disposed within the handle and the elongated body, the shaft being moveable via the first actuation mechanism, wherein an expandable suture capture component is mounted on a distal portion of the shaft and the expandable suture capture component is moveable between a deployed configuration in which the expandable suture capture component radially expands and extends away from the elongated body and a compressed configuration in which the expandable suture capture component is disposed within the elongated body,
    a pair of needles extending through the handle and through the elongated body, each needle including a distal end configured to penetrate through a vessel wall, wherein the pair of needles is coupled to the needle holder and wherein the second actuation mechanism moves the pair of needles to a deployed position in which the pair of needles distally extend away from the distal end of the elongated body and into the expandable suture capture component with the expandable suture capture component in its deployed configuration and a retracted position in which the pair of needles is disposed within the elongated body; and
    a pair of sutures slidingly disposed through the pair of needles, wherein the sutures are coupled to the suture holder when the needles are in their deployed position and are disengaged from the suture holder when the needles are in their retracted position and wherein the second actuation mechanism moves the pair of sutures relative to the pair of needles from a loaded position in which each first end of each suture is disposed within its respective needle to a deployed position in which each first end of each suture extends distally beyond the distal end of its respective needle.

12. The suturing device of claim 11, wherein the expandable suture capture component includes a mesh tubular structure.

13. The suturing device of claim 11, wherein the expandable suture capture component includes a plurality of looped segments.

14. The suturing device of claim 11, wherein the deployed configuration of the expandable suture capture component is disc-shaped.

15. The suturing device of claim 11, wherein the deployed configuration of the expandable suture capture component is cone-shaped.

16. The suturing device of claim 11, wherein the expandable suture capture component has two mesh layers.

17. A method of positioning a suture at an arteriotomy of a vessel wall of a vessel, wherein the method includes the steps of:
    positioning a distal end of a suturing device through the arteriotomy, wherein the suturing device includes a handle, an elongated body, coupled to a distal end of the handle, and a shaft slidingly disposed within the handle and the elongated body, wherein an expandable suture capture component is mounted on a distal portion of the shaft and is in a compressed configuration in which the expandable suture capture component is disposed within the elongated body;
    expanding the expandable suture capture component to a deployed configuration in which the expandable suture capture component radially expands and extends away from the elongated body, wherein the expanded expandable suture capture component is positioned within the vessel; and
    distally extending at least one pair of needles of the suturing device from a loaded position in which the at least one pair of needles is disposed within the elongated body to a deployed position in which the at least one pair of needles distally extend from a distal end of the elongated body and penetrate through the vessel wall and through the expanded expandable suture capture component, wherein a suture is slidingly disposed through the lumen of each needle and each suture is concurrently carried with its respective needle during the step of distally extending the at least one pair of needles to the deployed position.

18. The method of claim 17, further comprising the steps of:
    distally advancing the sutures relative to their respective needles from a loaded position in which a first end of each suture is disposed within its respective needle to a deployed position in which the first end of each suture extends distally away from the distal end of its respective needle;
    retracting the at least one pair of needles to a retracted position in which the at least one pair of needles is disposed within the elongated body, wherein the sutures remain in their deployed positions within an interior volume of the expandable suture capture component during the step of retracting the at least one pair of needles; and
    collapsing the expandable suture capture component to the compressed configuration, thereby pulling the first ends of the sutures into the elongated body of the suturing device.

19. The method of claim 17, wherein the step of expanding the expandable suture capture component includes distally advancing the shaft to expose the expandable suture capture component.

20. The method of claim 19, wherein the expandable suture capture component is formed from a self-expanding material.

* * * * *